(12) United States Patent
Altenbach et al.

(10) Patent No.: US 7,098,222 B2
(45) Date of Patent: Aug. 29, 2006

(54) BICYCLIC-SUBSTITUTED AMINES HAVING CYCLIC-SUBSTITUTED MONOCYCLIC SUBSTITUENTS

(75) Inventors: Robert J. Altenbach, Chicago, IL (US); Lawrence A. Black, Libertyville, IL (US); Sou-Jen Chang, Prairie View, IL (US); Marlon D. Cowart, Round Lake Beach, IL (US); Ramin Faghih, Lake Forest, IL (US); Gregory A. Gfesser, Lindenhurst, IL (US); Yi-Yin Ku, Buffalo Grove, IL (US); Huaqing Liu, Buffalo Grove, IL (US); Kirill A. Lukin, Mundelein, IL (US); Diana L. Nersesian, Gurnee, IL (US); Yu-ming Pu, Gurnee, IL (US); Michael P. Curtis, Kenosha, WI (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 11/123,620

(22) Filed: May 6, 2005

(65) Prior Publication Data

US 2005/0272728 A1    Dec. 8, 2005

Related U.S. Application Data

(60) Provisional application No. 60/570,186, filed on May 12, 2004.

(51) Int. Cl.
*A61K 31/47* (2006.01)
*A61K 31/40* (2006.01)
*C07D 215/12* (2006.01)
*C07D 401/04* (2006.01)
*C07D 207/09* (2006.01)

(52) U.S. Cl. ............ 514/314; 514/422; 546/167; 546/176; 548/518

(58) Field of Classification Search ........ 514/314, 514/422; 546/167, 176; 548/518
See application file for complete search history.

(56) References Cited

U.S. PATENT DOCUMENTS

| 1,860,286 | A | | 5/1932 | Hartman et al. | |
|---|---|---|---|---|---|
| 3,489,756 | A | | 1/1970 | Bolhofer et al. | 260/247.7 |
| 3,639,476 | A | | 2/1972 | Eberle et al. | 260/563 |
| 5,457,112 | A | * | 10/1995 | Cremer et al. | 514/314 |
| 6,225,328 | B1 | | 5/2001 | Bernardon | 514/356 |
| 6,358,515 | B1 | | 3/2002 | Ogata et al. | 424/401 |

FOREIGN PATENT DOCUMENTS

| CH | 149 007 | 11/1931 |
|---|---|---|
| DE | 556 324 | 8/1932 |
| GB | 1 122 756 | 8/1968 |
| GB | 1178400 | 1/1970 |
| WO | 94/17079 | 8/1994 |
| WO | 95/01426 | 1/1995 |
| WO | 95/09159 | 4/1995 |
| WO | 98/38156 | 9/1998 |
| WO | 98/57931 | 12/1998 |
| WO | 00/06254 | 2/2000 |
| WO | 00/27815 | 5/2000 |
| WO | 02/074758 | 9/2002 |
| WO | 03/093237 | 11/2003 |
| WO | 2004/026864 | 4/2004 |
| WO | 2004/043458 | 5/2004 |

OTHER PUBLICATIONS

Airaksinen et al., "Histamine Neurons in Human Hypothalamus: Anatomy in Normal and Alzeimer Diseased Brains," Neuroscience 44(2):465-481 (1991).

Andrés et al., "A Simple Steroselective Synthesis Of Enantiopure 2-Substituted Pyrrolidines and Piperidines From Chiral (*R*)-Phenylglycinol-Derived Bicyclic 1,3-Oxazolidines," Eur. J. Org. Chem. 1719-1726 (2000).

Aranyos et al., "Novel Electron-Rich Bulky Phosphine Ligands Facilitate the Palladium-Catalyzed Preparation of Diaryl Ethers," J. Am Chem. Soc. 121:4369-4378 (1999).

Arrang, J-M., "Auto-inhibition of brain histamine release mediated by a novel class ($H_3$) of histamine receptor", *Nature*, 302:832-837 (1983).

(Continued)

*Primary Examiner*—Kamal A. Saeed
*Assistant Examiner*—Joseph R. Kosack
(74) *Attorney, Agent, or Firm*—Portia Chen

(57) ABSTRACT

Compounds of formula (I)

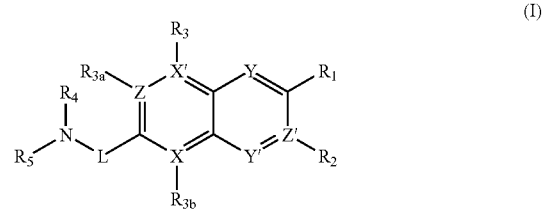

(I)

wherein $R_1$ or $R_2$ is an aromatic or non-aromatic ring directly joined or joined by a linker, as represented by $L_2$ and $L_3$, to a heteroaromatic core, and X, X', Y, Y', Z, Z', $R_1$, $R_2$, $R_3$, $R_{3a}$, $R_{3b}$, $R_4$, $R_5$, L, $L_2$, and $L_3$ are as defined herein, are useful in treating conditions or disorders prevented by or ameliorated by histamine-3 receptor ligands. Also disclosed are pharmaceutical compositions comprising the histamine-3 receptor ligands, methods for using such compounds and compositions, and a process for preparing compounds within the scope of formula (I).

13 Claims, No Drawings

OTHER PUBLICATIONS

Arrang, J-M., "Highly potent and selective ligands for histamine H$_3$-receptors", *Nature*, 327:117-123 (1987).

Bachman et al., "Quinoline Derivatives from 2- and 4-Chloroquinolines," Journal of Organic Chemistry, American Chemical Society. Easton, US 9:302-309 (1944).

Baston et al., "A New Route To 6-Aryl-Substituted 3,4-Dihydronaphthalene Derivates Via Pd (O)-Catalyzed Cross-Coupling Reaction of Aryl Zinc Chlorides With an Aryl Triflate," Synthetic Communication 28(14):2725-2729 (1998).

Bjenning et al., "Peripherally Administered Ciproxifan Elevates Hypothalamic Histamine Levels And Potently Reduces Food Intake in the Sprague Dawley Rat," Histamine Research In The New Mellennium, Proceedings Of The International Sendai Histamine Symposium Held In Sendai, Japan, Nov. 22-25, 2000, p. 449-450.

Coutts et al., "Calmodulin Antagonists as Potential Antifungal Agents," Pesticide Science, Elsevier Applied Science Publisher. Barking, GB 51(1):99-101 (1997).

Dai et al., "The First General Method For Palladium-Catalyzed Negishi Cross-Coupling Of Aryl and Vinyl Chlorides: Use of Commercially Available Pd(P(t-Bu)$_3$)$_2$ as a Catalyst," J. Am. Chem Soc. 123:2719-2724 (2001).

De Almeida et al., "Memory Facilitation by Histamine," Arch. Int. Pharmacodyn., 283:193-198 (1986).

Delaunois et al., "Modulation Of Acetylcholine, Capsaicin and Substance P Effects by Histamine H$_3$ Receptors in Isolated Perfused Rabbit Lungs," European Journal Of Pharmacology, 277:243-250 (1995).

Dimitriadou et al., "Functional Relationship Between Mast Cells and C-Sensitive Nerve Fibres Evidenced by Histamine H$_3$-Receptor Modulation in Rat Lung and Spleen," Clinical Science, 87:151-163 (1994).

Dohle et al., "Copper-Mediated Cross-Coupling of Functionalized Arylmagnesium Reagents with Functionalized Alkyl and Benzylic Halides," Organic Letters 3(18):2871-2873 (2001).

Duméry et al., "Development of Amygdaloid Cholinergic Mediation of Passive Avoidance Learning in the Rat," Exp. Brain. Res., 67:61-69 (1987).

Ellingboe et al., "Antihyperglycemic Activity of Novel Naphthalenyl 3*H*-1,2,3,5-Oxathiadiazole 2-Oxides," J. Med. Chem. 36:2485-2493 (1993).

Elworthy et al., "The Configurational Stability of Chiral Lithio α-Amino Carbanions. The Effect of Li-O *vs*. Li-N Complexation," Tetrahedron 50(20):6089-6096 (1994).

Fitzsimons et al., "Histamine Receptors Signalling in Epidermal Tumor Cell Lines With H-*ras* Gene Alterations," Inflamm. Res., 47, Supplement 1, S50-S51 (1998).

Fox et al., "Effects of Histamine H$_3$Receptor Ligands GT-2331 And Ciproxifan in a Repeated Acquisition Response in the Spontaneously Hypertensive Rat Pup," Behavioural Brain Research 131:151-161 (2002).

Gaffield et al., "Chiroptical Properties of N-Nitrosopyrrolidines and N-Nitrosamino Acids," Tetrahedron 37:1861-1869 (1981).

Haas et al., Subcortical Modulation of Synaptic Plasticity in the Hippocampus, Behavioural Brain Research, 66:41-44 (1995).

Hartwig, "Transition Metal Catalyzed Synthesis of Arylamines and Aryl Ethers From Aryl Halides and Triflates: Scope And Mechanism," Angew. Chem. Int. Ed. 37:2046-2067 (1998).

Hatta et al., "Activation of Histamine H$_3$ Receptors Inhibits Carrier-Mediated Norepinephrine Release in a Human Model of Protracted Myocardial Ischemia[1,2]," The Journal Of Pharmacology And Experimental Therapeutics, 283(2):494-500 (1997).

Imamura et al., "Activation Of Histamine H$_3$-Receptors Inhibits Carrier-Mediated Norepinephrine Release During Protracted Myocardial Ischemia," Circulation Research, 78(3):475-481 (1996).

Imamura et al., "Histamine H$_3$-Receptor-Mediated Inhibition Of Calcitonin Gene-Related Peptide Release From Cardiac C Fibers," Circulation Research, 78(5):863-869 (1996).

Itoh et al., "Thioperamide, A Histamine H$_3$ Receptor Antagonist, Powerfully Suppresses Peptide YY-Induced Food Intake In Rats," Biol. Psychiatry 45:475-481 (1999).

Kamei et al., "Influence Of Certain H$_1$-Blockers On The Step-Through Active Avoidance Response In Rats," Psychopharmacology, 102:312-318 (1990).

Kamei et al., "Paticipation Of Histamine In The Step-Through Active Avoidance Response And Its Inhibition By H$_1$-Blockers," Japan J. Pharmacol., 57:473-482 (1991).

Karrer et al., Helvetica Chimica Acta. 34(270):2202-2210 (1951).

Kiyomori et al., "An Efficient Copper-Catalyzed Coupling Of Aryl Halides With Imidazoles," Tetrahedron Letters 40:2657-2660 (1999).

Klapars et al., "A General And Efficient Copper Catalyst For The Amidation of Aryl Halides And The *N*-Arylation Of Nitrogen Heterocycles," J. Am. Chem. Soc. 123:7727-7729 (2001).

Kwong et al., "Copper-Catalyzed Coupling Of Alkylamines And Aryl Iodides: An Efficient System Even In An Air Atmosphere," Organic Letters 4(4):581-584 (2002).

Leurs et al., "The Histamine H$_3$-Receptor: A Target For Developing New Drugs," Progress In Drug Research, 39:127-165 (1992).

Leurs et al., "The Medicinal Chemistry And Therapeutic Potentials Of Ligands Of The Histamine H$_3$ Receptor," Progress In Drug Research, 45:107-165 (1995).

Leurs et al., "Therapeutic Potential Of Histamine H$_3$ Receptor Agonists And Antagonists," Trends In Pharm. Sci, 19:177-183 (1998).

Levi et al., "Histamine H$_3$-Receptors: A New Frontier In Myocardial Ischemia," The Journal Of Pharmacology And Experimental Therapeutics, 292(3):825-830 (2000).

Li et al., "Highly Active, Air-Stable Versatile Palladium Catalysts For The C-C, C-N, And C-S Bond Formations Via Cross-Coupling Reactions Of Aryl Chlorides," J. Org. Chem. 66:8677-8681 (2001).

Li et al., "The First Phosphine Oxide Ligand Precursors For Transition Metal Catalyzed Cross-Coupling Reactions: C-C, C-N, And C-S Bond Formation On Unactivated Aryl Chlorides," Angew. Chem. Int. Ed. 40(8):1513-1516 (2001).

Lin et al., "Involvement Of Histaminergic Neurons In Arousal Mechanisms Demonstrated With H$_3$-Receptor Ligands In The Cat," Brain Research, 523-325-330 (1990).

Lipshutz et al., "Efficient Scavenging of PH$_3$P And Ph$_3$P=O With High-Loading Merrifield Resin," Organic Letters 3(12):1869-1871 (2001).

Lipshutz et al., "Substitution Reactions Of Aryl *Chlorides* With Organozinc Reagents Catalyzed By Ni(0)," Tetrahedron Letters 40:197-200 (1999).

Littke et al., "Versatile Catalysts For The Suzuki Cross-Coupling Of Arylboronic Acids With Aryl And Vinyl Halides And Triflates Under Mild Conditions," J. Am. Chem. Soc. 122:4020-4028 (2000).

Marcoux et al., "A General Copper-Catalyzed Synthesis Of Diaryl Ethers," J. Am. Chem. Soc. 119:10539-10540 (1997).

Matsubara et al., "UK-14,304, R(-) α-Methyl-Histamine And SMS 201-995 Block Plasma Protein Leakage Within Dura Mater By Prejunctional Mechanisms," European Journal Of Pharmacology, 224:145-150 (1992).

Mazurkiewicz-Kwilecki et al., "Changes In The Regional Brain Histamine And Histidine Levels In Postmortem Brains Of Alzheimer Patients," Can. J. Physiol. Pharmacol, 67: 75-78 (1989).

McLeod et al., "Histamine H$_3$ Antagonists," Progress In Resp. Research 31:133-134 (2001).

Miyaura et al., "Palladium-Catalyzed Cross-Coupling Reactions Of Organoboron Compounds," Chem. Rev. 95:2457-2483 (1995).

Mohanakrishnan et al., "Pd(0)-Mediated Cross Coupling Of 2-Iodoestradiol With Organozinc Bromides: A General Route To The Synthesis Of 2-Alkynyl, 2-Alkenyl And 2-Alkylestradiol Analogs," Synlett. 7:1097-1099 (1999).

Molander et al., "Cross-Coupling Reactions Of Primary Alkylboronic Acids With Aryl Triflates And Aryl Halides," Tetrahedron 58:1465-1470 (2002).

Monti et al., "Effects Of Selective Activation Or Blockade Of The Histamine H$_3$ Receptor On Sleep And Wakefulness," European Journal Of Pharmacology, 205:283-287 (1991).

Monti et al., "Sleep And Waking During Acute Histamine H$_3$ Agonist BP2.94 Or H$_3$ Antagonist Carboperamide (MR 16155) Administration In Rats," Neuropsychopharmacology, 15(1):31-35 (1996).

Murakami et al., "AQ-0145, A Newly Developed Histamine $H_3$ Antagonist, Decreased Seizure Susceptibility Of Electrically Induced Convulsions In Mice," Meth. Find. Exp. Clin. Pharmacol. 17(C):70-73 (1995).

Nijhuis et al., "Stereochemical Aspects Of The "*Tert*-Amino Effect." 2. Enantio- And Diastereoselectivity In The Synthesis Of Quinolines, Pyrrolo[1,2-α]Quinolines, And [1,4]Oxazino[4,3-α]Quinolines," J. Org. Chem. 54:209-216 (1989).

Onodera et al., "Neuropharmacology Of The Histaminergic Neuron System In The Brain And Its Relationship With Behavioral Disorders," Progress In Neurobiology, 42:685-702 (1994).

Palomo et al., "Phosphazene Bases For The Preparation Of Biaryl Thioethers From Aryl Iodides And Arenethiols," Tetrahedron Letters 41:1283-1286 (2000).

Palucki et al., "Palladium-Catalyzed Intermolecular Carbon-Oxygen Bond Formation: A New Synthesis Of Aryl Ethers," J. Am. Chem. Soc. 119:3395-3396 (1997).

Pan et al., "Histaminergic Ligands Attenuate Barrel Rotation in Rats Following Unilateral Labyrinthectomy," Meth. Find Exp. Clin. Pharmacol 20(9):771-777 (1998).

Panula et al., "Brain Histamine In Pathophysiological Conditions And Brain Diseases," The Histamine $H_3$ Receptor, 243-253 (1998).

Perez-Garcia et al., "Effects Of Histamine $H_3$ Receptor Ligands In Experimental Models Of Anxiety And Depression," Psychopharmacology 142:215-220 (1999).

Phillips et al., "Recent Advances In Histamine $H_3$ Receptor Agents," Annual Reports In Medicinal Chemistry, 33:31-40 (1998).

Rouleau, "Bioavailabillity, Antinociceptive And Antiiflammatory Properties Of BP 2-94, A Histamine $H_3$ Receptor Agonist Prodrug," The Journal Of Pharmacology And Experimental Therapeutics, 281(3):1085-1094 (1997).

Sakai et al., "Effects Of Thioperamide, A Histamine $H_3$ Receptor Antagonist, On Locomotor Activity And Brain Histamine Content In Mast Cell-Deficient W/WvMice," Life Sciences, 48:2397-2404 (1991).

Schopfer et al., "A General Palladium-Catalysed Synthesis Of Aromatic And Heteroaromatic Thioethers," Tetrahedron 57:3069-3073 (2001).

Schwartz et al., "Histaminergic Transmission in the Mammalian Brain," Physiological Reviews 71(1):1-51 (1991).

Schwartz et al., "Histamine," Psychopharmacology: The Fourth Generation Of Progress, 397-405 (1995).

Shaywitz et al., "Dopaminergic But Not Noradrenergic Mediation Of Hyperactivity And Performance Deficits In The Developing Rat Pup," Psychopharmacology, 82:73-77 (1984).

Sugahara et al., "A Facile Copper-Catalyzed Ullmann Condensation:*N*-Arylation Of Heterocyclic Compounds Containing an -NHCO- Moiety," Chem. Pharm. Bull. 45(4):719-721 (1997).

Suzuki, "Recent Advances In The Cross-Coupling Reactions Of Organoboron Derivates With Organic Electrophiles, 1995-1998," Journal Of Organometallic Chemistry 576:147-168 (1999).

Szelag, "Role Of Histamine $H_3$-Receptors In The Proliferation Of Neoplastic Cells In Vitro," Med. Sci. Monit., 4(5):747-755 (1998).

Tedford et al., "Cognition And Locomotor Activity In The Developing Rat: Comparisons Of Histamine $H_3$ Receptor Antagonists And ADHD Therapeutics," Socity for Neuroscience Abstr., 22:22 (1996).

Tedford et al., "Pharmacological Characterization Of GT-2016, A Non-Thiourea-Containing Histamine $H_3$ Receptor Antagonist: *In Vitro* And *In Vivo* Studies," The Journal Of Pharmacology And Experimental Therapeutics, 275(2):598-604 (1995).

Tedford, "Clinical Application Of HA $H_3$ Receptor Antagonists In Learning And Memory Disorders," The Histamine $H_3$ Receptor 269-286 (1998).

Toshimitsu et al., "Preparation, Structure, And Reactivity Of Pentacoordinate Disilanes Bearing An 8-Charcogeno-1-Naphthyl Group And A Heteroatom On The Same Silicon Atom," Heteroatom Chemistry 12(5):392-397 (2001).

Vernsten et al., "Halogen Substituted Aryl Alkamine Ethers," Journal of the American Chemical Society 78:5398-5400 (1956).

Wada et al., "Is The Histaminergic Neuron System A Regulatory Center For Whole-Brain Activity?, "Trends In Neurosciences, 14(9):415-418 (1991).

Wear et al., "The Synthesis of Some Quinoxaline Derivatives," Journal of the American Chemical Society 72:2893-2894 (1950).

Wolfe et al., "Rational Development Of Practical Catalysts For Aromatic Carbon-Nitrogen Bond Formation," Acc. Chem. Res. 31:805-818 (1998).

Wolfe et al., "Simple, Efficient Catalyst System For The Palladium-Catalyzed Amination Of Aryl Chlorides, Bromides, And Triflates," J. Org. Chem. 65:1158-1174 (2000).

Yamada et al., "A Biogenetic-Type Asymmetric Cyclization Syntheses Of Optically Active α-Cyclocitral And Trans-α-Damascone," Tetrahedron Letters 5:381-384 (1973).

Yamamoto et al., "Ullmann Condensation Using Copper Or Copper Oxide As The Reactant. Arylation Of Active Hydrogen Compound (Imides, Amides, Amines, Phenol, Benzoic Acid, And Phenylacetylene)," Can. J. Chem. 61:86-91 (1983).

Yang et al., "Palladium-Catalyzed Animation Of Aryl Halides And Sulfonates," Journal of Organometallic Chemistry 576:125-146 (1999).

Yates et al., "Effects Of A Novel Histamine $H_3$ Receptor Antagonist, GT-2394, On Food Intake And Weight Gain In Sprague-Dawley Rats," Abstracts, Society For Neuroscience, 102.10:219 (Nov. 2000).

Yokoyama et al., "Effect Of Thioperamide, A Histamine $H_3$ Receptor Antagonist, On Electrically Induced Convulsions In Mice," Journal Of Pharmacology, 234:129-133 (1993).

Yokoyama et al., "Histamine And Seizures Implications For The Treatment Of Epilepsy," CNS Drugs, 5(5):321-330 (1996).

Zou et al., "Ag(I)-Promoted Suzuki-Miyaura Cross-Couplings of *N*-Alkylboronic Acids," Tetrahedron Letters 42:7213-7215 (2001).

Apelt, J., et al., "Development of a New Class of Nonimidazole Histamine $H_3$ Receptor Ligands with Combined Inhibitory Histamine *N*-Methyltransferase Activity", *J. Med. Chem.*, 45:1128-1142 (2002).

Grassmann, S., et al., "Imidazole Derivatives as a Novel Class of Hybrid Compounds with Inhibitory Histamine *N*-Methyltransferase Potencies and Histamine $hH_3$ Receptor Affinities", *Biorganic& Medicinal Chem.*, 11:2163-2174 (2003).

* cited by examiner

BICYCLIC-SUBSTITUTED AMINES HAVING CYCLIC-SUBSTITUTED MONOCYCLIC SUBSTITUENTS

This application claims priority to U.S. Provisional Application No. 60/570,186, filed on May 12, 2004, the complete disclosure of which is herein incorporated by reference.

BACKGROUND OF THE INVENTION

1. Technical Field

The invention relates to bicyclic-substituted amine compounds, compositions comprising such compounds, methods for making the compounds, and methods of treating conditions and disorders using such compounds and compositions. More particularly, the amine compounds have cyclic-substituted monocyclic substituents.

2. Description of Related Technology

Histamine is a well-known modulator of neuronal activity. At least four types of histamine receptors have been reported in the literature, typically referred to as histamine-1, histamine-2, histamine-3, and histamine-4. The class of histamine receptor known as histamine-3 receptors is believed to play a role in neurotransmission in the central nervous system.

The histamine-3 ($H_3$) receptor was first characterized pharmacologically on histaminergic nerve terminals (Nature, 302:832–837 (1983)), where it regulates the release of neurotransmitters in both the central nervous system and peripheral organs, particularly the lungs, cardiovascular system and gastrointestinal tract. $H_3$ receptors are thought to be disposed presynaptically on histaminergic nerve endings, and also on neurons possessing other activity, such as adrenergic, cholinergic, serotoninergic, and dopaminergic activity. The existence of $H_3$ receptors has been confirmed by the development of selective $H_3$ receptor agonists and antagonists ((Nature, 327:117–123 (1987); Leurs and Timmerman, ed. "The History of $H_3$ Receptor: a Target for New Drugs," Elsevier (1998)).

The activity at the $H_3$ receptors can be modified or regulated by the administration of $H_3$ receptor ligands. The ligands can demonstrate antagonist, agonist or partial agonist activity. For example, $H_3$ receptors have been linked to conditions and disorders related to memory and cognition processes, neurological processes, cardiovascular function, and regulation of blood sugar, among other systemic activities. Although various classes of compounds demonstrating $H_3$ receptor-modulating activity exist, it would be beneficial to provide additional compounds demonstrating activity at the $H_3$ receptors that can be incorporated into pharmaceutical compositions useful for therapeutic methods.

SUMMARY OF THE INVENTION

One aspect of the invention relates to compounds of the formula:

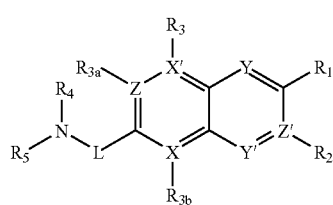

(I)

or a pharmaceutically acceptable salt, ester, amide, or prodrug thereof, wherein:

Y, and Y' are each independently selected from the group consisting of CH, CF, and N;

X, X', Z, and Z' are each independently C or N;

one of $R_1$ and $R_2$ is a group of the formula $-L_2-R_{6a}-L_3-R_{6b}$;

the other of $R_1$ and $R_2$ is selected from the group consisting of hydrogen, alkyl, alkoxy, aryl, cycloalkyl, halogen, cyano, and thioalkoxy, provided that $R_2$ is absent when Z' is N;

$R_3$ is absent when X' is N or $R_3$ is selected from the group consisting of hydrogen, alkyl, alkoxy, halogen, cyano, and thioalkoxy;

$R_{3a}$ is absent when Z is N or $R_{3a}$ is selected from the group consisting of hydrogen, methyl, alkoxy, halogen, and cyano;

$R_{3b}$ is absent when X is N or $R_{3b}$ is selected from the group consisting of hydrogen, alkyl, alkoxy, halogen, hydroxy, cyano, and thioalkoxy;

$R_4$ and $R_5$ are each independently selected from the group consisting of alkyl, haloalkyl, hydroxyalkyl, alkoxyalkyl, cycloalkyl, cycloalkylalkyl, and $(NR_AR_B)$alkyl, or $R_4$ and $R_5$ taken together with the nitrogen atom to which each is attached form a non-aromatic ring of the formula:

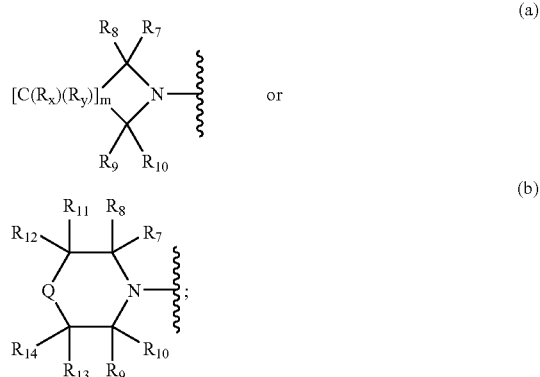

$R_7$, $R_8$, $R_9$, and $R_{10}$ at each occurrence are each independently selected from the group consisting of hydrogen, hydroxyalkyl, fluoroalkyl, and alkyl; or one of the pair $R_7$ and $R_8$ or the pair $R_9$ and $R_{10}$ is taken together to form a $C_3$–$C_6$ ring, wherein 0, 1, or 2 heteroatoms selected from O, N, or S replace a carbon atom in the ring;

$R_{11}$, $R_{12}$, $R_{13}$, and $R_{14}$ are each independently selected from the group consisting of hydrogen, hydroxy, hydroxyalkyl, alkyl, and fluoro;

$R_{6a}$ and $R_{6b}$ are each independently selected from the group consisting of a 5- to 6-membered heteroaryl, a 6-membered aryl, and a 5- to 6-membered heterocycle;

Q is selected from the group consisting of a bond, O, S, and $NR_{15}$;

L is $—[C(R_{16})(R_{17})]_k—$ or $—[C(R_{16})(R_{17})]_pO—$;

$L_2$ is selected from the group consisting of a bond, —O—, —C(=O)—, —S—, $—[C(R_{18})(R_{19})]_q—$, $—O—[C(R_{18})(R_{19})]_q—$, —NH— and —N(alkyl)-;

$L_3$ is selected from the group consisting of a bond, $—[C(R_{16})(R_{17})]_rO—$, —O—, —C(=O)—, —S—, $—[C(R_{18})(R_{19})]_q—$, $—O—[C(R_{18})(R_{19})]_q—$, —NH— and —N(alkyl)-;

$R_{15}$ is selected from the group consisting of hydrogen, alkyl, acyl, alkoxycarbonyl, amido, and formyl;

$R_{16}$ and $R_{17}$ at each occurrence are independently selected from the group consisting of hydrogen, alkyl, alkoxy, and fluoro;

$R_{18}$ and $R_{19}$ at each occurrence are each independently selected from the group consisting of hydrogen, hydroxy, alkyl, alkoxy, and fluoro;

$R_x$ and $R_y$ at each occurrence are independently selected from the group consisting of hydrogen, hydroxy, alkyl, alkoxy, alkylamino, dialkylamino, and fluoro, or one of $R_x$ or $R_y$ represents a covalent bond when taken together with $R_x$ or $R_y$ on an adjacent carbon atom such that a double bond is represented between the adjacent carbon atoms;

k is an integer from 1 to 6;

m is an integer from 1 to 5;

p is an integer from 2 to 6;

q is an integer from 1 to 4; and r is an integer from 1 to 2;

wherein 1 or 2 of X, X', Y, Y', Z, and Z' can be nitrogen; provided that $R_3$ is absent when X' is N; $R_{3a}$ is absent when Z is N; $R_2$ is absent when Z' is N, and $R_{3b}$ is absent when X is N.

Another aspect of the invention relates to pharmaceutical compositions comprising compounds of the invention. Such compositions can be administered in accordance with a method of the invention, typically as part of a therapeutic regimen for treatment or prevention of conditions and disorders related to $H_3$ receptor activity.

Yet another aspect of the invention relates to a method of selectively modulating $H_3$ receptor activity. The method is useful for treating and/or preventing conditions and disorders related to $H_3$ receptor modulation in mammals. More particularly, the method is useful for conditions and disorders related to memory and cognition processes, neurological processes, cardiovascular function, and body weight.

Processes for making compounds of the invention also are contemplated.

The compounds, compositions comprising the compounds, methods for making the compounds, and methods for treating or preventing conditions and disorders by administering the compounds are further described herein.

DETAILED DESCRIPTION OF THE INVENTION

Definition of Terms

Certain terms as used in the specification are intended to refer to the following definitions, as detailed below.

The term "acyl" as used herein, means an alkyl group, as defined herein, appended to the parent molecular moiety through a carbonyl group, as defined herein. Representative examples of acyl include, but are not limited to, acetyl, 1-oxopropyl, 2,2-dimethyl-1-oxopropyl, 1-oxobutyl, and 1-oxopentyl.

The term "acyloxy" as used herein, means an acyl group, as defined herein, appended to the parent molecular moiety through an oxygen atom. Representative examples of acyloxy include, but are not limited to, acetyloxy, propionyloxy, and isobutyryloxy.

The term "alkenyl" as used herein, means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkoxy" as used herein, means an alkoxy group, as defined herein, appended to the parent molecular moiety through another alkoxy group, as defined herein. Representative examples of alkoxyalkoxy include, but are not limited to, tert-butoxymethoxy, 2-ethoxyethoxy, 2-methoxyethoxy, and methoxymethoxy.

The term "alkoxyalkyl" as used herein, means an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkoxycarbonyl" as used herein, means an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkoxyimino" as used herein, means an alkoxy group, as defined herein, appended to the parent molecular moiety through an imino group, as defined herein. Representative examples of alkoxyimino include, but are not limited to, ethoxy(imino)methyl and methoxy(imino)methyl.

The term "alkoxysulfonyl" as used herein, means an alkoxy group, as defined herein, appended to the parent molecular moiety through a sulfonyl group, as defined herein. Representative examples of alkoxysulfonyl include, but are not limited to, methoxysulfonyl, ethoxysulfonyl, and propoxysulfonyl.

The term "alkyl" as used herein, means a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylamino" as used herein, means an alkyl group, as defined herein, appended to the parent molecular moiety through a NH group. Representative examples of alkylamino include, but are not limited to, methylamino, ethylamino, isopropylamino, and butylamino.

The term "alkylcarbonyl" as used herein, means an alkyl group, as defined herein, appended to the parent molecular moiety through a carbonyl group, as defined herein. Representative examples of alkylcarbonyl include, but are not limited to, methylcarbonyl, ethylcarbonyl, isopropylcarbonyl, n-propylcarbonyl, and the like.

The term "alkylsulfonyl" as used herein, means an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkynyl" as used herein, means a straight or branched chain hydrocarbon group containing from 2 to 10 carbon atoms and containing at least one carbon-carbon triple bond. Representative examples of alkynyl include, but are not limited to, acetylenyl, 1-propynyl, 2-propynyl, 3-butynyl, 2-pentynyl, and 1-butynyl.

The term "amido" as used herein, means an amino, alkylamino, or dialkylamino group appended to the parent molecular moiety through a carbonyl group, as defined herein. Representative examples of amido include, but are not limited to, aminocarbonyl, methylaminocarbonyl, dimethylaminocarbonyl, and ethylmethylaminocarbonyl.

The term "amino" as used herein, means a —NH$_2$ group.

The term "aryl" as used herein, means a monocyclic aromatic ring system. Representative examples of aryl include, but are not limited to, phenyl.

The aryl groups of this invention are substituted with 0, 1, 2, 3, 4, or 5 substituents independently selected from acyl, acyloxy, alkenyl, alkoxy, alkoxyalkoxy, alkoxyalkyl, alkoxycarbonyl, alkoxyimino, alkoxysulfonyl, alkyl, alkylcarbonyl, alkylsulfonyl, alkynyl, amido, carboxy, cyano, cycloalkylcarbonyl, formyl, haloalkoxy, haloalkyl, halogen, hydroxy, hydroxyalkyl, mercapto, nitro, thioalkoxy, NR$_A$R$_B$, and (NR$_A$R$_B$)sulfonyl.

The term "arylalkoxy" as used herein, means an aryl group, as defined herein, appended to the parent molecular moiety through an alkoxy group, as defined herein. Representative examples of arylalkoxy include, but are not limited to, 2-phenylethoxy, 3-naphth-2-ylpropoxy, and 5-phenylpentyloxy.

The term "arylalkoxycarbonyl" as used herein, means an arylalkoxy group, as defined herein, appended to the parent molecular moiety through a carbonyl group, as defined herein. Representative examples of arylalkoxycarbonyl include, but are not limited to, benzyloxycarbonyl.

The term "arylalkyl" as used herein, means an aryl group, as defined herein, appended to the parent molecular moiety through an alkyl group, as defined herein. Representative examples of arylalkyl include, but are not limited to, benzyl, 2-phenylethyl and 3-phenylpropyl.

The term "carbonyl" as used herein, means a —C(=O)— group.

The term "carboxy" as used herein, means a —CO$_2$H group, which may be protected as an ester group —CO$_2$-alkyl.

The term "cyano" as used herein, means a —CN group.

The term "cycloalkenyl" as used herein, means a cyclic hydrocarbon containing from 3 to 8 carbons and containing at least one carbon-carbon double bond formed by the removal of two hydrogens. Representative examples of cycloalkenyl include, but are not limited to, 2-cyclohexen-1-yl, 3-cyclohexen-1-yl, 2,4-cyclohexadien-1-yl and 3-cyclopenten-1-yl.

The term "cycloalkyl" as used herein, means a saturated cyclic hydrocarbon group containing from 3 to 8 carbons. Examples of cycloalkyl include cyclopropyl, cyclobutyl, cyclopentyl, cyclohexyl, cycloheptyl, and cyclooctyl.

The cycoalkyl groups of the invention are substituted with 0, 1, 2, 3, or 4 substituents selected from acyl, acyloxy, alkenyl, alkoxy, alkoxyalkoxy, alkoxyalkyl, alkoxycarbonyl, alkoxyimino, alkyl, alkynyl, amido, carboxy, cyano, ethylenedioxy, formyl, haloalkoxy, haloalkyl, halogen, hydroxy, hydroxyalkyl, methylenedioxy, thioalkoxy, and —NR$_A$R$_B$.

The term "cycloalkylalkyl" as used herein, means a cycloalkyl group, as defined herein, appended to the parent molecular moiety through an alkyl group, as defined herein. Representative examples of cycloalkylalkyl include, but are not limited to, cyclopropylmethyl, 2-cyclobutylethyl, cyclopentylmethyl, cyclohexylmethyl, and 4-cycloheptylbutyl.

The term "cycloalkylcarbonyl" as used herein, means a cycloalkyl group, as defined herein, appended to the parent molecular moiety through a carbonyl group, as defined herein. Representative examples of cycloalkylcarbonyl include, but are not limited to, cyclopropylcarbonyl, cyclopentylcarbonyl, cyclohexylcarbonyl, and cycloheptylcarbonyl.

The term "dialkylamino" as used herein, means two independent alkyl groups, as defined herein, appended to the parent molecular moiety through a nitrogen atom. Representative examples of dialkylamino include, but are not limited to, dimethylamino, diethylamino, ethylmethylamino, butylmethylamino.

The term "ethylenedioxy" as used herein, means a —O(CH$_2$)$_2$O— group wherein the oxygen atoms of the ethylenedioxy group are attached to the parent molecular moiety through one carbon atom forming a five-membered ring or the oxygen atoms of the ethylenedioxy group are attached to the parent molecular moiety through two adjacent carbon atoms forming a six-membered ring.

The term "fluoro" as used herein means —F.

The term "fluoroalkyl" as used herein, means at least one fluoro group, as defined herein, appended to the parent molecular moiety through an alkyl group, as defined herein. Representative example of fluoroalkyl include, but are not limited to, fluoromethyl, difluoromethyl, trifluoromethyl, pentafluoroethyl, and 2,2,2-trifluoroethyl.

The term "formyl" as used herein, means a —C(O)H group.

The term "halo" or "halogen" as used herein, means Cl, Br, I, or F.

The term "haloalkoxy" as used herein, means at least one halogen, as defined herein, appended to the parent molecular moiety through an alkoxy group, as defined herein. Representative examples of haloalkoxy include, but are not limited to, chloromethoxy, 2-fluoroethoxy, trifluoromethoxy, and pentafluoroethoxy.

The term "haloalkyl" as used herein, means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heteroaryl," as used herein, refers to an aromatic five- or six-membered ring wherein 1, 2, 3, or 4 heteroatoms are independently selected from nitrogen, oxygen, or sulfur, or a tautomer thereof. Examples of such rings include, but are not limited to, a ring wherein one carbon is replaced with an O or S atom; one, two, or three N atoms arranged in a suitable manner to provide an aromatic ring, or a ring wherein two carbon atoms in the ring are replaced with one O or S atom and one N atom. The heteroaryl groups are connected to the parent molecular moiety, to an adjoining aryl, heteroaryl, or heterocycle group, or to L$_2$ or L$_3$, wherein L$_2$ and L$_3$ are defined in formula (I), through a carbon or nitrogen atom. Representative examples of heteroaryl include, but are not limited to, furyl, imidazolyl, isoxazolyl, isothiazolyl, oxadiazolyl, oxazolyl, pyrazinyl, pyrazolyl, pyridazinyl, pyridazinonyl, pyridinyl, pyridinonyl, pyrimidinyl, pyrrolyl, tetrazolyl, thiadiazolyl, thiazolyl, thienyl or thiophenyl, triazinyl, and triazolyl.

The heteroaryl groups of the invention are substituted with 0, 1, 2, 3, or 4 substituents independently selected from acyl, acyloxy, alkenyl, alkoxy, alkoxyalkoxy, alkoxyalkyl, alkoxycarbonyl, alkoxyimino, alkoxysulfonyl, alkyl, alkylcarbonyl, alkylsulfonyl, alkynyl, amido, carboxy, cyano, formyl, haloalkoxy, haloalkyl, halogen, hydroxy, hydroxyalkyl, mercapto, nitro, thioalkoxy, —NR$_A$R$_B$, (NR$_A$R$_B$)carbonyl, and (NR$_A$R$_B$)sulfonyl.

The term "heterocycle," as used herein, refers to a four-, five-, six-, seven-, or eight-membered ring containing one, two, or three heteroatoms independently selected from the group consisting of nitrogen, oxygen, and sulfur. Rings containing at least four members can be saturated or unsaturated. For example, the four- and five-membered ring has zero or one double bond. The six-membered ring has zero, one, or two double bonds. The seven- and eight-membered rings have zero, one, two, or three double bonds. The heterocycle groups of the invention can be attached to the parent molecular moiety, to an adjoining aryl, heteroaryl, or heterocycle group, or to $L_2$ or $L_3$, wherein $L_2$ and $L_3$ are defined in formula (I), through a carbon atom or a nitrogen atom. Representative examples of nitrogen-containing heterocycles include, but are not limited to, azepanyl, azetidinyl, aziridinyl, azocanyl, morpholinyl, piperazinyl, piperidinyl, pyrrolidinyl, pyrrolinyl, dihydrothiazolyl, and thiomorpholinyl. Representative examples of non-nitrogen containing heterocycles include, but are not limited to, tetrahydrofuryl and tetrahydropyranyl.

The heterocycles of the invention are substituted with 0, 1, 2, 3, or 4 substituents independently selected from acyl, acyloxy, alkenyl, alkoxy, alkoxyalkoxy, alkoxyalkyl, alkoxycarbonyl, alkoxyimino, alkoxysulfonyl, alkyl, alkylsulfonyl, alkynyl, amido, arylalkyl, arylalkoxycarbonyl, carboxy, cyano, formyl, haloalkoxy, haloalkyl, halogen, hydroxy, hydroxyalkyl, mercapto, nitro, oxo, thioalkoxy, —$NR_AR_B$, and $(NR_AR_B)$sulfonyl.

The term "hydroxy" as used herein means a —OH group.

The term "hydroxyalkyl" as used herein, means at least one hydroxy group, as defined herein, appended to the parent molecular moiety through an alkyl group, as defined herein. Representative examples of hydroxyalkyl include, but are not limited to, hydroxymethyl, 2-hydroxyethyl, 2-methyl-2-hydroxyethyl, 3-hydroxypropyl, 2,3-dihydroxypentyl, and 2-ethyl-4-hydroxyheptyl.

The term "hydroxy-protecting group" means a substituent which protects hydroxyl groups against undesirable reactions during synthetic procedures. Examples of hydroxy-protecting groups include, but are not limited to, methoxymethyl, benzyloxymethyl, 2-methoxyethoxymethyl, 2-(trimethylsilyl)ethoxymethyl, benzyl, triphenylmethyl, 2,2,2-trichloroethyl, t-butyl, trimethylsilyl, t-butyldimethylsilyl, t-butyldiphenylsilyl, methylene acetal, acetonide benzylidene acetal, cyclic ortho esters, methoxymethylene, cyclic carbonates, and cyclic boronates. Hydroxy-protecting groups are appended onto hydroxy groups by reaction of the compound that contains the hydroxy group with a base, such as triethylamine, and a reagent selected from an alkyl halide, alkyl triflate, trialkylsilyl halide, trialkylsilyl triflate, aryldialkylsilyltriflate, or an alkylchloroformate, $CH_2I_2$, or a dihaloboronate ester, for example with methyliodide, benzyl iodide, triethylsilyltriflate, acetyl chloride, benzylchloride, or dimethylcarbonate. A protecting group also may be appended onto a hydroxy group by reaction of the compound that contains the hydroxy group with acid and an alkyl acetal.

The term "imino" as defined herein means a —C(=NH)— group.

The term "mercapto" as used herein, means a —SH group.

The term "methylenedioxy" as used herein, means a —$OCH_2O$— group wherein the oxygen atoms of the methylenedioxy are attached to the parent molecular moiety through two adjacent carbon atoms.

The term "—$NR_AR_B$" as used herein, means two groups, $R_A$ and $R_B$, which are appended to the parent molecular moiety through a nitrogen atom. $R_A$ and $R_B$ are independently selected from hydrogen, alkyl, acyl and formyl. Representative examples of —$NR_AR_B$ include, but are not limited to, amino, dimethylamino, methylamino, acetylamino, and acetylmethylamino.

The term "$(NR_AR_B)$alkyl" as used herein, means an —$NR_AR_B$ group, as defined herein, appended to the parent molecular moiety through an alkyl group, as defined herein. Representative examples of $(NR_AR_B)$alkyl include, but are not limited to, 2-(methylamino)ethyl, 2-(dimethylamino)ethyl, 2-(amino)ethyl, 2-(ethylmethylamino)ethyl, and the like.

The term "$(NR_AR_B)$carbonyl" as used herein, means an —$NR_AR_B$ group, as defined herein, appended to the parent molecular moiety through a carbonyl group, as defined herein. Representative examples of $NR_ARB)$carbonyl include, but are not limited to, aminocarbonyl, (methylamino)carbonyl, (dimethylamino)carbonyl, (ethylmethylamino)carbonyl, and the like.

The term "$(NR_AR_B)$sulfonyl" as used herein, means a —$NR_AR_B$ group, as defined herein, appended to the parent molecular moiety through a sulfonyl group, as defined herein. Representative examples of $(NR_AR_B)$sulfonyl include, but are not limited to, aminosulfonyl, (methylamino)sulfonyl, (dimethylamino)sulfonyl and (ethylmethylamino)sulfonyl.

The term "nitro" as used herein means a —$NO_2$ group.

The term "nitrogen protecting group" as used herein, means those groups intended to protect a nitrogen atom against undesirable reactions during synthetic procedures. Nitrogen protecting groups comprise carbamates, amides, N-benzyl derivatives, and imine derivatives. Preferred nitrogen protecting groups are acetyl, benzoyl, benzyl, benzyloxycarbonyl (Cbz), formyl, phenylsulfonyl, pivaloyl, tert-butoxycarbonyl (Boc), tert-butylacetyl, trifluoroacetyl, and triphenylmethyl (trityl). Nitrogen-protecting groups are appended onto primary or secondary amino groups by reacting the compound that contains the amine group with base, such as triethylamine, and a reagent selected from an alkyl halide, an alkyl triflate, a dialkyl anhydride, for example as represented by (alkyl-O)$_2$C=O, a diaryl anhydride, for example as represented by (aryl-O)$_2$C=O, an acyl halide, an alkylchloroformate, or an alkylsulfonylhalide, an arylsulfonylhalide, or halo-CON(alkyl)$_2$, for example acetylchloride, benzoylchloride, benzylbromide, benzyloxycarbonylchloride, formylfluoride, phenylsulfonylchloride, pivaloylchloride, (tert-butyl-O—C=O)$_2$O, trifluoroacetic anhydride, and triphenylmethylchloride.

The term "oxo" as used herein means (=O).

The term "sulfonyl" as used herein means a —$S(O)_2$— group.

The term "thioalkoxy" as used herein means an alkyl group, as defined herein, appended to the parent molecular moiety through a sulfur atom. Representative examples of thioalkoxy include, but are no limited to, methylthio, ethylthio, and propylthio.

The term "4- to 8-membered non-aromatic ring" as used herein means a monocyclic cycloalkyl group as described herein containing 4 to 8 carbons or a 4- to 8-membered heterocycle as described herein.

As used herein, the term "antagonist" encompasses and describes compounds that prevent receptor activation by an $H_3$ receptor agonist alone, such as histamine, and also encompasses compounds known as "inverse agonists". Inverse agonists are compounds that not only prevent receptor activation by an $H_3$ receptor agonist, such as histamine, but also inhibit intrinsic $H_3$ receptor activity.

Compounds of the Invention

Compounds of the invention can have the general formula (I) as described above.

The invention also includes compounds having the formula (I) wherein Y and Y' are CH; X, X', and Z' are C; $R_2$, $R_3$, and $R_{3b}$ are hydrogen; Z is N; and $R_{3a}$ is absent.

In another embodiment, compounds of the invention can have formula (I) wherein Y is CH; X, X', Z, and Z' are C; $R_2$, $R_3$, $R_{3a}$, and $R_{3b}$ are hydrogen; and Y' is N.

In yet another embodiment, compounds of the invention have formula (I) wherein Y and Y' are CH; X and Z' are C; $R_2$ and $R_{3b}$ are hydrogen; X' is N; Z is N; and $R_3$ and $R_{3a}$ are absent.

Yet another embodiment relates to compounds of the invention having the formula (I) wherein X, X', Z, and Z' are C; $R_2$, $R_3$, $R_{3a}$, and $R_{3b}$ are hydrogen; Y is N; and Y' is N.

Still yet another embodiment relates to compounds of the invention having the formula (I) wherein Y' is CH; X, X', and Z are C; $R_3$, $R_{3a}$, and $R_{3b}$ are hydrogen; Y is N; Z' is N; and $R_2$ is absent.

Another embodiment relates to compounds of the invention having the formula (I) wherein Y' is CH; X, Z, and Z' are C; $R_2$, $R_{3a}$, and $R_{3b}$ are hydrogen; Y is N; X' is N; and $R_3$ is absent.

Still yet another embodiment relates to compounds of the invention having the formula (I) wherein Y' is CH; X, X', and Z' are C; $R_2$, $R_3$, and $R_{3b}$ are hydrogen; Y is N; Z is N; and $R_{3a}$ is absent.

Still yet another embodiment relates to compounds of the invention having the formula (I) wherein Y is CH; X, X', and Z are C; $R_3$, $R_{3a}$, and $R_{3b}$ are hydrogen; Y' is N; Z' is N; and $R_2$ is absent.

Still yet another embodiment relates to compounds of the invention having the formula (I) wherein Y and Y' are CH; Z' and Z are C; $R_2$ and $R_{3a}$ are hydrogen; X' is N; X is N; and $R_3$ and $R_{3b}$ are absent.

Compounds of the invention also can have the formula (I) wherein Y' is CH; X, X', Z and Z' are C; $R_2$, $R_3$, $R_{3a}$, and $R_{3b}$ are hydrogen; and Y is N.

In yet another embodiment, compounds of the invention have formula (I) wherein Y and Y' are CH; X' and Z' are C; $R_2$ and $R_3$ are hydrogen; X is N; Z is N; and $R_{3a}$ and $R_{3b}$ are absent.

Still yet another embodiment relates to compounds of the invention having the formula (I) wherein Y is CH; X, Z', and Z are C; $R_2$, $R_{3a}$, and $R_{3b}$ are hydrogen; Y' is N; X' is N; and $R_3$ is absent.

Preferred compounds of the invention are those compounds of formula (I) wherein Y' is CH; X, X', Z and Z' are C; $R_2$, $R_3$, $R_{3a}$, and $R_{3b}$ are hydrogen; and Y is N.

$R_1$ is group of the formula -$L_2$-$R_{6a}$-$L_3$-$R_{6b}$ wherein $L_2$, $L_3$, $R_{6a}$, and $R_{6b}$ are as defined for compounds of formula (I). More preferably, $L_2$ is a bond, $L_3$ is a bond, —[C($R_{16}$)($R_{17}$)]$_r$—O—, —O—, —C(=O)—, —S—, —[C($R_{18}$)($R_{19}$)]$_q$—, —O—[C($R_{18}$)($R_{19}$)]$_q$—, —NH— or —N(alkyl)-, wherein $R_{16}$, $R_{17}$, $R_{18}$, $R_{19}$, r, and q are as defined for compounds of formula (I); and $R_{6a}$ and $R_{6b}$ are each independently selected from a 5- or 6-membered heteroaryl ring, phenyl, and a non-aromatic 4- to 8-membered ring. Preferably, at least one of $R_{6a}$ and $R_{6b}$ is a 5- or 6-membered heteroaryl ring. More preferably, $R_{6a}$ is a 5- or 6-membered heteroaryl ring and $R_{6b}$ is a 5- or 6-membered heterocycle.

More specifically, $R_{6a}$ and $R_{6b}$ are each independently selected from the group consisting of isoxazolyl, morpholinyl, phenyl, pyridazinyl, pyridinyl, pyrimidinyl, pyrazinyl, pyrazolyl, thiadiazolyl, thiazolyl, thienyl, triazolyl and cyclobutanyl. In preferred compounds of the invention, $R_{6a}$ is selected from the group consisting of isoxazolyl, phenyl, pyrimidinyl, pyrazolyl, thiazolyl, thienyl, triazolyl, and cyclobutanyl; and $R_{6b}$ is selected from the group consisting of isoxazolyl, morpholinyl, phenyl, pyridazinyl, pyridinyl, pyrazinyl, pyrazolyl, thiadiazolyl, thiazolyl, and thienyl.

L can be —[C($R_{16}$)($R_{17}$)]$_n$— or —[C($R_{16}$)($R_{17}$)]$_p$O— as defined for compounds of formula (I). Preferably L is —CH$_2$CH$_2$—.

Preferably, $R_4$ and $R_5$ are taken together with the nitrogen atom to which each is attached form a 4- to 8-membered non-aromatic ring represented by formula (a). The preferred compounds of the invention are those wherein at least one substituent represented by $R_7$, $R_8$, $R_9$, and $R_{10}$ is selected from the group consisting of alkyl, halogen, fluoroalkyl, and hydroxyalkyl or at least one substituent represented by $R_x$ or $R_y$ is selected from the group consisting of hydrogen, hydroxy, and fluoro. More preferably, $R_4$ and $R_5$ taken together with the nitrogen atom to which each is attached to form 2-methylpyrrolidine and, more specifically, (2R)-methylpyrrolidine.

Specific compounds contemplated as part of the invention include, but are not limited to:

6-{2-[(2R)-2-methylpyrrolidin-1-yl]ethyl}-2-(4-methyl-2-thien-2-yl-1,3-thiazol-5-yl)quinoline;

6-[2-((2R)-2-methyl-pyrrolidin-1-yl)-ethyl]-2-[2-(4-methyl-[1,2,3]thiadiazol-5-yl-thiazol-4-yl]-quinoline;

2-(4-methyl-2-pyrazin-2-yl-thiazol-5-yl)-6-[2-((2R)-2-methyl-pyrrolidin-1-yl)-ethyl]-quinoline;

2-[1-(3,4-dichloro-phenyl)-5-methyl-1H-pyrazol-4-yl]-6-[2-((2R)-2-methyl-pyrrolidin-1-yl)-ethyl]-quinoline;

2-[2-(4-chloro-phenoxymethyl)-thiazol-4-yl]-6-[2-((2R)-2-methyl-pyrrolidin-1-yl)-ethyl]-quinoline;

2-(5-methyl-1-pyridin-2-yl-1H-pyrazol-4-yl)-6-[2-((2R)-2-methyl-pyrrolidin-1-yl)-ethyl]-quinoline;

2-[5-methyl-1-(6-methyl-4-trifluoromethyl-pyridin-2-yl)-1H-pyrazol-4-yl]-6-[2-((2R)-2-methyl-pyrrolidin-1-yl)-ethyl]-quinoline;

2-[3-(4-chloro-phenyl)-isoxazol-5-yl]-6-[2-((2R)-2-methyl-pyrrolidin-1-yl)-ethyl]-quinoline;

6-[2-(2R)-2-methyl-pyrrolidin-1-yl)-ethyl]-2-[5-(1-methyl-5-trifluoromethyl-1H-pyrazol-3-yl)-thiophen-2-yl]-quinoline;

2-(4-methyl-2-morpholin-4-yl-thiazol-5-yl)-6-[2-((2R)-2-methyl-pyrrolidin-1-yl)-ethyl]-quinoline;

6-[2-((2R)-2-methyl-pyrrolidin-1-yl)-ethyl]-2-(2-phenyl-thiazol-5-yl)-quinoline;

2-(4-methyl-2-pyridin-2-yl-thiazol-5-yl)-6-[2-((2R)-2-methyl-pyrrolidin-1-yl)-ethyl]-quinoline;

2-[3-(3-chloro-5-trifluoromethyl-pyridin-2-yl)-isoxazol-5-yl]-6-[2-((2R)-2-methyl-pyrrolidin-1-yl)-ethyl]-quinoline;

2-(4-methyl-2-pyridin-3-yl-thiazol-5-yl)-6-[2-((2R)-2-methyl-pyrrolidin-1-yl)-ethyl]-quinoline;

2-(4-methyl-2-pyridin-4-yl-thiazol-5-yl)-6-[2-((2R)-2-methyl-pyrrolidin-1-yl)-ethyl]-quinoline;

6-[2-((2R)-2-methyl-pyrrolidin-1-yl)-ethyl]-2-(2-phenyl-thiazol-4-yl)-quinoline;

2-[3-(4-chloro-phenyl)-5-methyl-isoxazol-4-yl]-6-[2-((2R)-2-methyl-pyrrolidin-1-yl)-ethyl]-quinoline;

1-(4-{6-[2-((2R)-2-methyl-pyrrolidin-1-yl)-ethyl]-quinolin-2-yl}-phenyl)-1H-pyridin-4-one;

6-[2-((2R)-2-methyl-pyrrolidin-1-yl)-ethyl]-2-(4-piperidin-1-yl-phenyl)-quinoline;

2-(5'-methyl-[2,2']bithiophenyl-5-yl)-6-[2-((2R)-2-methyl-pyrrolidin-1-yl)-ethyl]-quinoline;

2-(6-methyl-2-phenyl-pyrimidin-4-yl)-6-[2-((2R)-2-methyl-pyrrolidin-1-yl)-ethyl]-quinoline;

2-(5-chloro-1-methyl-3-phenyl-1H-pyrazol-4-yl)-6-[2-((2R)-2-methyl-pyrrolidin-1-yl)-ethyl]-quinoline;

6-[2-((2R)-2-methyl-pyrrolidin-1-yl)-ethyl]-2-(1-pyridin-3-yl-cyclobutyl)-quinoline;

2-methyl-3-[1-(5-methyl-isoxazol-3-yl)-1H-[1,2,4]triazol-3-yl]-6-[2-((2R)-2-methyl-pyrrolidin-1-yl)-ethyl]-quinoline;

2-[1-(2,4-difluoro-phenyl)-5-methyl-1H-[1,2,3]triazol-4-yl]-6-{2-[(2R)-2-methyl-pyrrolidin-1-yl]-ethyl}-quinoline;

2-[1-(6-ethoxy-pyridazin-3-yl)-5-methyl-1H-pyrazol-4-yl]-6-{2-[(2R)-2-methyl-pyrrolidin-1-yl]-ethyl}-quinoline;

2-(2'-methyl-[2,4']bithiazolyl-4-yl)-6-{2-[(2R)-2-methyl-pyrrolidin-1-yl]-ethyl}-quinoline;

2-[2-(5-methyl-isoxazol-3-yl)-thiazol-4-yl]-6-{2-[(2R)-2-methyl-pyrrolidin-1-yl]-ethyl}-quinoline;

2-[2-(2,6-dichloro-pyridin-4-yl)-thiazol-4-yl]-6-{2-[(2R)-2-methyl-pyrrolidin-1-yl]-ethyl}-quinoline;

6-{2-[(2R)-2-methyl-pyrrolidin-1-yl]-ethyl}-2-{2-[6-(2,2,2-trifluoro-ethoxy)-pyridin-3-yl]-thiazol-4-yl}-quinoline;

2-[2-(4-chloro-phenyl)-4-methyl-thiazol-5-yl]-6-{2-[(2R)-2-methyl-pyrrolidin-1-yl]-ethyl}-quinoline;

2-(5-methyl-3-phenyl-isoxazol-4-yl)-6-{2-[(2R)-2-methyl-pyrrolidin-1-yl]-ethyl}-quinoline;

6-{2-[(2R)-2-methyl-pyrrolidin-1-yl]-ethyl}-2-(3-phenyl-isoxazol-5-yl)-quinoline;

2-[4-(4,5-dichloro-imidazol-1-yl)-phenyl]-6-{2-[(2R)-2-methyl-pyrrolidin-1-yl]-ethyl}-quinoline;

6-{2-[(2R)-2-methyl-pyrrolidin-1-yl]-ethyl}-2-(4-methyl-2-pyrrolidin-1-yl-pyrimidin-5-yl)-quinoline; and 6-{2-[(2R)-2-(methyl-d)-pyrrolidin-5,5-d2-1-yl]-ethyl}-2-(4-methyl-2-pyrrolidin-1-yl-pyrimidin-5-yl)-quinoline.

Compounds of the invention may exist as stereoisomers wherein, asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, Pure Appl. Chem., 1976, 45: 13–30. The invention contemplates various stereoisomers and mixtures thereof and these are specifically included within the scope of this invention. Stereoisomers include enantiomers and diastereomers, and mixtures of enantiomers or diastereomers. Individual stereoisomers of compounds of the invention may be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry", 5th edition (1989), Longman Scientific & Technical, Essex CM20 2 JE, England, or (2) direct separation of the mixture of optical enantiomers on chiral chromatographic columns or (3) fractional recrystallization methods.

Methods for Preparing Compounds of the Invention

The compounds of the invention can be better understood in connection with the following synthetic schemes and methods which illustrate a means by which the compounds can be prepared.

Abbreviations which have been used in the descriptions of the schemes and the examples that follow are: Ac for acetyl; atm for atmosphere(s); BINAP for 2,2'-bis(diphenylphosphino)-1,1'-binaphthyl; Boc for butyloxycarbonyl; Bu for butyl; dba for dibenzylidene acetone; DCM for dichloromethane; DMAP for 4-(N,N-dimethylamino)pyridine; DMF for N,N-dimethylformamide; DMSO for dimethylsulfoxide; dppf for 1,1'-bis(diphenylphosphino)ferrocene; Et for ethyl; EtOH for ethanol; EtOAc for ethyl acetate; HPLC for high pressure liquid chromatography; IPA for isopropyl alcohol; IPAC or IPAc for isopropyl acetate; LDA for lithium diisopropylamide; NBS for N-bromosuccinimide; NIS for N-iodosuccinimide; Me for methyl; MeOH for methanol; Ms for methanesulfonyl; MTBE for tert-butyl methyl ether; Pd for palladium; tBu for tert-butyl; TBDMSCl for t-butyldimethylsilyl chloride; TBDMSO for t-butyldimethylsilyl-O; TEA for triethylamine; TFA for trifluoroacetic acid; TfO for $CF_3S(O)_3$—; THF for tetrahydrofuran; and Ts for p-MePhS(O)$_2$—.

The compounds of this invention can be prepared by a variety of synthetic procedures. Representative procedures are shown in, but are not limited to, Schemes 1–27.

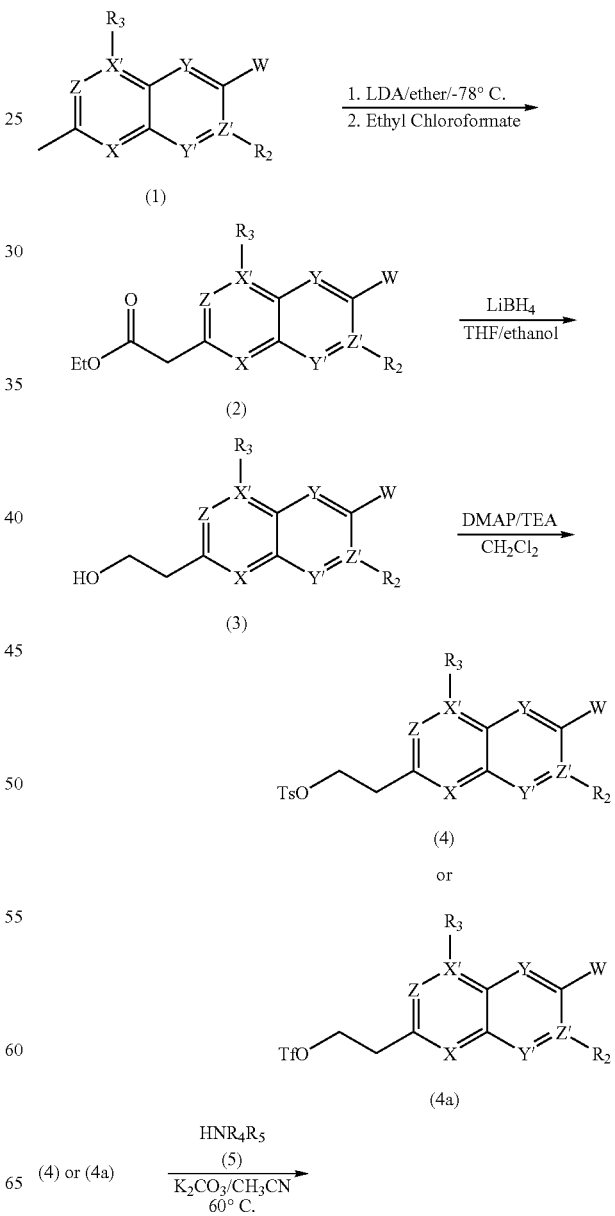

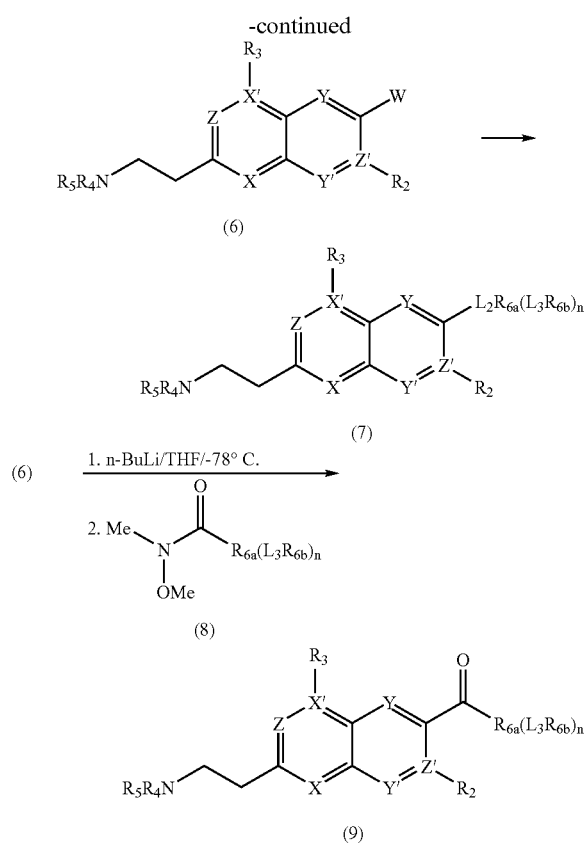

Compounds of formulas (7) and (9), wherein n is 0 or 1, and wherein X, X', Y, Y', Z, Z', $R_2$, $R_3$, $R_4$, $R_5$, $L_2$, $L_3$, $R_{6a}$, $R_{6b}$, are as defined in formula (I), can be prepared as described in Scheme 1. Compounds of formula (1), wherein W is OH, Br, Cl, or 1, purchased or prepared using methodology known to those of ordinary skill in the art, can be treated with lithium diisopropylamine and a chloroformate such as, but not limited to, ethyl chloroformate to provide esters of formula (2). Esters of formula (2) can be treated with a reducing agent such as, but not limited to, lithium borohydride to provide alcohols of formula (3). Alcohols of formula (3) wherein W is Br, Cl, or I can be treated with a base such as, but not limited to, triethylamine and a sulfonating agent such as, but not limited to, methanesulfonyl chloride or p-toluensulfonyl chloride to provide sulfonates of formula (4). Compounds of formula (3) wherein W is —OH can be converted to compounds of formula (4a) wherein W is triflate by reaction with triflic anhydride and a base such as, but not limited to, pyridine or triethylamine. Sulfonates or triflates of formula (4) or (4a) can be treated with an optional base such as, but not limited to, potassium carbonate or sodium carbonate and an amine of formula (5) with or without heat to provide amines of formula (6), wherein W is triflate, Br, Cl, or I.

The Suzuki reaction can be used to produce compounds of formula (7), wherein $L_2$ is a bond, n is 0 or 1, $R_{6a}$ is aryl or heteroaryl, and X, X', Y, Y', Z, Z', $R_2$, $R_3$, $R_4$, $R_5$, $L_3$, and $R_{6b}$ are as defined for formula (I). In such a Suzuki reaction, compounds of formula (6) wherein W is triflate, Br, Cl, or I are reacted with boronic acids of formula (14), wherein $R_{94}$ is hydrogen, a metal catalyst, a base, and optionally with a Pd ligand added. The reaction can be performed in a solvent such as, but is not limited to, tetrahydrofuran, DMF, 1,4-dioxane and the like, at a temperature from about 20° C. to about 120° C. Examples of metal catalysts include, but are not limited to, palladium diacetate, $Pd(PPh_3)_4$, $Pd_2(dba)_3$, dichloro(di-tert-butylphosphinous acid) palladium (II) dimmer, and $PdCl_2(dppf)$. Examples of bases include, but are not limited to, 0.2 M $K_3PO_4$, $Cs_2CO_3$, CsF, KF, and $Na_2CO_3$. Examples of palladium ligands include, but are not limited to, (dicyclohexylphosphinyl)biphenyl, trifurylphosphine, tris(tert-butyl) phosphine, and triphenylphosphine. Boronic acid esters of formula (14) wherein $R_{94}$ is alkyl, $L_2$ is a bond, $R_{6a}$ is aryl or heteroaryl, n is 0 or 1, and $L_3$ and $R_{6b}$ are as defined in formula (I), can be used in place of boronic acids in the aforesaid reaction. Boronic acids can be esterified to the corresponding boronic acid esters with alcohols such as methanol or with diols such as pinacol.

There are many aryl and heteroaryl boronic acids and boronic acid esters that are available commercially or that can be prepared as described in the scientific literature of synthetic organic chemistry.

Alternatively, using the Stille coupling, compounds of formula (7) wherein $L_2$ is a bond, n is 0 or 1, and X, X', Y, Y', Z, Z', $L_3$, $R_2$, $R_3$, $R_4$, $R_5$, $R_{6a}$ and $R_{6b}$ are as defined for formula (I), may be prepared from compounds of formula (6) wherein W is triflate, Cl, Br, or I, by treatment with aryl and heteroaryl stannanes of formula (13), a palladium source such as tris(dibenzylidineacetone)dipalladium (CAS # 52409-22-0) or palladium diacetate, and a ligand such as tri(2-furyl)phosphine (CAS # 5518-52-5) or triphenyl arsine in a solvent, for example in DMF at a temperature from about 25° C. to about 150° C. While many organotin reagents for the Stille coupling are commercially available or described in the literature, new organotin reagents can be prepared from arylhalides, aryltriflates, heteroarylhalides, heteroaryltriflates by reaction with distannanes like $(Me_3Sn)_2$ (hexamethyl distannane) in the presence of a palladium source like $Pd(Ph_3P)_4$. Such methods are described, for instance, in Krische, et. al., Helvetica Chimica Acta 81(11):1909–1920 (1998), and in Benaglia, et al., Tetrahedron Letters 38:4737–4740 (1997). These reagents can be reacted with (6) wherein W is triflate, Cl, Br, or I, to give (7) wherein $L_2$ is a bond, n is 0 or 1, and X, X', Y, Y', Z, Z', $R_2$, $R_3$, $R_4$, $R_5$, $L_3$, $R_{6a}$, and $R_{6b}$ are as defined in formula (I), as described under Stille conditions, or for example under the conditions reported by Littke, Schwartz, and Fu, *Journal of the American Chemical Society* 124: 6343–6348 (2002).

Alternatively, compounds of formula (7) wherein $L_2$ is a bond, n is 0 or 1, and X, X', Y, Y', Z, Z', $R_2$, $R_3$, $R_4$, $R_5$, $L_3$, $R_{6a}$, and $R_{6b}$ are as defined for formula (I), can be prepared according to the so called Negishi coupling by reaction of a compound of formula (6) wherein W is a halide or triflate, with a compound of the formula halide-zinc-$L_2R_{6a}(L_3R_{6b})_n$. The catalyst may be selected from those typically employed for the reaction (for example, tetrakis(triphenylphosphine) palladium, tetrakis(triphenylphosphine)nickel, dichlorobis (triphenylphosphine)palladium, dichlorobis(triphenylphosphine)palladium/n-butyl lithium, dichlorobis(1,1-bis (diphenyl phosphino)ferrocene)palladium and dichlorobis (1,4-bis(diphenylphosphino)butane)palladium). Suitable solvents include tetrahydrofuran, diethylether and dimethoxyethane. The reaction is typically carried out at a temperature from about 20° C. to about 160° C., usually 20° C. to 130° C. for 10 minutes to about 5 days, usually 30 minutes to about 15 hours. Alternatively, one skilled in the art will appreciate that the reactive groups of the reagents can be reversed. Thus one skilled in the art will appreciate that W in the aforesaid reaction can be the zinc halide coupled to an $(R_{6b}L_3)_nR_{6a}L_2$-halide or triflate. (Knochel, P. and Singer, R. D. *Chem. Rev.*, 93, pages 2117–2188, 1993), Compounds of formula (7) wherein $L_2$ is a bond, n is 0 or 1, $R_{6a}$ is a nitrogen-containing heteroaryl or heterocycle ring linked to the bicyclic core group through a nitrogen, and X, X', Y, Y', Z, Z', $R_2$, $R_3$, $R_4$, $R_5$, $L_3$, and $R_{6b}$ are as defined for formula (I), may be prepared by heating compounds of formula (6) wherein W is triflate or halogen, with a compound of the formula H—$R_{6a}(L_3R_{6b})_n$ wherein n is 0 or 1 and H is a hydrogen on a nitrogen atom, with a base such as, but not limited to, sodium t-butoxide or cesium carbonate, in the presence of a metal catalyst such as, but not limited to, copper metal or CuI, palladium diacetate, and also optionally with a ligand such as, but not limited to, BINAP, tri-tertbutylphosphine in a solvent such as dioxane, toluene, N,N-dimethylformamide (DMF), N,N-dimethylacetamide, N-methylpyrrolidinone (NMP) or pyridine. References that describe these methodologies may be found in the following references: J. Hartwig et al., Angew. Chem. Int. Ed. 37:2046–2067 (1998); J. P. Wolfe et al., Acc. Chem. Res., 13:805–818 (1998); M. Sugahara et al., Chem. Pharm. Bull., 45:719–721 (1997); J. P. Wolfe et al., J. Org. Chem., 65:1158–1174, (2000); F. Y. Kwong et al., Org. Lett., 4:581–584, (2002); A. Klapars et al., J. Amer. Chem. Soc., 123:7727–7729 (2001); B. H. Yang et al., J. Organomet. Chem., 576:125–146 (1999); A. Kiyomori et al., Tet. Lett., 40:2657–2640 (1999); and Hartwig, J. Org. Chem., 64(15): 5575–5580 (1999).

Compounds of formula (6) wherein W is —Br or —I, can also be treated with an organolithium reagent such as, but not limited to, n-butyllithium, sec-butyllithium or tert-butyllithium and an amide of formula (8) to provide compounds of formula (9) wherein n is 0 or 1, and X, X', Y, Y', Z, Z', $R_2$, $R_3$, $R_4$, $R_5$, $L_3$, $R_{6a}$, and $R_{6b}$ are as defined for formula (I).

Compounds of formula (6) wherein W is —Br, or —I, can also be treated with an organolithium reagent such as, but not limited to, n-butyllithium, sec-butyllithium or tert-butyllithium to provide an intermediate anion which is then reacted with an amide of formula (8) to provide compounds of formula (9) wherein X, X', Y, Y', Z, Z', $R_2$, $R_3$, $R_4$, $R_5$ and $R_6$ are as defined for formula (I). Compound (8) is prepared from the corresponding carboxylic acid of formula $R_6$—COOH via activation (with $SOCl_2$, oxalyl chloride, N,N'-carbonyl diimidazole (CDI), 1-ethyl-3-(3-dimethylaminopropyl)carbodiimide (EDCI), or EtOCCl) and subsequent reaction with N,O-dimethylhydroxylamine in the presence of a non-nucleophilic base.

Compounds of formula (7) wherein n is 0 or 1, $L_2$ is —NH— or —N(alkyl)- and X, X', Y, Y', Z, Z', $R_2$, $R_3$, $R_4$, $R_5$, $L_3$, $R_{6a}$, and $R_{6b}$ are as defined for formula (I) can be prepared by heating compounds of formula (6) wherein W is triflate or halogen, with compounds of formula $H_2N$—$R_{6a}(L_3R_{6b})_n$, or $HN(alkyl)$-$R_{6a}(L_3R_{6b})_n$, with a base such as, but not limited to sodium tert-butoxide or cesium carbonate, in the presence of a metal catalyst such as, but not limited to copper metal or CuI, palladium diacetate, and also optionally with a ligand such as, but not limited to, BINAP, tri-tertbutylphosphine in solvents such as dioxane, toluene, pyridine. References that describe these methodologies may be found in the following references: J. Hartwig, et al., Angew. Chem. Int. Ed., 37:2046–2067 (1998); J. P. Wolfe et al., Acc. Chem. Res., 13:805–818 (1998); J. P. Wolfe et al., J. Org. Chem., 65:1158–1174 (2000); F. Y. Kwong et al., Org. Lett., 4:581–584, (2002); B. H. Yang et al., J. Organomet. Chem., 576:125–146 (1999); and Hartwig, J. Org. Chem., 64(15):5575–5580 (1999).

Compounds of formula (7), wherein $L_2$ is oxygen, n is 0 or 1, and X, X', Y, Y', Z, Z', $R_2$, $R_3$, $R_4$, $R_5$, $L_3$, $R_{6a}$, and $R_{6b}$ are as defined for formula (I) can be prepared by heating compounds of formula (6) wherein W is triflate or halogen, with a compound of formula $HOR_{6a}(L_3R_{6b})_n$ wherein n is 0 or 1 and $R_{6a}$, $R_{6b}$, and $L_3$ are as defined in formula (I), using a base such as but not limited to sodium hydride in a solvent such as toluene or N,N-dimethylformamide, in the presence of a metal containing catalyst such as CuI or palladium diacetate. References that describe these methodologies may be found in the following references: J. Hartwig et al., Angew. Chem. Int. Ed., 37:2046–2067 (1998); J.-F. Marcoux et al., J. Am. Chem. Soc., 119:10539–10540 (1997); A. Aranyos et al., J. Amer. Chem. Soc., 121:4369–4378 (1999); M. Palucki et al., J. Amer. Chem. Soc., 119:3395–3396 (1997); and T. Yamamoto et al., Can. J. Chem., 61:86–91 (1983). Additional methodologies useful for the synthesis of compounds of formula (7), wherein $L_2$ is oxygen and $R_{6a}$, $R_{6b}$, and $L_3$ are as defined in formula (1) can be found in the following references: A. Aranyos et al., *J. Amer. Chem. Soc.*, 121:43694378 (1999); E. Baston et al., *Synth. Commun.*, 28:2725–2730 (1998); and A. Toshimitsu et al., *Het. Chem.*, 12:392–397 (2001).

Compounds of formula (7), wherein n is 0 or 1, $L_2$ is sulfur and X, X', Y, Y', Z, Z', $R_2$, $R_3$, $R_4$, $R_5$, $L_3$, $R_{6a}$, and $R_{6b}$, are as defined for formula (I) can be prepared by heating compounds of formula (6) wherein W is halogen with a compound of formula $HSR_{6a}(L_3R_{6b})_n$, wherein n is 0 or 1, and $R_{6a}$, $R_{6b}$, and $L_3$ are as defined for formula (I), using a base with or without a metal catalyst such as CuI or palladium diacetate, in the presence of a base in a solvent such as dimethylformamide or toluene. References that describe these methodologies may be found in the following references: G. Y. Li et al., J. Org. Chem., 66:8677–8681 (2001); G. Y. Li et al., Angew. Chem. Int. Ed., 40:1513–1516 (2001); U. Schopfer et al., Tetrahedron, 57:3069–3074 (2001); and C. Palomo et al., Tet. Lett., 41:1283–1286 (2000).

Compounds of formula (7), wherein $L_2$ is —$O[C(R_{18})(R_{19})]_q$—, n is 0 or 1, and X, X', Y, Y', Z, Z', $R_2$, $R_3$, $R_4$, $R_5$, q, $L_3$, $R_{6a}$, $R_{18}$, $R_{19}$ and $R_{6b}$ are as defined for formula (I) can be prepared by treating compounds of formula (6) wherein W is OH with a compounds of formula $HO[C(R_{18})(R_{19})]_qR_{6a}(L_3R_{6b})_n$ wherein n is 0 or 1 and $R_{6a}$, $R_{6b}$, q, $R_{18}$, $R_{19}$ and $L_3$ are as defined for formula (I), in the presence of diethyl azodicarboxylate and triphenylphosphine using the conditions of the Mitsunobu reaction which is well known to one skilled in the art of organic chemistry. Compounds of formula (6) wherein W is OH can be generated from compounds of formula (6) wherein W is Cl, Br or I as described in Mann, G.; et. al. J. Amer. Chem. Soc. 1999, 121, 3224–3225. Alternatively, compounds of formula (7), wherein $L_2$ is —$O[C(R_{18})(R_{19})]_q$—, n is 0 or 1, and X, X', Y, Y', Z, Z', $R_2$, $R_3$, $R_4$, $R_5$, q, $L_3$, $R_{6a}$, $R_{18}$, $R_{19}$, and $R_{6b}$ are as defined for formula (I) can be prepared by heating compounds of formula (6) wherein W is Cl, Br or I with compounds of formula $HO[C(R_{18})(R_{19})]_qR_{6a}(L_3R_{6b})_n$ wherein n is 0 or 1 and $R_{6a}$, $R_{6b}$, q, $R_{18}$, $R_{19}$ and $L_3$ are as defined in formula (I), in the presence of a base such as $Cs_2CO_3$ and a catalyst such as $Pd(OAc)_2$ in a solvent such as toluene or DMF (Torraca, K. E.; et. al. J. Amer. Chem. Soc. 123, 2001, 10770–10771.) Compounds of formula (7), wherein n is 0 or 1, $L_2$ is —$[C(R_{18})(R_{19})]_q$, q is 1, and X, X', Y, Y', Z, Z', $R_2$, $R_3$, $R_4$, $R_5$, $L_3$, $R_{6a}$, $R_{6b}$, $R_{18}$ and $R_{19}$ are as defined for formula (I), can be prepared from compounds of formula (8). Compounds of formula (8) can be manipulated by reactions well known to those skilled in the art of organic chemistry such as the Grignard reaction, catalytic hydrogenation, metal hydride reduction, alkylation of alcohols, fluorination with (diethylamino)sulfur trifluoride, fluorination with [bis(2-methoxyethyl)amino]sulfur trifluoride to provide compounds of formula (7), wherein n is 0 or 1, $L_2$ is —[C($R_{18}$)($R_{19}$)]$_q$, q is 1, and X, X', Y, Y', Z, Z', $R_2$, $R_3$, $R_4$, $R_5$, $L_3$, $R_{6a}$, $R_{18}$, $R_{19}$, and $R_{6b}$ are defined for formula (I).

Compounds of formula (7), wherein n is 0 or 1, $L_2$ is —[C($R_{18}$)($R_{19}$)]$_q$ and X, X', Y, Y', Z, Z', $R_2$, $R_3$, $R_4$, $R_5$, $L_3$, $R_{6a}$, $R_{6b}$, $R_{18}$, $R_{19}$ and q are as defined for formula (I) can be prepared by cross-coupling reactions known to those skilled in the art. Examples of these reactions are the Kumada, Suzuki, Heck, Stille, Suzuki-Miyaaura, Tamao-Kamuda and Sonogashira reaction. Suitable reagents, for example, alkyl Grignard reagents, boronic acids or ester, tin intermediates, alkenes and alkynes can be coupled with compounds of formulas (6) wherein W is triflate or halogen, in the presence of a metal catalyst such as palladium, nickel, silver or indium, to prepare compounds of formula (7), wherein $L_2$ is a substituted or unsubstituted alkyl, alkenyl or alkynyl chain. Compounds of formula (7) wherein $L_2$ is an alkenyl or alkynyl chain can be reduced to compounds of formula (7) wherein $L_2$ is an alkyl chain by methods known to those skilled in the art such as catalytic hydrogenation. References that describe these methodologies are: G. A. Molander et al., Tetrahedron, 58:1465–1470 (2002); W. Dohle et. al., Org. Lett., 3:2871–2873 (2001); G. Zou et al., Tet. Lett., 42:7213–7216 (2001); A. J. Suzuki, Organomet. Chem., 576:147–168 (1999); A. F. Littke, J. Amer. Chem. Soc., 122:4020–4028 (2000); N. Miyaura et al., Chem. Rev., 95:2457–2483 (1995); H. Horie et al., J. Mater. Chem., 11:1063–1071 (2001); C. Dai et al., J. Amer. Chem. Soc., 123:2719–2724 (2001); F. Diederich et al., Metal-catalyzed Cross-Coupling Reactions, Wiley-VCH; Weinheim, 1998; A. Mohanakrishnan et al., Syn. Lett., 7:1097–1099 (1999); B. H. Lipshutz et al., Org. Lett., 3:1869–1872 (2001); B. H. Lipshutz et al., Tet. Lett., 40:197–200 (1999); and J. Tsuji, Palladium Reagents and Catalysts-Innovations in Organic Synthesis, John Wiley & Sons: New York, 1995.

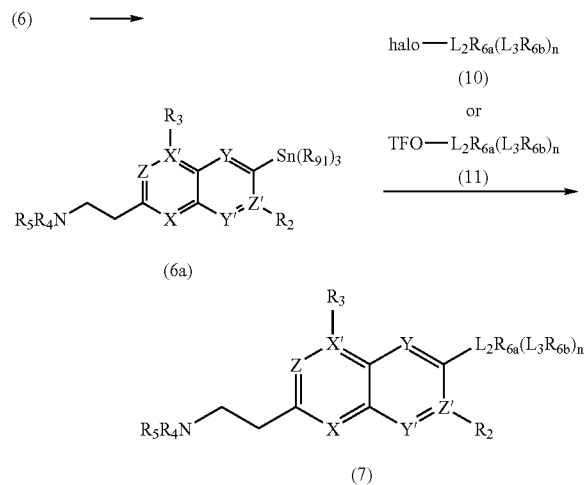

Compounds of formula (7), wherein $L_2$ is a bond, n is 0 or 1, and X, X', Y, Y', Z, Z', $R_2$, $R_3$, $R_4$, $R_5$, $R_{6a}$, $R_{6b}$ and $L_3$ are as defined in formula (I) can be prepared as described in Scheme 2. Halides of formula (6) wherein W is Br, Cl, or I, can be treated with a distannane such as hexamethyldistin (CAS # 661-69-8) in the presence of a catalyst such as Pd(PPh$_3$)$_4$ in a solvent such as dioxane with heating to provide tin intermediates of structure (6a), wherein $R_{91}$ is lower alkyl (Li, D.; et al., J. Org. Chem., 65, pages 2802–2805, (2000)). Alternatively, compounds of formula (6) wherein W is Br or I can be treated with an alkyllithium reagent such as sec-BuLi in a solvent such as THF or diethyl ether at −78° C. to provide an intermediate lithium species via a lithium-halogen exchange reaction followed by reaction with trialkyltin chloride such as tri-n-butyltin chloride to provide tin intermediates of structure (6a). Using the Stille coupling reaction conditions as described in Scheme 1, tin intermediates of structure (6a) can be reacted with halides of formula (10) or triflates of structure (11) wherein n is 0 or 1 in both structures, to provide compounds of formula (7) wherein $L_2$ is a bond, n is 0 or 1, and X, X', Y, Y', Z, Z', $R_2$, $R_3$, $R_4$, $R_5$, $R_{6a}$, $R_{6b}$ and $L_3$ are as defined in formula (I).

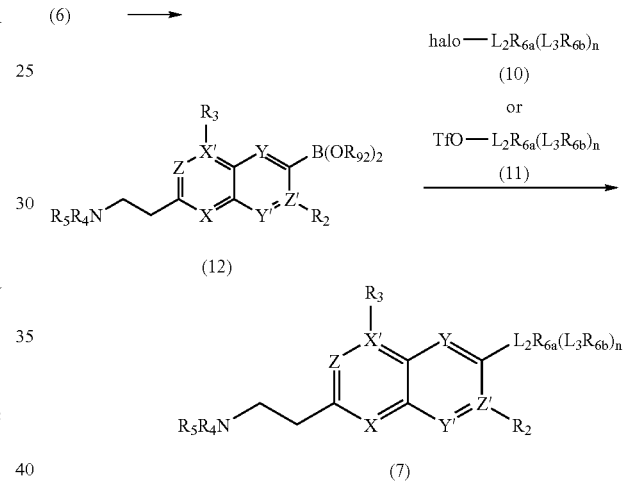

Alternatively, compounds of formula (7), wherein $L_2$ is a bond, n is 0 or 1, and X, X', Y, Y', Z, Z', $R_2$, $R_3$, $R_4$, $R_5$, $R_{6a}$, $R_{6b}$ and $L_3$ are as defined in formula (I) can be prepared as described in Scheme 3. Compounds of formula (6) wherein W is Br or I can be treated with an alkyllithium reagent such as sec-BuLi in a solvent such as THF or diethyl ether at −78° C. to provide an intermediate lithium species via a lithium-halogen exchange reaction followed by a trialkoxyborate such as triiosopropyl borate to provide a borate intermediate of formula (12) wherein $R_{92}$ is hydrogen. Alternatively, compounds of formula (6) wherein W is triflate, Br, Cl or I, can be treated with bis-(pinacolato)diboron in the presence of a catalyst such as PdCl$_2$(dppf) as described in Ishiyama, T. et. al., J. Org. Chem. 60:7508–7510 (1995) to provide borates of general structure (12) wherein B(OR$_{92}$)$_2$ is boron-pinacolate. Using the Suzuki coupling reaction as described in Scheme 1, a reaction well known to those skilled in the art of organic chemistry, borate intermediates of structure (12) can be reacted with halides of structure (10) or triflates of structure (11) wherein n is 0 or 1 in both structures, to provide compounds of general structure (7) wherein $L_2$ is a bond, n is 0 or 1 and X, X', Y, Y', Z, Z', $R_2$, $R_3$, $R_4$, $R_5$, $L_3$, $R_{6a}$, and $R_{6b}$ are as defined for formula (I).

Scheme 4

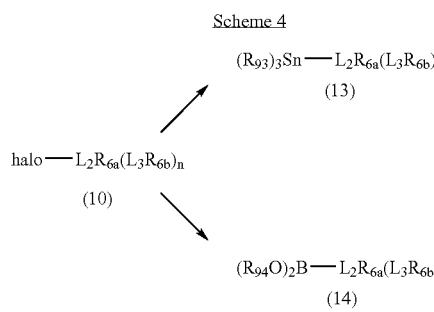

Tin intermediates of formula (13) wherein $R_{93}$ is lower alkyl, n is 0 or 1, $L_2$ is a bond, and $L_3$, $R_{6a}$ and $R_{6b}$ are as defined in formula (I), can be prepared as described in Scheme 4 from the corresponding halides of formula (10), wherein $L_2$ is a bond, n is 0 or 1, by treatment with a distannane such as hexamethylditin (CAS # 661-69-8) in the presence of a catalyst such as $Pd(PPh_3)_4$ in a solvent such as dioxane with heating to provide tin intermediates of structure (13), wherein $R_{93}$ is lower alkyl. Alternatively, halide intermediates of structure (10) can be reacted with an alkyl lithium reagent such as sec-BuLi to provide an intermediate lithium species which can then be treated with a tri-alkyltin chloride such as trimethyltin chloride. An example of this transformation can be found in Balle, T. et. al., *Synthesis* (11):1509–1512 (2002).

Boronic acid ester intermediates of formula (14), wherein $R_{94}$ is H or lower alkyl, $L_2$ is a bond, n is 0 or 1, and $L_3$, $R_{6a}$ and $R_{6b}$ are as defined in formula (I), can be prepared by the reaction of halides of formula (10), wherein $L_2$ is a bond and n is 0 or 1, with an alkyllithium reagent such as sec-BuLi in a solvent such as THF or ether at −78° C. to provide an intermediate lithium species via a lithium-halogen exchange reaction followed by a trialkoxyborate such as triiosopropyl borate. Halides of structure (10) can be also treated with bis-(pinacolato)diboron in the presence of a catalyst such as $PdCl_2(dppf)$ as described in Ishiyama, T.; et. al. *J. Org. Chem.* 1995, 60, 7508–7510 to provide borates of general structure (14), wherein $B(OR_{94})_2$ is boronpinacolate, $L_2$ is a bond and n=0 or 1.

Compounds of general structure (7) wherein n is 0 can be converted to compounds of formula (7) wherein n is 1, and X, X', Y, Y', Z, Z', $R_2$, $R_3$, $R_4$, $R_5$, $R_{6a}$, $R_{6b}$, $L_2$ and $L_3$ are as defined in formula (I), using the general methodologies that are described in Schemes 1, 2, 3 and 4.

Scheme 5

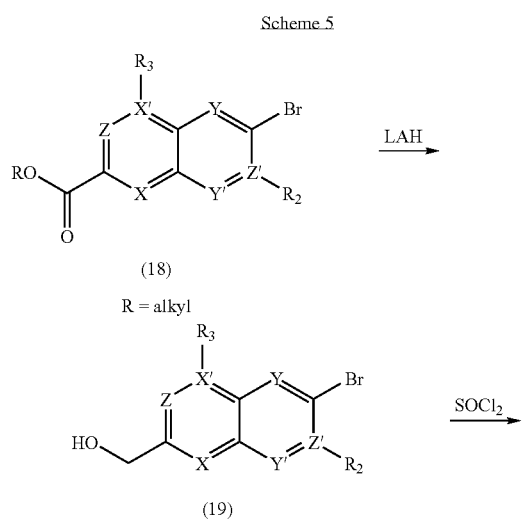

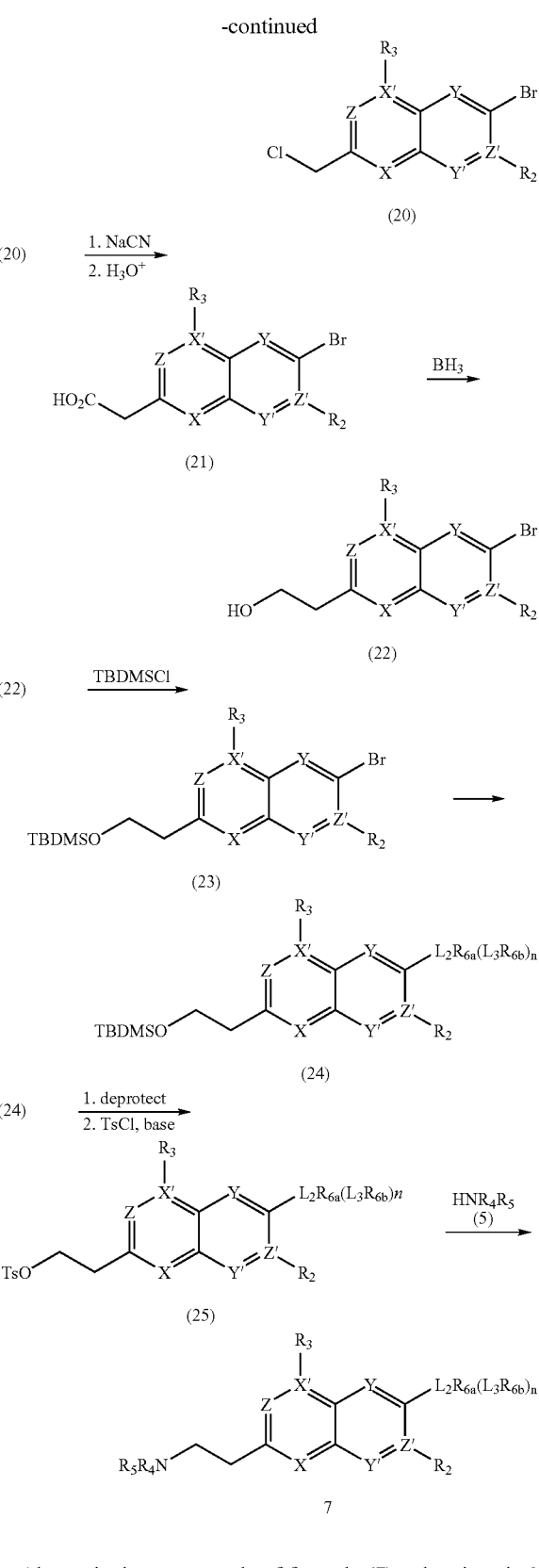

Alternatively, compounds of formula (7), wherein n is 0 or 1, and X, X', Y, Y', Z, Z', $R_2$, $R_3$, $R_4$, $R_5$, $R_{6a}$, $R_{6b}$, $L_2$ and $L_3$ are as defined in formula (I), can be prepared as described in Scheme 5. Esters of formula (18) can be treated with a reducing agent such as, but not limited to, lithium aluminum hydride to provide alcohols of formula (19). Alcohols of formula (19) can be treated with thionyl chloride to provide chlorides of formula (20). Chlorides of formula (20) can be treated with sodium cyanide or potassium cyanide to provide the nitrile which can be treated with aqueous acid to provide acids of formula (21). Acids of formula (21) can be treated with a reducing agent such as, but not limited to, diborane or borane THF complex to provide alcohols of formula (22). Alcohols of formula (22) can be used in place of compound (3) in Scheme 1. Alternatively, alcohols of formula (22) can be treated with a hydroxy-protecting reagent such as, but not limited to, tert-butyldimethylsilyl chloride. The protected compounds of formula (23) can be processed as described in Schemes 1, 2, 3 and 4 to provide compounds of formula (24). Compounds of formula (24) can be deprotected using methods known to those of ordinary skill in the art and then treated with a sulfonyl chloride such as, but not limited to, methanesulfonyl chloride or p-toluensulfonyl chloride to provide sulfonates of formula (25). Sulfonates of formula (25) can be treated with an amine of formula (5) to provide compounds of formula (7).

with amines of formula (5) to provide compounds of formula (28). Compounds of formula (28) can be processed as described in Schemes 1, 2, 3 and 4 to provide compounds of formula (29).

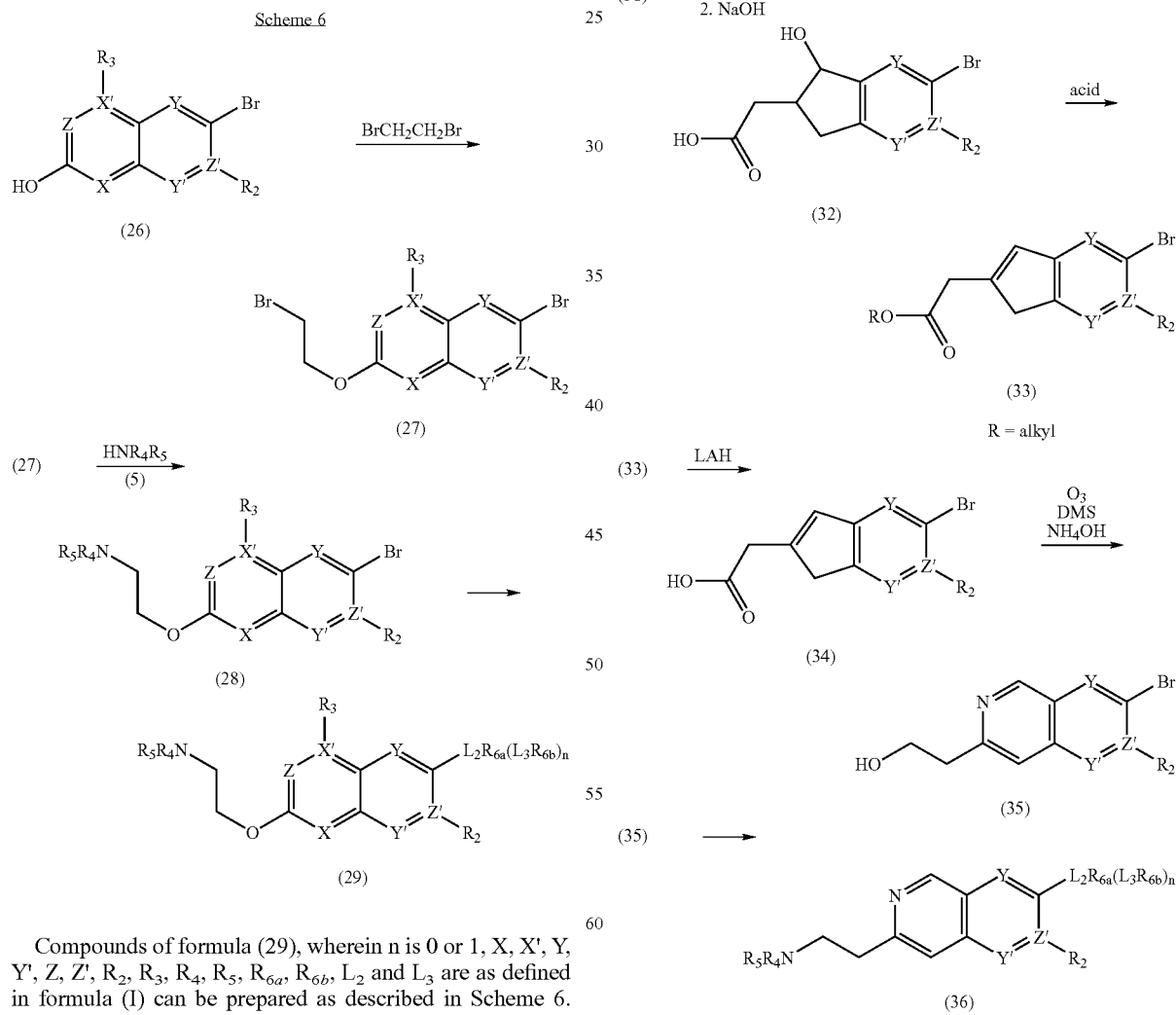

Compounds of formula (29), wherein n is 0 or 1, X, X', Y, Y', Z, Z', $R_2$, $R_3$, $R_4$, $R_5$, $R_{6a}$, $R_{6b}$, $L_2$ and $L_3$ are as defined in formula (I) can be prepared as described in Scheme 6. Hydroxy compounds of formula (26), purchased or prepared using methods known to those of ordinary skill in the art, can be treated with 1,2 1,2-dibromoethane to provide bromides of formula (27). Bromides of formula (27) can be treated Compounds of formula (36), wherein n is 0 or 1, Y, Y', Z', $R_2$, $R_4$, $R_5$, $R_{6a}$, $R_{6b}$, $L_2$ and $L_3$ are as defined in formula (I), can be prepared as described in Scheme 7. Indanones of formula (30) can be treated with a base such as, but not limited to, lithium diisopropylamide and ethyl bromoacetate to provide esters of formula (31). Esters of formula (31) can be treated with borane-tert-butylamine complex and then an aqueous basic solution such as, but not limited to, sodium hydroxide in water to provide hydroxyacids of formula (32). Hydroxyacids of formula (32) can be treated with a strong acid such as, but not limited to, concentrated sulfuric acid with heat in a solvent such as methanol to provide esters of formula (33). Esters of formula (33) can be treated with a reducing agent such as, but not limited to, lithium aluminum hydride to provide alcohols of formula (34). Alcohols of formula (34) can be treated with ozone followed by dimethylsulfide and ammonium hydroxide to provide isoquinolines of formula (35). Isoquinolines of formula (35) can be processed as described in Schemes 1, 2, 3 and 4 to provide compounds of formula (36).

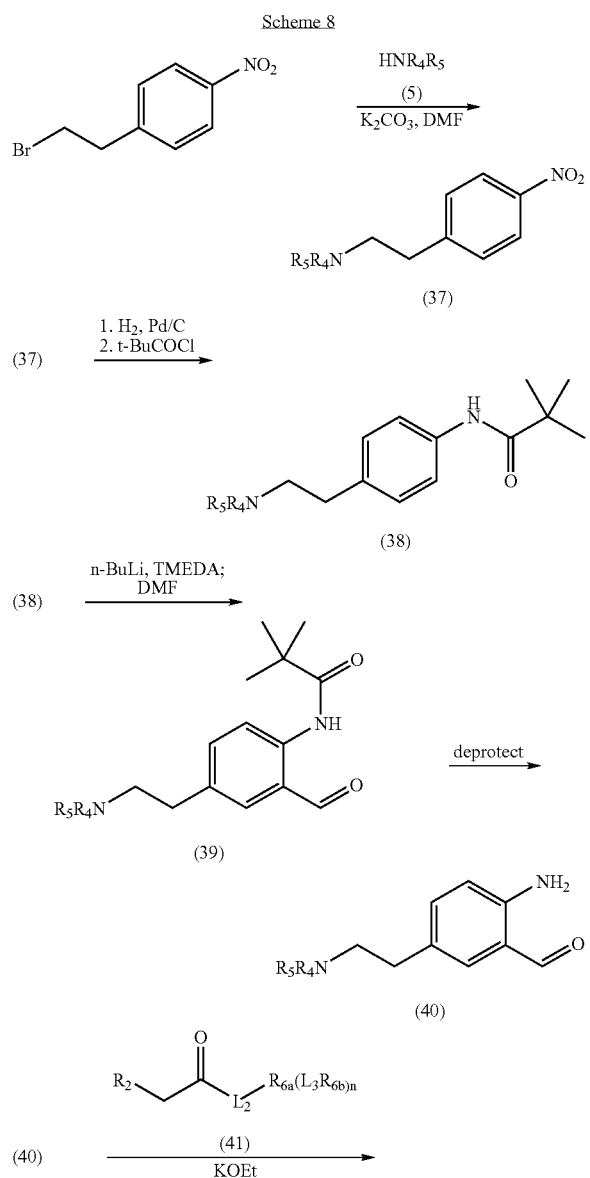

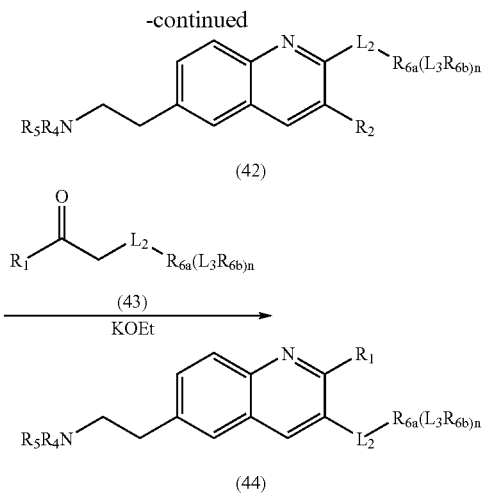

Compounds of formula (42), wherein n is 0 or 1, and $L_3$, $R_2$, $R_4$, $R_5$, $R_{6a}$, $R_{6b}$ are as defined for formula (I), n is 0 or 1, and $L_2$ is $-[C(R_{18})(R_{19})]_q-$ or a bond can be prepared as described in Scheme 8. 1-(2-Bromoethyl)-4-nitrobenzene can be treated with amines of formula (5) to provide amines of formula (37). Amines of formula (37) can be treated with palladium on carbon under a hydrogen atmosphere to provide anilines which can then be treated with a nitrogen protecting reagent such as, but not limited to, trimethylacetyl chloride to provide protected anilines of formula (38). Protected anilines of formula (38) can be treated with an organolithium reagent such as, but not limited to, n-butyllithium, sec-butyllithium, or tert-butyllithium and N,N-dimethylformamide to provide aldehydes of formula (39). The aniline of aldehydes of formula (39) can be deprotected using methods well know to those skilled in the art such as, but not limited to, heating in aqueous hydrochloric acid to provide aldehydes of formula (40). Aldehydes of formula (40) can be treated with ketones of formula (41) and a base such as, but not limited to, potassium ethoxide in a solvent such as ethanol to provide compounds of formula (42).

Compounds of formula (44), wherein n is 0 or 1, $L_3$, $R_1$, $R_4$, $R_5$ and $R_{6a}$, $R_{6b}$ are as defined in formula (I) and $L_2$ is $-[C(R_{18})(R_{19})]_q-$ or a bond can be prepared as described in Scheme 8. Aldehydes of formula (40) can be treated with ketones of formula (43) and a base such as, but not limited to, potassium ethoxide to provide compounds of formula (44).

Compounds of formula (41) and (43) can be purchased commercially or synthesized from procedures which are known to those skilled in the art. The following are some of the references that describe methodologies for the synthesis of compounds (41) and (43) wherein n is 0 or 1 and $L_3$ is a bond: Gilberto A. R, et. al. *Tetrahedron Letters*, 38(29): 5103–5106, (1997); Singh, Shiv P. et. al. *Heterocycl. Commun.*, 7:49 (2001); Umesha, K. B et. al. *Synth. Commun.*, 32:1841–1846, (2002); Rogelio J. et. al., *Heterocycles*, 35:591–598, (1993); Butler, D. E., et. al., *J. Org. Chem.*, 36:2542–2547 (1971); Katsura, Y., et. al., *Chem. Pharm. Bull.*, 40(9):2432–2441, (1992); Csavassy, G.; Gyoerfi, Z. A., *Justus Liebigs Ann. Chem.*, 1195–1205 (1974); and Arya, V. P. et al., *Indian J. Chem. Sect B*, (15):1129–1132 (1977).

Alternatively, compounds of formula (42) and (44) wherein n is 1 and $L_3$ is a bond can be made from compounds of formula (42) and (44) wherein n is 0 using metal catalyzed coupling reactions that are described in Schemes 1, 2, 3, and 4.

Compounds of formula (42) and (44) wherein n is 1 and $L_3$ is —N(H)—, —N(alkyl)-, —S—, —O—, or -[($CR_{16}$)($R_{17}$)]$_v$O— can be made from compounds of formula (42) and (44) wherein n is 0 and $R_{6a}$ contains functionality that facilitate coupling (e.g. halides, triflates, tosylates, alcohols and the like) with compounds of formula $NH_2R_{6b}$, N(H)(alkyl)$R_{6b}$, HS$R_{6b}$, or HO$R_{6b}$, using reaction conditions that are described in Scheme 1.

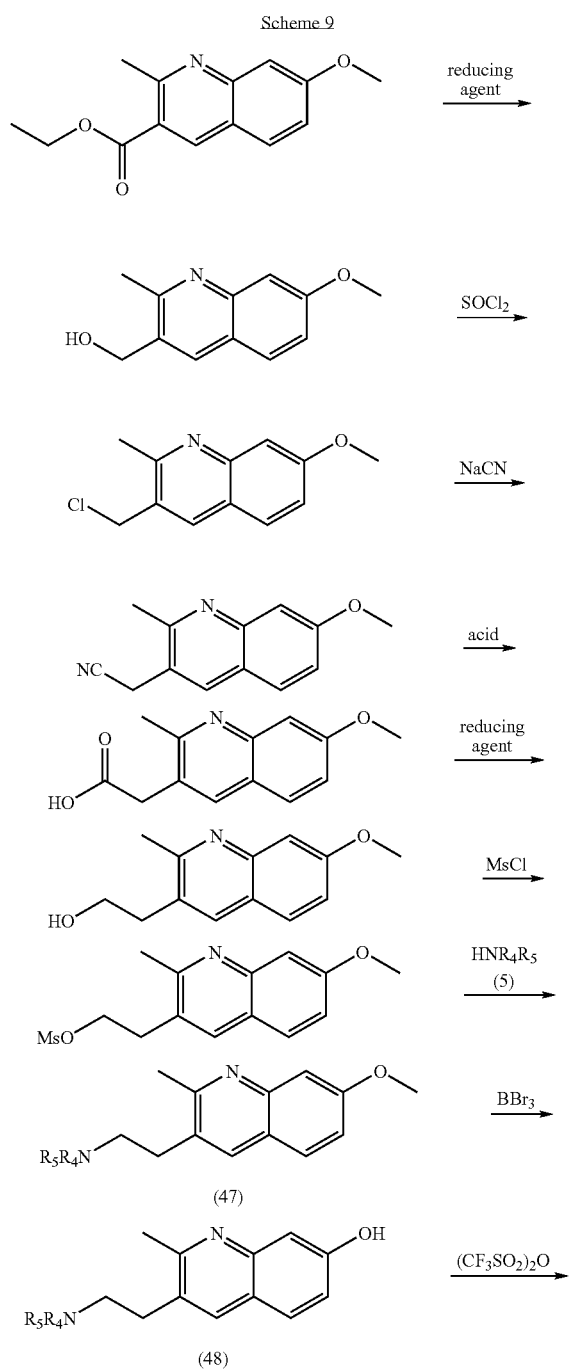

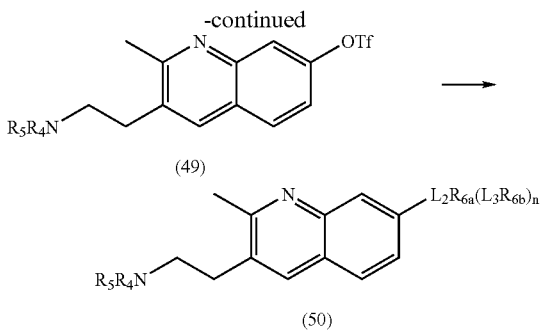

Compounds of formula (50), wherein n is 0 or 1, and $L_2$, $L_3$, $R_{6a}$, $R_{6b}$, $R_4$ and $R_5$ are as defined in formula (I), can be prepared as described in Scheme 9. Ethyl 7-methoxy-2-methyl-3-quinolinecarboxylate can be prepared using the procedures described in *Synthetic Comm.*, 17(14):1647–1653, (1987). Ethyl 7-methoxy-2-methyl-3-quinolinecarboxylate can be treated with a reducing agent, such as, but not limited to, lithium aluminum hydride or sodium borohydride, to provide (7-methoxy-2-methyl-3-quinolinyl)methanol. (7-Methoxy-2-methyl-3-quinolinyl)methanol can be treated with a chlorinating reagent, such as, but not limited to, thionyl chloride to provide 3-(chloromethyl)-7-methoxy-2-methylquinoline. 3-(Chloromethyl)-7-methoxy-2-methylquinoline can be treated with sodium cyanide or potassium cyanide to provide (7-methoxy-2-methyl-3-quinolinyl)acetonitrile. (7-Methoxy-2-methyl-3-quinolinyl)acetonitrile can be treated with acid, such as, but not limited to, glacial acetic acid and concentrated sulfuric acid, in water and 1,4-dioxane with heat to provide (7-methoxy-2-methyl-3-quinolinyl)acetic acid. (7-Methoxy-2-methyl-3-quinolinyl)acetic acid can be treated with a reducing agent, such as, but not limited to, $B_2H_6$, borane-THF complex, or borane-pyridine complex, to provide 2-(7-methoxy-2-methyl-3-quinolinyl)ethanol. 2-(7-Methoxy-2-methyl-3-quinolinyl)ethanol can be treated with methanesulfonyl chloride and a base, such as, but not limited to, triethylamine or diisopropylamine to provide 2-(7-methoxy-2-methyl-3-quinolinyl)ethyl methanesulfonate. 2-(7-Methoxy-2-methyl-3-quinolinyl)ethyl methanesulfonate can be treated with an amine of formula (5) to provide amines of formula (47). Amines of formula (47) can be treated with $BBr_3$ to provide hydroxy compounds of formula (48). Hydroxy compounds of formula (48) can be treated with trifluoromethanesulfonic anhydride or trifluoromethanesulfonyl chloride to provide triflates of formula (49). Triflates of formula (49) can be treated with boronic acids of formula of formula (14) wherein $L_2$ is a bond, n is 0 or 1 and $R_{6a}$ and $R_{6b}$ are as defined in a compound of formula (I), using reaction condition as described in Schemes 1, 3 and 4 to provide compounds of formula (50). Compounds of formula (50) wherein $L_2$ is other than a bond and n is 0 or 1, can be prepared from compounds of formula (49) using processes as described in Scheme 1. Compounds of formula (50) wherein n is 0 can be converted to compounds of formula (50) wherein n is 1 and $L_2$, $L_3$, $R_4$, $R_5$, $R_{6a}$, and $R_{6b}$ are as defined in formula (I) using reaction conditions that are described in Schemes 1, 2, 3, and 4.

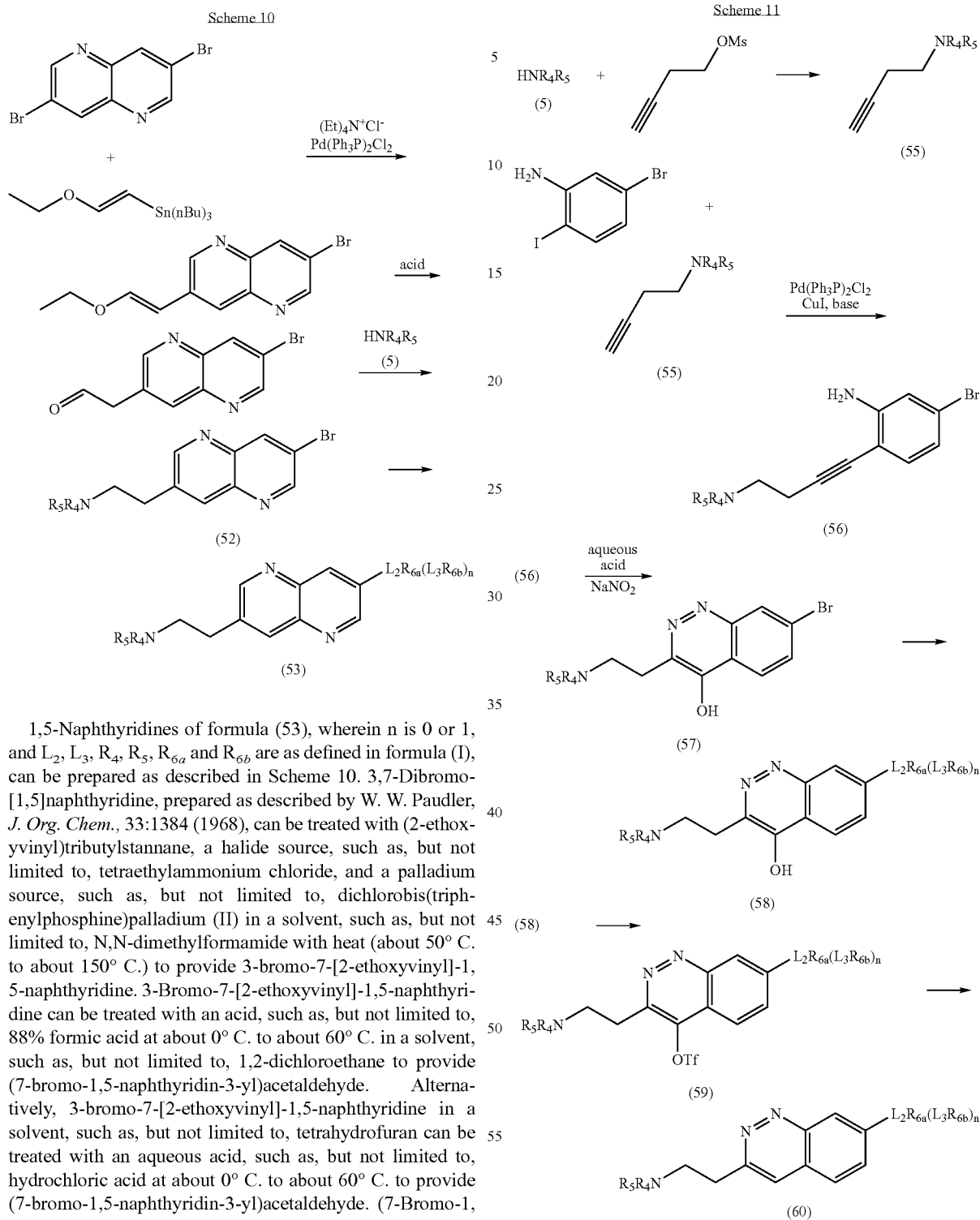

1,5-Naphthyridines of formula (53), wherein n is 0 or 1, and $L_2$, $L_3$, $R_4$, $R_5$, $R_{6a}$ and $R_{6b}$ are as defined in formula (I), can be prepared as described in Scheme 10. 3,7-Dibromo-[1,5]naphthyridine, prepared as described by W. W. Paudler, *J. Org. Chem.,* 33:1384 (1968), can be treated with (2-ethoxyvinyl)tributylstannane, a halide source, such as, but not limited to, tetraethylammonium chloride, and a palladium source, such as, but not limited to, dichlorobis(triphenylphosphine)palladium (II) in a solvent, such as, but not limited to, N,N-dimethylformamide with heat (about 50° C. to about 150° C.) to provide 3-bromo-7-[2-ethoxyvinyl]-1,5-naphthyridine. 3-Bromo-7-[2-ethoxyvinyl]-1,5-naphthyridine can be treated with an acid, such as, but not limited to, 88% formic acid at about 0° C. to about 60° C. in a solvent, such as, but not limited to, 1,2-dichloroethane to provide (7-bromo-1,5-naphthyridin-3-yl)acetaldehyde. Alternatively, 3-bromo-7-[2-ethoxyvinyl]-1,5-naphthyridine in a solvent, such as, but not limited to, tetrahydrofuran can be treated with an aqueous acid, such as, but not limited to, hydrochloric acid at about 0° C. to about 60° C. to provide (7-bromo-1,5-naphthyridin-3-yl)acetaldehyde. (7-Bromo-1,5-naphthyridin-3-yl)acetaldehyde can be treated with an amine of formula (5) under reductive amination conditions, such as, but not limited to, sodium triacetoxyborohydride and an acid, such as, but not limited to, acetic acid in a solvent, such as, but not limited to, 1,2-dichloroethane at about 0° C. to about 50° C. to provide amines of formula (52). Amines of formula (52) can be processed as Schemes 1, 2, 3 and 4 to provide 1,5-naphthyridines of formula (53).

Cinnolines of formula (60), wherein n is 0 or 1, and $L_2$, $L_3$, $R_4$, $R_5$, $R_{6a}$, and $R_{6b}$ are as defined in formula (I), can be prepared as described in Scheme 11. Amines of formula (5) can be treated with 3-butynyl methanesulfonate at room temperature with stirring for about 1 hour and then heated at about 50° C. for about 24 hours. The mixture is allowed to cool to room temperature, and filtered. The filtrate is diluted with acetonitrile to provide a 0.1 M solution of alkynes of formula (55) for use in subsequent steps. 5-Bromo-2-iodophenylamine, prepared as described by Sakamoto in *Chem. Pharm. Bull.*, 35:1823 (1987), can be treated with alkynes of formula (55), a source of palladium (II), such as, but not limited to, Pd(Ph$_3$P)$_2$Cl$_2$, CuI, and a base, such as, but not limited to, triethylamine in an organic solvent, such as, but not limited to, DMF at about 50° C. to about 80° C. to provide alkynes of formula (56). Alkynes of formula (56) can be treated with aqueous acid, such as but not limited to aqueous HCl in the presence of sodium nitrite at about 0° C. to about 100° C. to provide hydroxy cinnolines of formula (57). Hydroxy cinnolines of formula (57) can be processed as described in Schemes 1, 2, 3 and 4 to provide hydroxy cinnolines of formula (58). Hydroxy cinnolines of formula (58) can be treated with N-phenylbis(trifluoromethanesulfonimide) and a base, such as, but not limited to, diisopropylethylamine in an organic solvent, such as, but not limited to, 1,2-dichloroethane at about 25° C. to about 40° C. to provide triflates of formula (59). Triflates of formula (59) can be treated with a catalytic palladium source, such as, but not limited to, palladium (II) acetate and a hydrogen donor, such as, but not limited to, formic acid at about 25° C. to about 50° C. to provide cinnolines of formula (60).

a base, such as, but not limited to, triethylamine or pyridine in a solvent, such as, but not limited to, dichloromethane at about 0° C. or room temperature to provide 7-chloro-3-cinnolinyl trifluoromethanesulfonate. 7-Chloro-3-cinnolinyl trifluoromethanesulfonate can be treated with (2-ethoxyvinyl)tributylstannane, a halide source, such as, but not limited to, tetraethylammonium chloride, and a palladium source, such as, but not limited to, dichlorobis(triphenylphosphine) palladium (II) in a solvent, such as, but not limited to, N,N-dimethylformamide at about 50° C. to about 150° C. to provide 7-chloro-3-(2-ethoxyvinyl)cinnoline. 7-Chloro-3-(2-ethoxyvinyl)cinnoline can be processed as described in Scheme 10 to provide amines of formula (62). Amines of formula (62) can be treated with boronic acids or esters of formula (14) wherein L$_2$ is a bond, and n is 0 or 1, a palladium source, such as, but not limited to, dichloro(di-tert-butylphosphinous acid)palladium (II) dimer) or tris (dibenzylideneacetone)dipalladium (0), tri(tert-butyl)phosphine, and a base, such as, but not limited to, cesium fluoride, in a solvent, such as, but not limited to, 1,4-dioxane at about 30° C. to about 120° C. to provide cinnolines of formula (60). Alternatively, compounds of formula (62) can also be subjected to reaction conditions that are described in Schemes 1, 3, and 4 to provide compounds of formula (60) wherein n is 1 and L$_2$, L$_3$, R$_4$, R$_5$, R$_{6a}$, and R$_{6b}$ are as defined in formula (I).

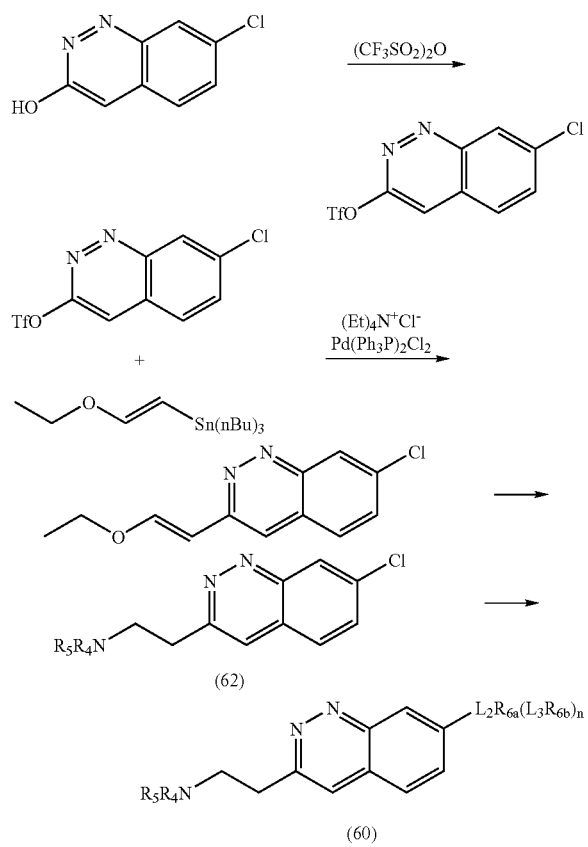

Cinnolines of formula (60), wherein n is 0 or 1, and L$_2$, L$_3$, R$_4$, R$_5$, R$_{6a}$ and R$_{6b}$ are as defined in formula (I), also can be prepared as described in Scheme 12. 7-Chloro-3-cinnolinol, prepared as described by H. E. Baumgarten, *J. Het. Chem.*, 6:333 (1969), can be treated with trifluoromethanesulfonyl chloride or trifluoromethanesulfonic anhydride and

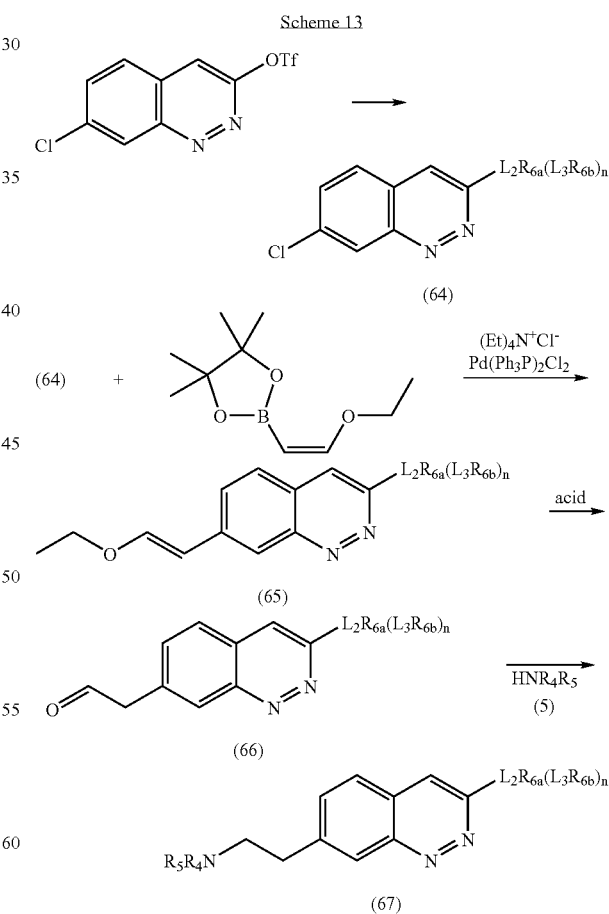

Cinnolines of formula (67), wherein n is 0 or 1, and L$_2$, L$_3$, R$_4$, R$_5$, R$_{6a}$ and R$_{6b}$ are as defined for formula (I), can be prepared as described in Scheme 13. 7-Chloro-3-cinnolinyl trifluoromethanesulfonate, prepared as described in Scheme 12, can be treated with boronic acids or esters of formula (14), wherein $L_2$ is a bond, n is 0 or 1, a palladium source, such as, but not limited to, tris(dibenzylideneacetone)dipalladium (0), tricyclohexylphosphine (or triphenylphosphine or tri(tert-butyl)phosphine), and a base, such as, but not limited to, potassium fluoride, in a solvent, such as, but not limited to, tetrahydrofuran at about 20° C. to about 80° C. to provide chlorides of formula (64). Chlorides of formula (64) wherein n is 0 or 1, can be treated with 2-(2-ethoxy-vinyl)-4,4,5,5-tetramethyl-[1,3,2]dioxaborolane, prepared as described by C. M. Vogels in Chem. Commun. (2000) 1, 51, a palladium source, such as, but not limited to, tris(dibenzylideneacetone)dipalladium (0), tri (tert-butyl)phosphine or, in place of both, dichloro(di-tert-butylphosphinous acid)palladium (II) dimer and a base such as cesium fluoride, in a solvent, such as, but not limited to, 1,4-dioxane at about 30° C. to about 120° C. to provide ethers of formula (65). Ethers of formula (65) can be processed as described in Scheme 10 to provide cinnolines of formula (67).

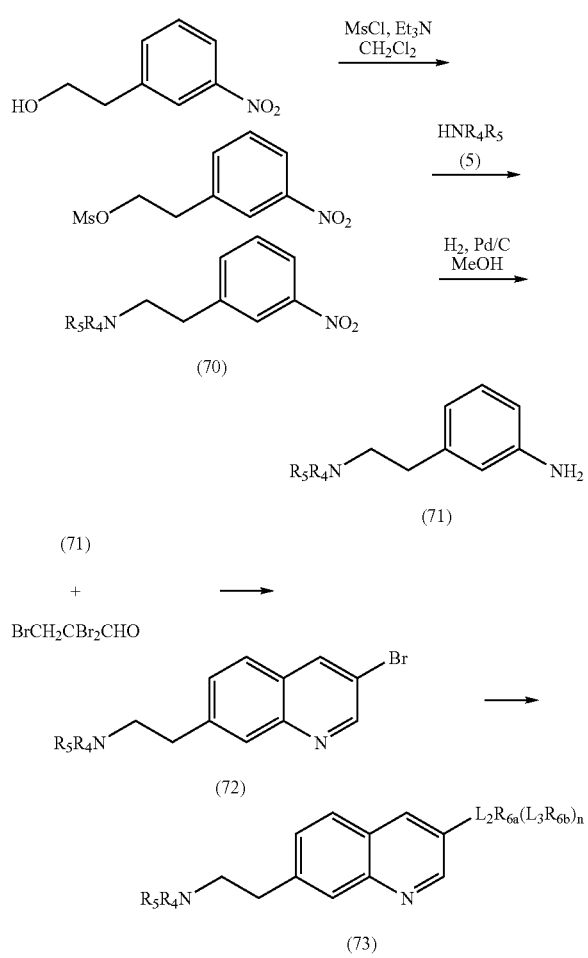

as, but not limited to, triethylamine in a solvent, such as, but not limited to, methylene chloride to provide 2-(3-nitrophenyl)ethyl methanesulfonate. 2-(3-Nitrophenyl)ethyl methanesulfonate can be treated with amines of formula (5) and a base, such as, but not limited to, potassium carbonate in a solvent, such as, but not limited to, acetonitrile to provide amines of formula (70). Amines of formula (70) can be treated with hydrogen with a palladium source, such as but not limited to palladium on carbon in a solvent, such as, but not limited to, methanol, ethanol, or ethyl acetate to provide anilines of formula (71). Anilines of formula (71) can be treated with 2,2,3-tribromopropanal as described in S. W. Tinsley, *J. Amer. Chem. Soc.* 77:4175–4176 (1955), to provide quinolines of formula (72). Quinolines of formula (72) can be processed as described in Schemes 1, 2, 3 and 4 to provide quinolines of formula (73) wherein n is 1.

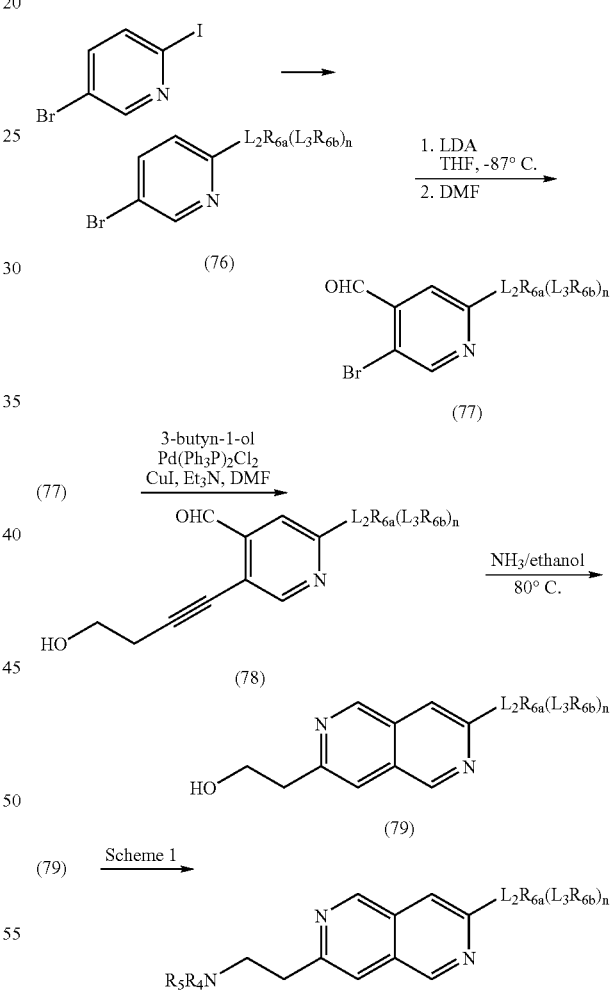

Quinolines of formula (73), wherein n is 0 or 1, and $L_2$, $L_3$, $R_4$, $R_5$, $R_{6a}$ and $R_{6b}$ are as defined in formula (I), can be prepared as described in Scheme 14. 2-(3-Nitrophenyl) ethanol, CAS #100-27-6, can be treated with methanesulfonyl chloride (or toluenesulfonyl chloride), and a base, such Naphthyridines of formula (80), wherein n is 0 or 1, and $L_2$, $L_3$, $R_4$, $R_5$, $R_{6a}$ and $R_{6b}$ are as defined in formula (I), can be prepared as described in Scheme 15. 5-Bromo-2-iodopyridine (CAS# 223463-13-6) can be processed as described in Scheme 1 to provide pyridines of formula (76). Compounds of formula (76) can be treated with a base, such as, but not limited to, lithium diisopropylamide and N,N-dimethylformamide, as described in Numata et al., Synthesis 306–311 (1999), to provide compounds of formula (77). Compounds of formula (77) can be treated with 3-butyn-1-ol, CuI, a base such as, but not limited to, triethylamine, and palladium source, such as, but not limited to, Pd(PPh$_3$)$_2$Cl$_2$ in a solvent, such as but not limited to N,N-dimethylformamide to provide alkynes of formula (78). Alkynes of formula (78) can be treated with ammonia at about 80° C. in a solvent, such as, but not limited to, ethanol to provide naphthyridines of formula (79). Naphthyridines of formula (79) can be processed as described in Scheme 1 to provide naphthyridines of formula (80).

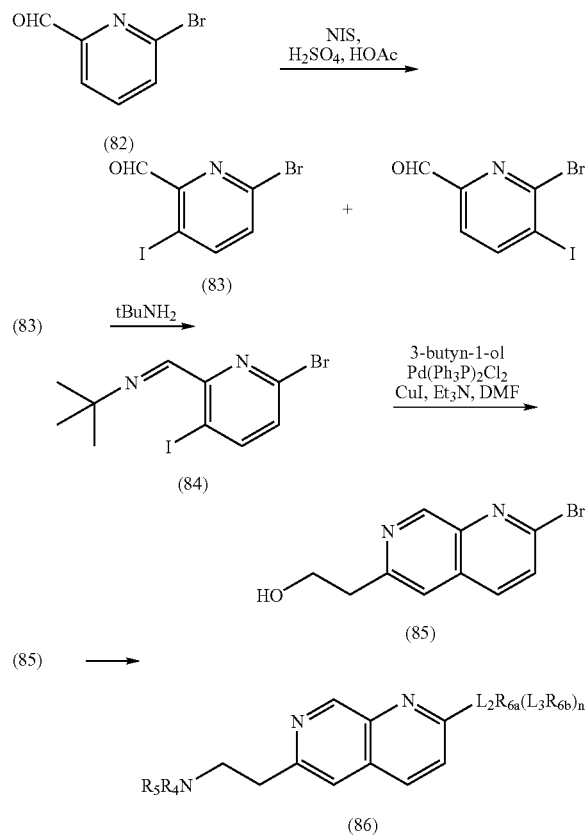

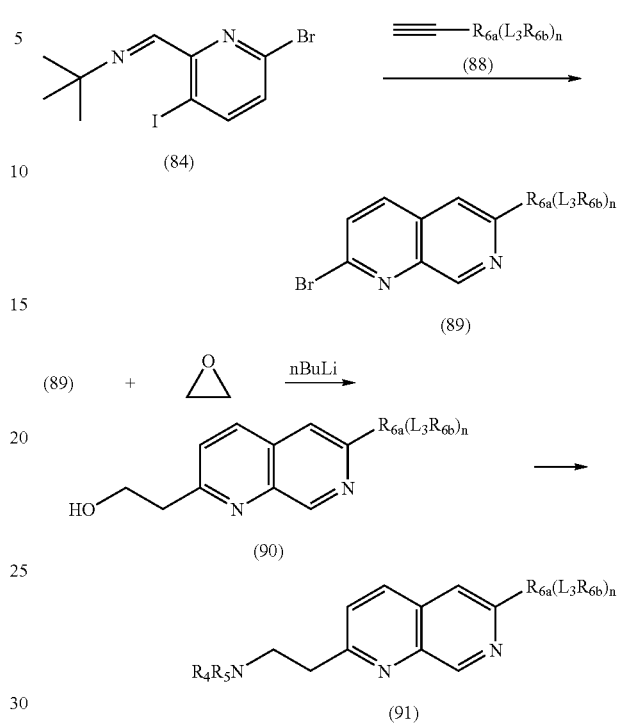

Naphthyridines of formula (86), wherein n is 0 or 1, and L$_2$, L$_3$, R$_{6a}$, R$_{6b}$, R$_4$ and R$_5$ are as defined in formula (I), can be prepared as described in Scheme 16. 6-Bromo-2-pyridinecarbaldehyde can be treated with N-iodosuccinimide in sulfuric acid and acetic acid to provide 6-bromo-3-iodo-2-pyridinecarbaldehyde and 6-bromo-5-iodo-2-pyridinecarbaldehyde. 6-Bromo-3-iodo-2-pyridinecarbaldehyde can be treated with tert-butylamine in a solvent, such as, but not limited to, THF to provide imine (84). Imine (84) can be treated with 3-butyn-1-ol, CuI, a base, such as, but not limited to, triethylamine or diisopropylamine, and a palladium source, such as, but not limited to, Pd(PPh$_3$)$_2$Cl$_2$ in a solvent, such as but not limited to N,N-dimethylformamide to provide alcohols of formula (85). Alcohols of formula (85) can be processed as described in Schemes 1, 2, 3 and 4 to provide naphthyridines of formula (86) wherein n is 1.

Naphthyridines of formula (91), wherein n is 0 or 1, and L$_2$, L$_3$, R$_{6a}$, R$_{6b}$, R$_4$ and R$_5$ are as defined in formula (I), can be prepared as described in Scheme 17. Imines of formula (84), prepared as described in Scheme 16, can be treated with alkynes of formula (88), CuI, a base, such as, but not limited to, triethylamine or diisopropylamine, and a palladium source, such as, but not limited to, Pd(PPh$_3$)$_2$Cl$_2$ in a solvent, such as but not limited to N,N-dimethylformamide to provide naphthyridines of formula (89). Naphthyridines of formula (89) can be treated with an alkyllithium reagent, such as, but not limited to, n-butyllithium, sec-butyllithium, or t-butyllithium, and ethylene oxide in a solvent, such as, but not limited to, THF or diethyl ether to provide alcohols of formula (90). Alcohols of formula (90) wherein n is 0 or 1 can be processed as described in Scheme 1, 2, 3 and 4 to provide naphthyridines of formula (91) wherein n is 1.

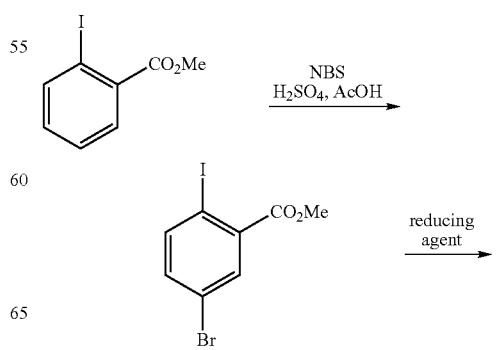

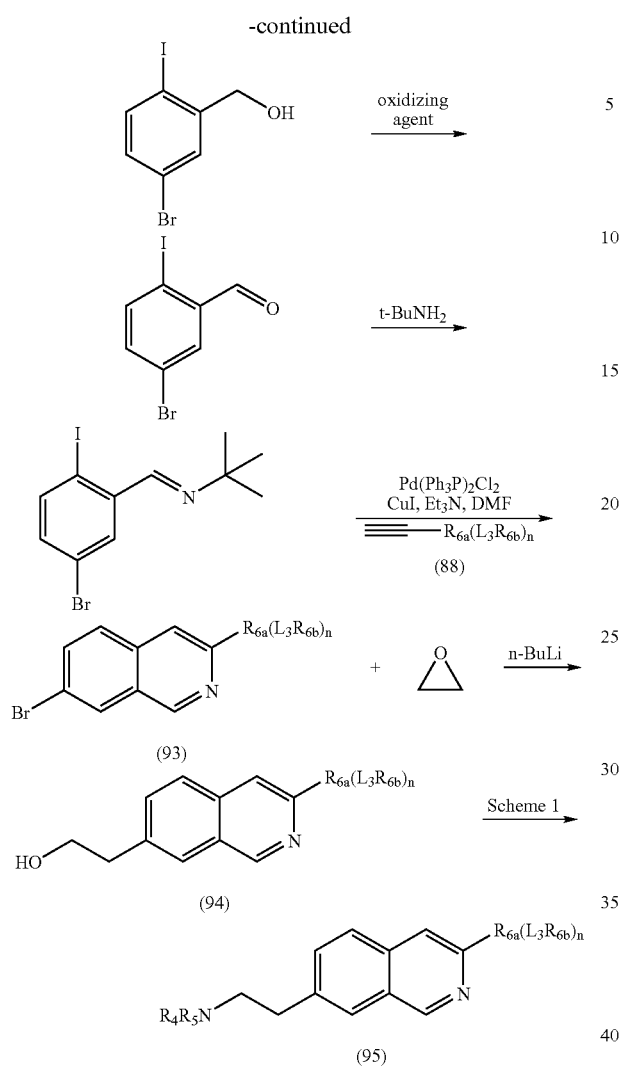

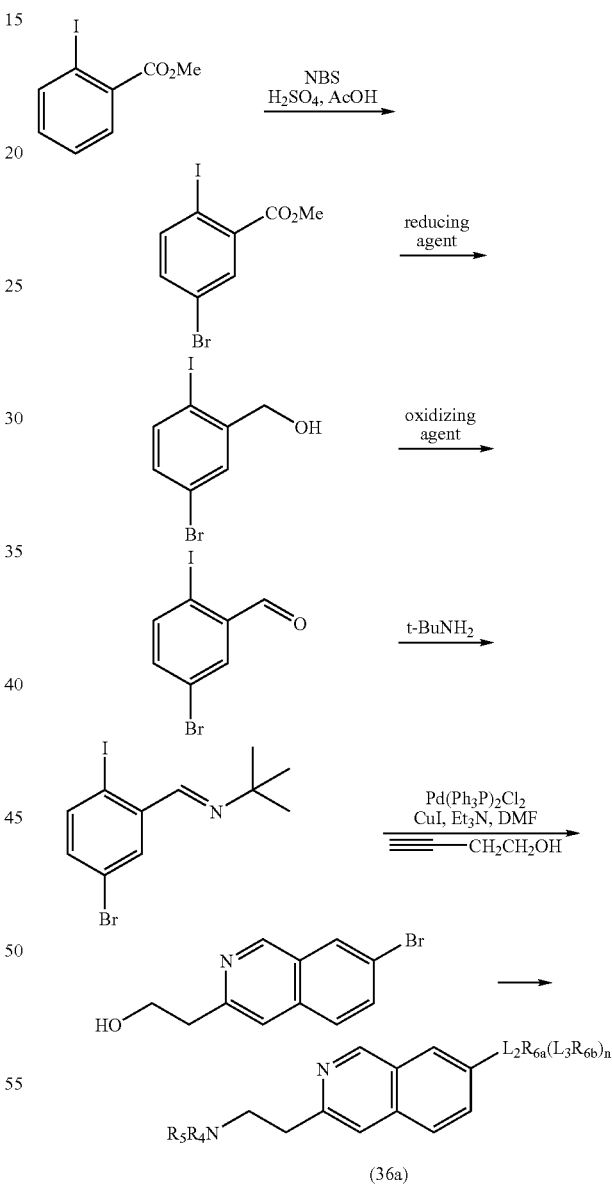

Isoquinolines of formula (95), wherein n is 0 or 1, and $L_2$, $L_3$, $R_{6a}$, $R_{6b}$, $R_4$ and $R_5$ are as defined in formula (I), can be prepared as described in Scheme 18. Methyl 2-iodobenzoate can be treated with N-bromosuccinimide in acetic acid and sufuric acid to provide methyl 5-bromo-2-iodobenzoate. Methyl 5-bromo-2-iodobenzoate can be treated with a reducing agent, such as, but not limited to, sodium borohydride or lithium aluminum hydride in a solvent, such as, but not limited to, THF, ethanol, or a mixture thereof, to provide (5-bromo-2-iodophenyl)methanol. (5-Bromo-2-iodophenyl) methanol can be treated with an oxidizing agent, such as, but not limited to, pyridinium chlorochromate, pyridinium dichromate, $MnO_2$, a peracid such as meta-chloroperoxybenzoic acid, or Swern conditions (DMSO/Cl(CO)$_2$Cl/ TEA) to provide 5-bromo-2-iodobenzaldehyde. 5-Bromo-2-iodobenzaldehyde can be treated with tert-butylamine in a solvent, such as, but not limited to, THF to provide N-[(5-bromo-2-iodophenyl)methylene]-N-(tert-butyl)amine. N-[(5-Bromo-2-iodophenyl)methylene]-N-(tert-butyl) amine can be treated with alkynes of formula (88) wherein n is 0 or 1, CuI, a base, such as, but not limited to, triethylamine or diisopropylamine, and a palladium source, such as, but not limited to, Pd(PPh$_3$)$_2$Cl$_2$ in a solvent, such as but not limited to N,N-dimethylformamide to provide isoquinolines of formula (93). Isoquinolines of formula (93) wherein n is 0 can be transformed into compounds of formula (93) wherein n is 1 using reaction conditions as described in Schemes 1, 2, 3 and 4. Isoquinolines of formula (93) can be treated with an alkyllithium reagent, such as, but not limited to, n-butyllithium, sec-butyllithium, or t-butyllithium, and ethylene oxide in a solvent, such as, but not limited to, THF or diethyl ether to provide alcohols of formula (94). Alcohols of formula (94) can be treated as described in Scheme 1 to provide isoquinolines of formula (95).

Isoquinolines of formula (36a) are a subgenus of compounds (36), wherein X, Y', and Z' are all carbon atoms, for instance CH, n is 0 or 1, and $L_2$, $L_3$, $R_{6a}$, $R_{6b}$, $R_4$ and $R_5$ are as defined in formula (I), and the compounds of the subgenus (36a) can be prepared as described in Scheme 19. Methyl 2-iodobenzoate can be treated with N-bromosuccinimide in acetic acid and sufuric acid to provde methyl 5-bromo-2-iodobenzoate. Methyl 5-bromo-2-iodobenzoate can be treated with a reducing agent, such as, but not limited to, sodium borohydride or lithium aluminum hydride in a solvent, such as, but not limited to, THF, ethanol, or a mixture thereof, to provide (5-bromo-2-iodophenyl)methanol. (5-Bromo-2-iodophenyl)methanol can be treated with an oxidizing agent, such as, but not limited to, pyridinium chlorochromate, pyridinium dichromate, $MnO_2$, a peracid such as meta-chloroperoxybenzoic acid, or Swern conditions ($DMSO/Cl(CO)_2Cl/TEA$) to provide 5-bromo-2-iodobenzaldehyde. 5-Bromo-2-iodobenzaldehyde can be treated with tert-butylamine in a solvent, such as, but not limited to, THF to provide N-[(5-bromo-2-iodophenyl)methylene]-N-(tert-butyl)amine. N-[(5-Bromo-2-iodophenyl)methylene]-N-(tert-butyl)amine can be treated with the alkyne but-3-yn-1-ol, CuI, a base, such as, but not limited to, triethylamine or diisopropylamine, and a palladium source, such as, but not limited to, $Pd(PPh_3)_2Cl_2$ in a solvent, such as, but not limited to, N,N-dimethylformamide to provide an isoquinoline. The 2-hydroxyethylisoquinoline can be treated as described in Schemes 1, 2, 3 and 4 to provide isoquinolines of formula (36a).

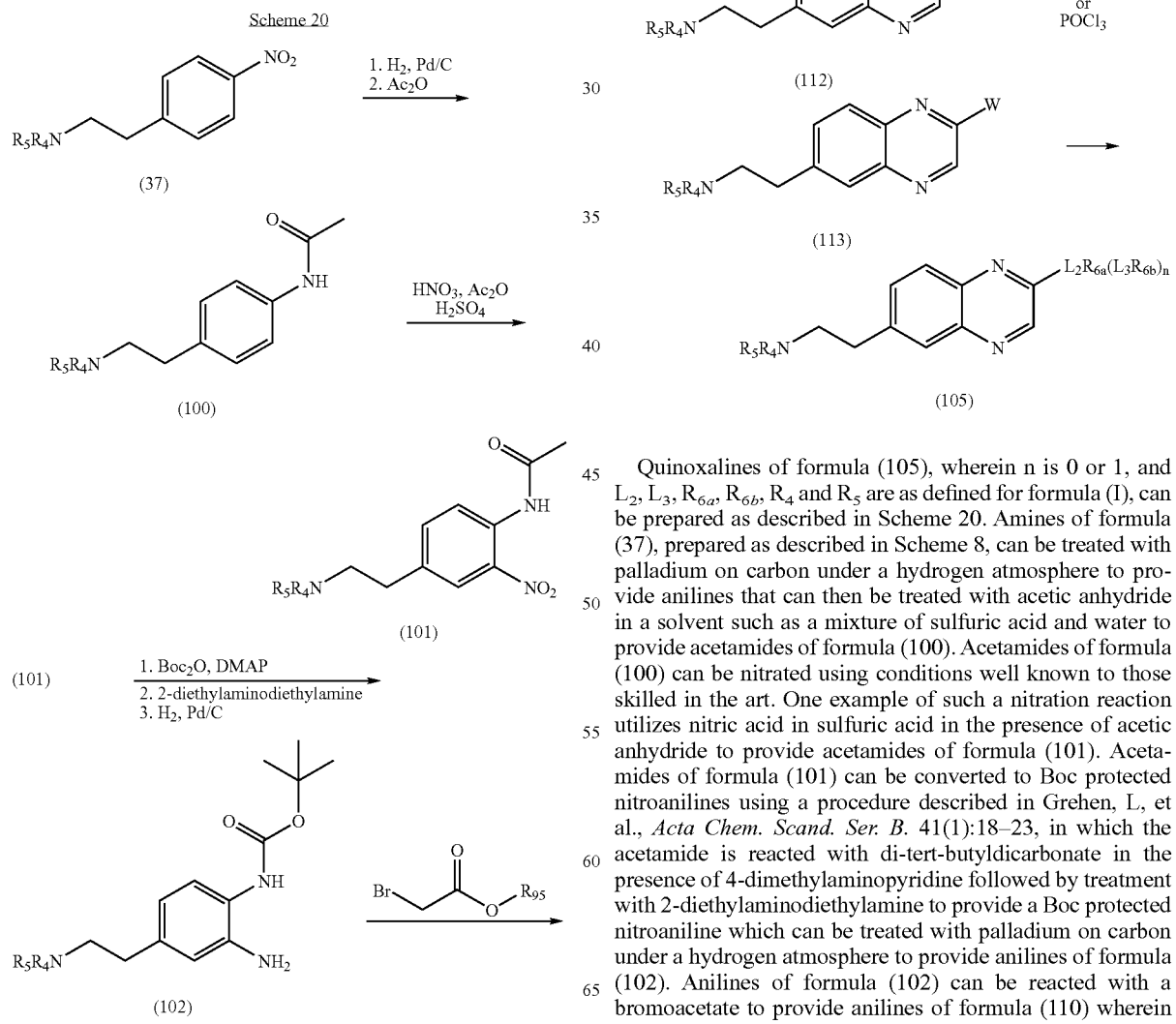

Quinoxalines of formula (105), wherein n is 0 or 1, and $L_2$, $L_3$, $R_{6a}$, $R_{6b}$, $R_4$ and $R_5$ are as defined for formula (I), can be prepared as described in Scheme 20. Amines of formula (37), prepared as described in Scheme 8, can be treated with palladium on carbon under a hydrogen atmosphere to provide anilines that can then be treated with acetic anhydride in a solvent such as a mixture of sulfuric acid and water to provide acetamides of formula (100). Acetamides of formula (100) can be nitrated using conditions well known to those skilled in the art. One example of such a nitration reaction utilizes nitric acid in sulfuric acid in the presence of acetic anhydride to provide acetamides of formula (101). Acetamides of formula (101) can be converted to Boc protected nitroanilines using a procedure described in Grehen, L, et al., Acta Chem. Scand. Ser. B. 41(1):18–23, in which the acetamide is reacted with di-tert-butyldicarbonate in the presence of 4-dimethylaminopyridine followed by treatment with 2-diethylaminodiethylamine to provide a Boc protected nitroaniline which can be treated with palladium on carbon under a hydrogen atmosphere to provide anilines of formula (102). Anilines of formula (102) can be reacted with a bromoacetate to provide anilines of formula (110) wherein $R_{95}$ is alkyl. Anilines of formula (110) can be treated with an acid such as, but not limited to, trifluoroacetic acid with heating to provide dihydroquinoxalinones of formula (111). Dihydroquinoxalinones of formula (111) can be oxidized using an oxidizing agent such as, but not limited to, silver nitrate to provide quinoxalinones of formula (112). Quinoxalinones of formula (112) can be treated with triflouroacetic anhydride in the presence of a base such as 2,6-lutidine in a solvent such as dichloromethane to provide compounds of structure (113) wherein W is triflate. Alternatively, quinoxalinones of formula (112) can be treated with POCl₃ to provide compounds of structure (113) wherein W is Cl. Compounds of formula (113) can be processed as described in Schemes 1, 2, and 4 to provide quinoxalines of formula (105) wherein n is 1.

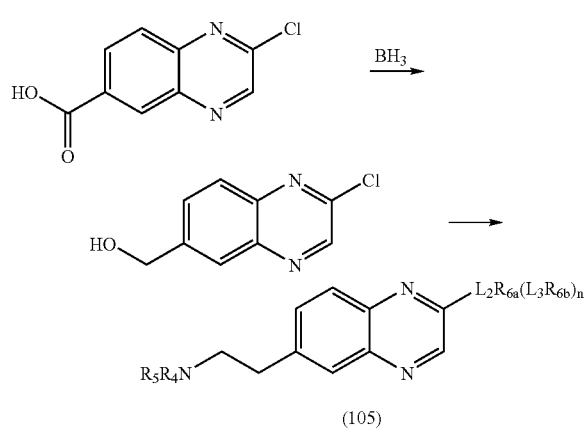

Quinoxalines of formula (105), wherein n is 0 or 1, and $L_2$, $L_3$, $R_{6a}$, $R_{6b}$, $R_4$ and $R_5$ are as defined in formula (I), can be prepared as described in Scheme 21. 2-Chloro-quinoxaline-6-carboxylic acid (Wolf et al. J. Amer. Chem. Soc. 71:6–10 (1949)) can be reduced to (2-chloro-quinoxalin-6-yl)-methanol using a reducing agent such as, but not limited to, borane-THF complex. (2-Chloro-quinoxalin-6-yl)-methanol can be processed as described in Schemes 5 to provide quinoxalines of formula (105) wherein n is 1.

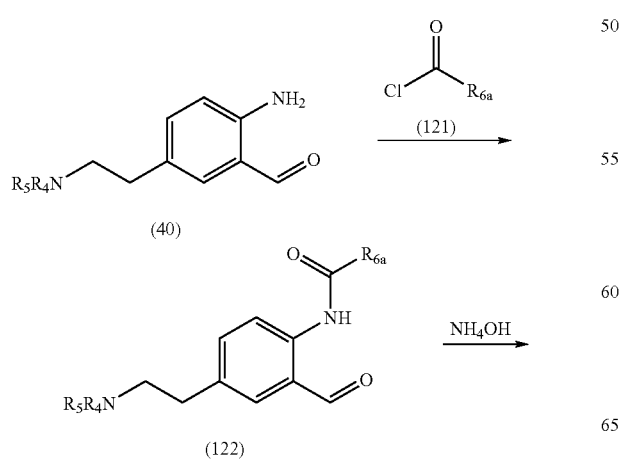

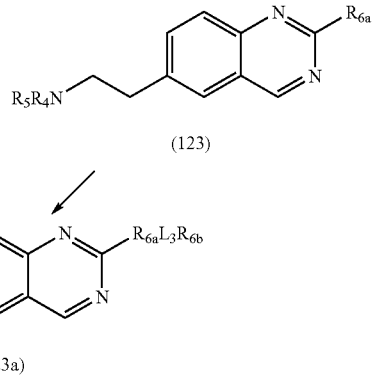

Quinazolines of formula (123a), wherein $L_3$, $R_4$, $R_5$, $R_{6b}$ and $R_{6a}$ are as defined in formula (I), can be prepared as described in Scheme 22. Anilines of formula (40), prepared as described in Scheme 8, can be treated with acid chlorides of formula (121) in the presence of a base such as pyridine in a solvent such as dichloromethane to provide amides of formula (122). Amides of formula (122) can be treated with a source of ammonia, such as aqueous ammonium hydroxide, and heated to provide quinazolines of formula (123). Compounds of formula (123) can be subjected to reaction conditions as outlined in schemes 1, 2, 3, and 4 to provide compounds of formula (123a).

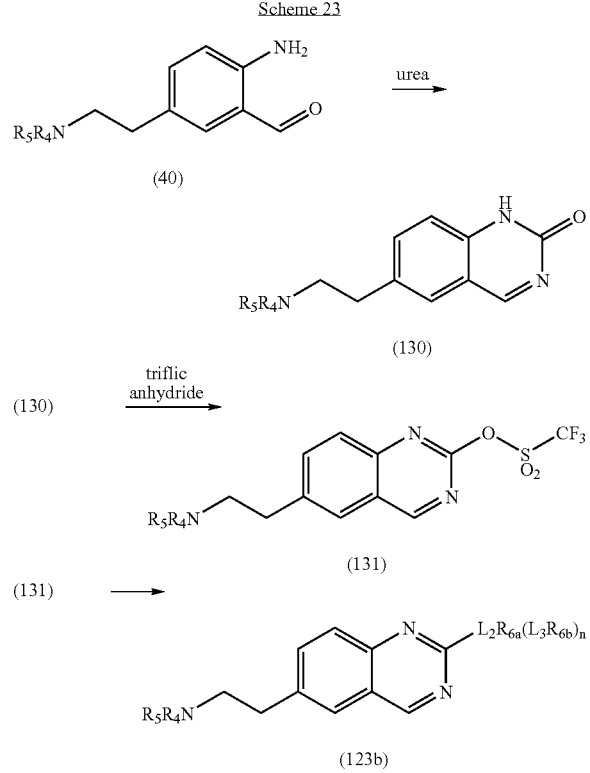

Quinazolines of formula (123b), wherein n is 0 or 1, and $L_2$, $L_3$, $R_{6a}$, $R_4$ and $R_5$ and $R_{6b}$ are as defined in formula (I) can also be prepared as described in Scheme 23. Anilines of formula (40), prepared as described in Scheme 8, can be treated with urea and heated as described in Troeger, et. al., *Prakt. Chem.* 117:181 (1927) to provide quinazolinones of formula (130). Quinazolinones of formula (130) can be treated with triflic anhydride in the presence of a base such as 2,6-lutidine in a solvent such as dichloromethane to provide triflates of general strucure (131). Triflates of formula (131) can be processed as described in Schemes 1, 2, 3 and 4 to provide compounds of formula (123b) wherein n is 1.

Scheme 24

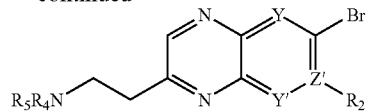

Compounds of formula (144) and (145), wherein n is 0 or 1, $L_2$, $L_3$, Y, Y', Z', $R_2$, $R_4$, $R_5$, $R_{6a}$ and $R_{6b}$ are as defined in formula (I), can be prepared as described in Scheme 24. Nitrobenzenes of formula (138) can be treated with a reducing agent such as, but not limited to, platinum on carbon under a hydrogen atmosphere to provide diaminobenzenes of formula (139). Diaminobenzenes of formula (139) can be treated with 2-oxopropanal to provide a mixture of bromides of formula (140) and (141). Bromides of formula (140) and (141) can be treated with formaldehyde and amines of formula (5) to provide a mixture of aminobromides of formula (142) and (143). Aminobromides of formula (142) and (143) can be processed as described in Schemes 1, 2, 3 and 4 to provide compounds of formula (144) and (145) wherein n 1.

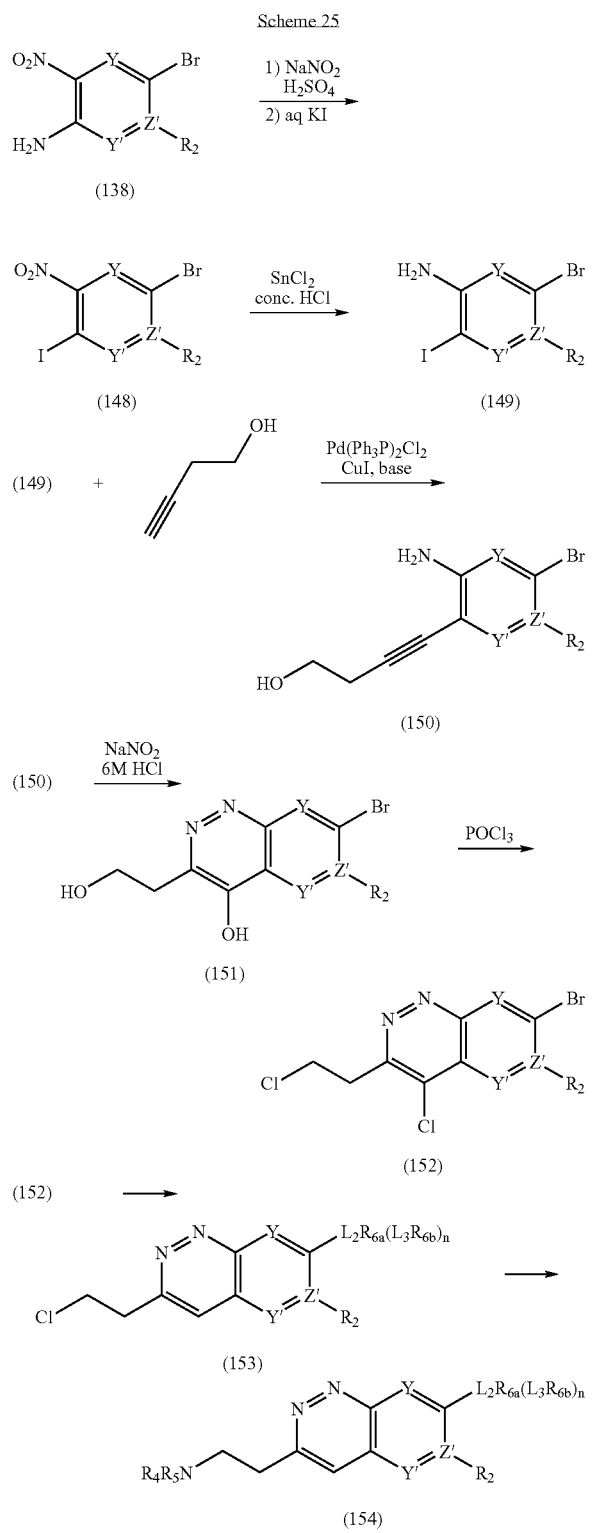

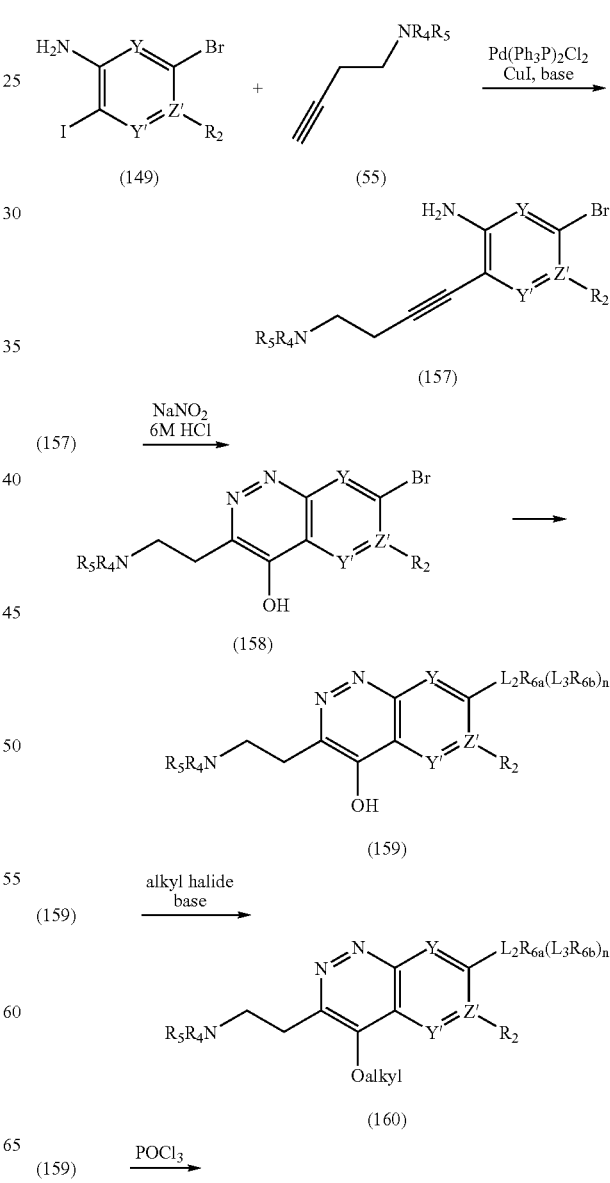

followed by treatment with KI to provide iodo compounds of formula (148). Iodo compounds of formula (148) can be treated with $SnCl_2$ and an acid such as, but not limited, concentrated HCl to provide compounds of formula (149). Compounds of formula (149) can be treated with but-3-yn-1-ol, copper (I) iodide, base such as, but not limited to triethylamine, and a metal catalyst such as but not limited to $PdCl_2(PPh_3)_2$ to provide alkynes of formula (150). Alkynes of formula (150) can be treated with $NaNO_2$ and an acid such as, but not limited to, 6M HCl to provide compounds of formula (151). Compounds of formula (151) can be treated with $POCl_3$ to provide chlorides of formula (152). Chlorides of formula (152) can be processed as described in Schemes 1, 2, 3 and 4 to provide compounds of formula (153). Compounds of formula (153) can be treated with amines of formula (5) to provide compounds of formula (154).

Compounds of formula (154), wherein n is 0 or 1, and Y, Y', Z', $R_2$, $R_4$, $L_2$, $L_3$, $R_{6a}$, $R_{6b}$, and $R_5$ are as defined in formula (I), can be prepared as described in Scheme 25. Compounds of formula (138), purchased or prepared using known methods in the art, can be treated with $NaNO_2$ and an acid, such as, but not limited to, concentrated sulfuric acid

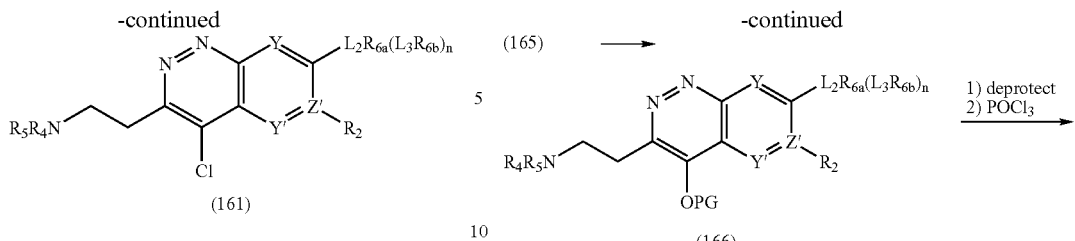

(161)

Compounds of formula (159–161), wherein n is 0 or 1, and Y, Y', Z', $R_2$, $R_4$, $L_2$, $L_3$, $R_{6a}$, $R_{6b}$ and $R_5$ are as defined in formula (I), can be prepared as described in Scheme 26. Compounds of formula (149), can be treated with amines of formula (55), copper (I) iodide, a base such as, but not limited to triethylamine, and a metal catalyst such as, but not limited to, $PdCl_2(PPh_3)_2$ to provide alkynes of formula (157). Alkynes of formula (157) can be treated with $NaNO_2$ and an acid such as, but not limited to, 6 M HCl to provide compounds of formula (158). Compounds of formula (158) can be processed as described in Schemes 1, 2, 3 and 4 to provide compounds of formula (159). Compounds of formula (159) can be treated with an alkyl halide such as, but not limited to, iodomethane or iodoethane and a base such as, but not limited to, triethylamine or NaH to provide compounds of formula (160). Compounds of formula (159) can be treated with phosphorus oxychloride to provide chlorides of formula (161), phosphorus oxybromide may also be used to generate the corresponding bromides.

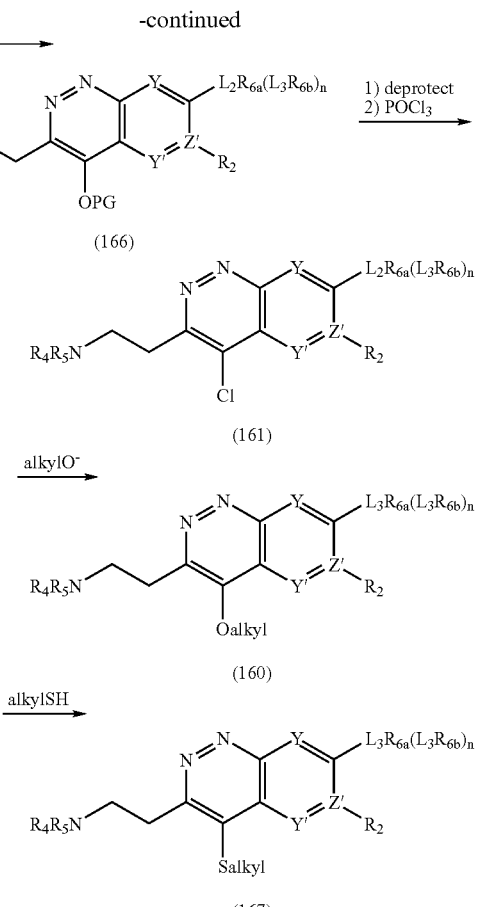

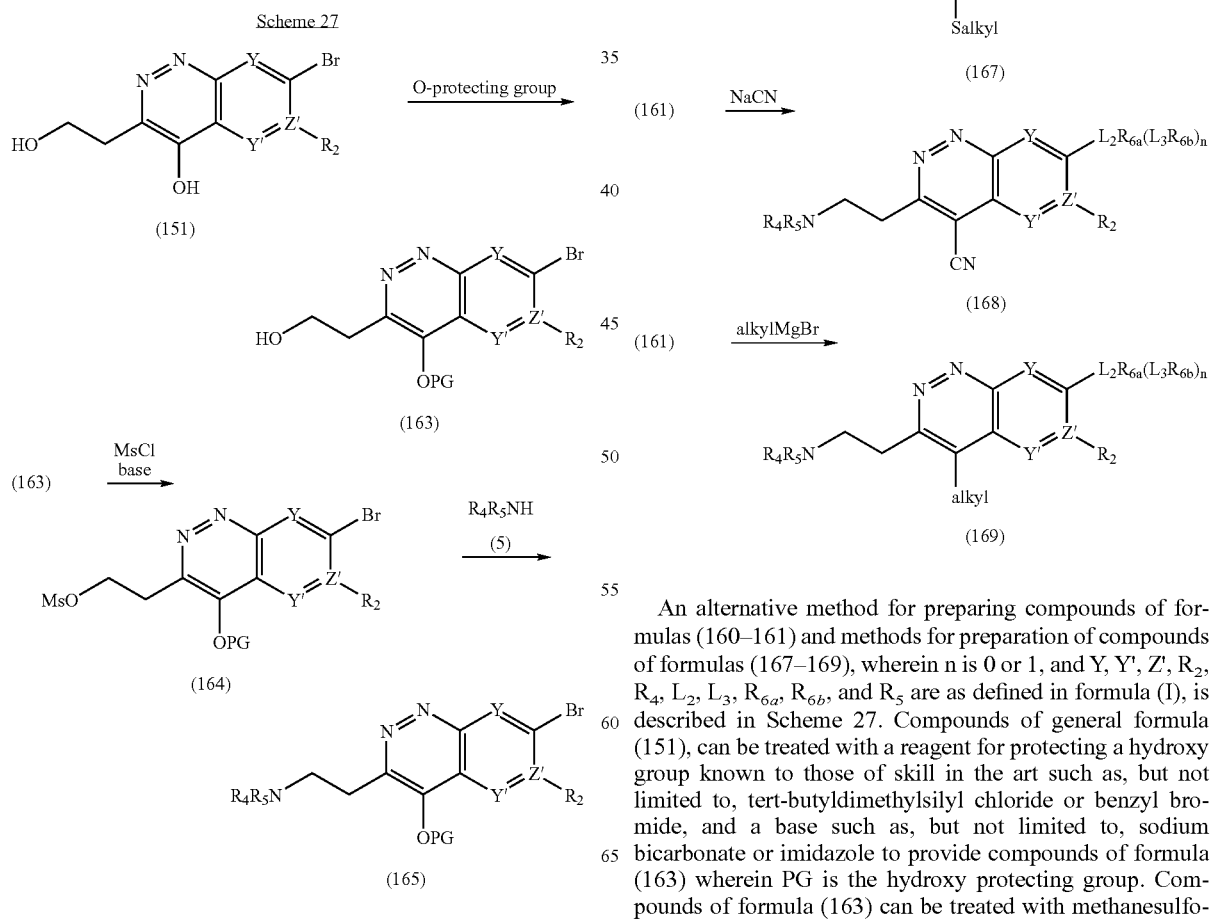

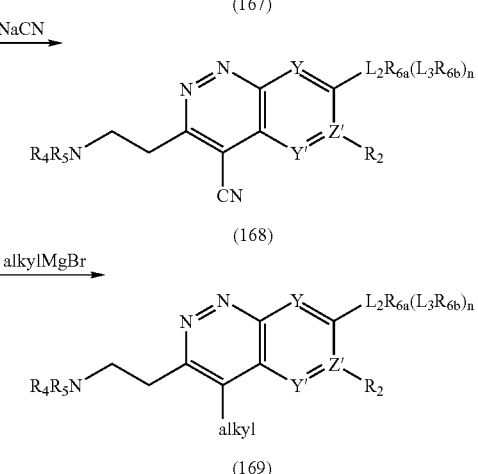

An alternative method for preparing compounds of formulas (160–161) and methods for preparation of compounds of formulas (167–169), wherein n is 0 or 1, and Y, Y', Z', $R_2$, $R_4$, $L_2$, $L_3$, $R_{6a}$, $R_{6b}$, and $R_5$ are as defined in formula (I), is described in Scheme 27. Compounds of general formula (151), can be treated with a reagent for protecting a hydroxy group known to those of skill in the art such as, but not limited to, tert-butyldimethylsilyl chloride or benzyl bromide, and a base such as, but not limited to, sodium bicarbonate or imidazole to provide compounds of formula (163) wherein PG is the hydroxy protecting group. Compounds of formula (163) can be treated with methanesulfonyl chloride (or toluenesulfonyl chloride) and a base such as, but not limited to, diisopropylamine or triethylamine to provide sulfonates of formula (164). Sulfonates of formula (164) can be treated with amines of formula (5) to provide compounds of formula (165). Compounds of formula (165) can be processed as described in Schemes 1, 2, 3 and 4 to provide compounds of formula (166). The hydroxy protecting group of compounds of formula (166) can be removed using methods known to those in the art such as, but not limited to, treatment with fluoride ion, acid, or hydrogenation in the presence of a metal catalyst ($H_2$ and Pd/C) followed by treatment with phosphorus oxychloride to provide chlorides of formula (161), phosphorus oxybromide may also be used to generate the corresponding bromides. Chlorides of formula (161) can be treated with nucleophiles such as, but not limited to, alkoxides, alkyl mercaptans, alkyl Grignards, or sodium cyanide to provide compounds of formula 160 and 167–169.

The compounds and intermediates of the invention may be isolated and purified by methods well-known to those skilled in the art of organic synthesis.

Examples of conventional methods for isolating and purifying compounds can include, but are not limited to, chromatography on solid supports such as silica gel, alumina, or silica derivatized with alkylsilane groups, by recrystallization at high or low temperature with an optional pretreatment with activated carbon, thin-layer chromatography, distillation at various pressures, sublimation under vacuum, and trituration, as described for instance in "Vogel's Textbook of Practical Organic Chemistry", 5th edition (1989), by Furniss, Hannaford, Smith, and Tatchell, pub. Longman Scientific & Technical, Essex CM20 2JE, England.

The compounds of the invention have at least one basic nitrogen whereby the compound can be treated with an acid to form a desired salt. For example, a compound may be reacted with an acid at or above room temperature to provide the desired salt, which is deposited, and collected by filtration after cooling. Examples of acids suitable for the reaction include, but are not limited to tartaric acid, lactic acid, succinic acid, as well as mandelic, atrolactic, methanesulfonic, ethanesulfonic, toluenesulfonic, naphthalenesulfonic, carbonic, fumaric, gluconic, acetic, propionic, salicylic, hydrochloric, hydrobromic, phosphoric, sulfuric, citric, or hydroxybutyric acid, camphorsulfonic, malic, phenylacetic, aspartic, glutamic, and the like.

Compositions of the Invention

The invention also provides pharmaceutical compositions comprising a therapeutically effective amount of a compound of formula (I) in combination with a pharmaceutically acceptable carrier. The compositions comprise compounds of the invention formulated together with one or more non-toxic pharmaceutically acceptable carriers. The pharmaceutical compositions can be formulated for oral administration in solid or liquid form, for parenteral injection or for rectal administration.

The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of one skilled in the art of formulations.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally," as used herein, refers to modes of administration which include intravenous, intramuscular, intraperitoneal, intrasternal, subcutaneous, intraarticular injection and infusion.

Pharmaceutical compositions for parenteral injection comprise pharmaceutically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propylene glycol, polyethylene glycol, glycerol, and the like, and suitable mixtures thereof, vegetable oils (such as olive oil) and injectable organic esters such as ethyl oleate, or suitable mixtures thereof. Suitable fluidity of the composition may be maintained, for example, by the use of a coating such as lecithin, by the maintenance of the required particle size in the case of dispersions, and by the use of surfactants.

These compositions may also contain adjuvants such as preservative agents, wetting agents, emulsifying agents, and dispersing agents. Prevention of the action of microorganisms may be ensured by various antibacterial and antifungal agents, for example, parabens, chlorobutanol, phenol, sorbic acid, and the like. It may also be desirable to include isotonic agents, for example, sugars, sodium chloride and the like. Prolonged absorption of the injectable pharmaceutical form may be brought about by the use of agents delaying absorption, for example, aluminum monostearate and gelatin.

In some cases, in order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Suspensions, in addition to the active compounds, may contain suspending agents, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

If desired, and for more effective distribution, the compounds of the invention can be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides) Depot injectable formulations also are prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions may be formulated according to the known art using suitable dispersing or welting agents and suspending agents. The sterile injectable preparation may also be a sterile injectable solution, suspension or emulsion in a nontoxic, parenterally acceptable diluent or solvent such as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Solid dosage forms for oral administration include capsules, tablets, pills, powders, and granules. In such solid dosage forms, one or more compounds of the invention is mixed with at least one inert pharmaceutically acceptable carrier such as sodium citrate or dicalcium phosphate and/or a) fillers or extenders such as starches, lactose, sucrose, glucose, mannitol, and salicylic acid; b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using lactose or milk sugar as well as high molecular weight polyethylene glycols.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract in a delayed manner. Examples of materials which can be useful for delaying release of the active agent can include polymeric substances and waxes.

Compositions for rectal or vaginal administration are preferably suppositories which can be prepared by mixing the compounds of this invention with suitable non-irritating carriers such as cocoa butter, polyethylene glycol or a suppository wax which are solid at ambient temperature but liquid at body temperature and therefore melt in the rectum or vaginal cavity and release the active compound.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Dosage forms for topical or transdermal administration of a compound of this invention include ointments, pastes, creams, lotions, gels, powders, solutions, sprays, inhalants or patches. A desired compound of the invention is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, lactose, talc, silicic acid, aluminum hydroxide, calcium silicates and polyamide powder, or mixtures of these substances. Sprays can additionally contain customary propellants such as chlorofluorohydrocarbons.

Compounds of the invention may also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes may be used. The present compositions in liposome form may contain, in addition to the compounds of the invention, stabilizers, preservatives, and the like. The preferred lipids are the natural and synthetic phospholipids and phosphatidylcholines (lecithins) used separately or together.

Methods to form liposomes are known in the art. See, for example, Prescott, Ed., Methods in Cell Biology, Volume XIV, Academic Press, New York, N.Y., (1976), p 33 et seq.

Dosage forms for topical administration of a compound of this invention include powders, sprays, ointments and inhalants. The active compound is mixed under sterile conditions with a pharmaceutically acceptable carrier and any needed preservatives, buffers or propellants, which can be required. Opthalmic formulations, eye ointments, powders and solutions are contemplated as being within the scope of this invention. Aqueous liquid compositions comprising compounds of the invention also are contemplated.

The compounds of the invention can be used in the form of pharmaceutically acceptable salts, esters, or amides derived from inorganic or organic acids. The term "pharmaceutically acceptable salts, esters and amides," as used herein, refer to carboxylate salts, amino acid addition salts, zwitterions, esters and amides of compounds of formula (I) which are, within the scope of sound medical judgment, suitable for use in contact with the tissues of humans and lower animals without undue toxicity, irritation, allergic response, and the like, are commensurate with a reasonable benefit/risk ratio, and are effective for their intended use.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well-known in the art. The salts can be prepared in situ during the final isolation and purification of the compounds of the invention or separately by reacting a free base function with a suitable organic acid.

Representative acid addition salts include, but are not limited to, acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate. Preferred salts of the compounds of the invention are the tartrate and hydrochloride salts.

Also, the basic nitrogen-containing groups can be quaternized with such agents as lower alkyl halides such as methyl, ethyl, propyl, and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; arylalkyl halides such as benzyl and phenethyl bromides and others. Water or oil-soluble or dispersible products are thereby obtained.

Examples of acids which can be employed to form pharmaceutically acceptable acid addition salts include such inorganic acids as hydrochloric acid, hydrobromic acid, sulphuric acid and phosphoric acid and such organic acids as oxalic acid, maleic acid, succinic acid, and citric acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium, and aluminum salts, and the like, and nontoxic quaternary ammonia and amine cations including ammonium, tetramethylammonium, tetraethylammonium, methylamine, dimethylamine, trimethylamine, triethylamine, diethylamine, ethylamine and the such as. Other representative organic amines useful for the formation of base addition salts include ethylenediamine, ethanolamine, diethanolamine, piperidine, and piperazine.

The term "pharmaceutically acceptable ester," as used herein, refers to esters of compounds of the invention which hydrolyze in vivo and include those that break down readily in the human body to leave the parent compound or a salt thereof. Examples of pharmaceutically acceptable, non-toxic esters of the invention include $C_1$- to-$C_6$ alkyl esters and $C_5$- to-$C_7$ cycloalkyl esters, although $C_1$- to-$C_4$ alkyl esters are preferred. Esters of the compounds of formula (I) may be prepared according to conventional methods. For example, such esters may be appended onto hydroxy groups by reaction of the compound that contains the hydroxy group with acid and an alkylcarboxylic acid such as acetic acid, or with acid and an arylcarboxylic acid such as benzoic acid. In the case of compounds containing carboxylic acid groups, the pharmaceutically acceptable esters are prepared from compounds containing the carboxylic acid groups by reaction of the compound with base such as triethylamine and an alkyl halide, alkyl triflate, for example with methyliodide, benzyl iodide, cyclopentyl iodide. They also may be prepared by reaction of the compound with an acid such as hydrochloric acid and an alkylcarboxylic acid such as acetic acid, or with acid and an arylcarboxylic acid such as benzoic acid.

The term "pharmaceutically acceptable amide," as used herein, refers to non-toxic amides of the invention derived from ammonia, primary $C_1$- to-$C_6$ alkyl amines and secondary $C_1$- to-$C_6$ dialkyl amines. In the case of secondary amines, the amine may also be in the form of a 5- or 6-membered heterocycle containing one nitrogen atom. Amides derived from ammonia, $C_1$- to-$C_3$ alkyl primary amides and $C_1$- to-$C_2$ dialkyl secondary amides are preferred. Amides of the compounds of formula (I) may be prepared according to conventional methods. Pharmaceutically acceptable amides are prepared from compounds containing primary or secondary amine groups by reaction of the compound that contains the amino group with an alkyl anhydride, aryl anhydride, acyl halide, or aryl halide. In the case of compounds containing carboxylic acid groups, the pharmaceutically acceptable esters are prepared from compounds containing the carboxylic acid groups by reaction of the compound with base such as triethylamine, a dehydrating agent such as dicyclohexyl carbodiimide or carbonyl diimidazole, and an alkyl amine, dialkylamine, for example with methylamine, diethylamine, piperidine. They also may be prepared by reaction of the compound with an acid such as sulfuric acid and an alkylcarboxylic acid such as acetic acid, or with acid and an arylcarboxylic acid such as benzoic acid under dehydrating conditions as with molecular sieves added. The composition can contain a compound of the invention in the form of a pharmaceutically acceptable prodrug.

The term "pharmaceutically acceptable prodrug" or "prodrug," as used herein, represents those prodrugs of the compounds of the invention which are, within the scope of sound medical judgment, suitable for use in contact with the tissues of humans and lower animals without undue toxicity, irritation, allergic response, and the like, commensurate with a reasonable benefit/risk ratio, and effective for their intended use. Prodrugs of the invention may be rapidly transformed in vivo to a parent compound of formula (I), for example, by hydrolysis in blood. A thorough discussion is provided in T. Higuchi and V. Stella, Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987), hereby incorporated by reference.

The invention contemplates pharmaceutically active compounds either chemically synthesized or formed by in vivo biotransformation to compounds of formula (I).

Methods of the Invention

Compounds and compositions of the invention are useful for modulating the effects of histamine-3 receptors. In particular, the compounds and compositions of the invention can be used for treating and preventing disorders modulated by the histamine-3 receptors. Typically, such disorders can be ameliorated by selectively modulating the histamine-3 receptors in a mammal, preferably by administering a compound or composition of the invention, either alone or in combination with another active agent as part of a therapeutic regimen.

The compounds of the invention, including but not limited to those specified in the examples, possess an affinity for the histamine-3 receptors. As histamine-3 receptor ligands, the compounds of the invention may be useful for the treatment and prevention of diseases or conditions such as acute myocardial infarction, Alzheimer's disease, asthma, attention-deficit hyperactivity disorder, bipolar disorder, cognitive dysfunction, cognitive deficits in psychiatric disorders, deficits of memory, deficits of learning, dementia, cutaneous carcinoma, drug abuse, diabetes, type II diabetes, depression, epilepsy, gastrointestinal disorders, inflammation, insulin resistance syndrome, jet lag, medullary thyroid carcinoma, melanoma, Meniere's disease, metabolic syndrome, mild cognitive impairment, migraine, mood and attention alteration, motion sickness, narcolepsy, neurogenic inflammation, obesity, obsessive compulsive disorder, pain, Parkinson's disease, polycystic ovary syndrome, schizophrenia, cognitive deficits of schizophrenia, seizures, septic shock, Syndrome X, Tourette's syndrome, vertigo, and sleep disorders.

The ability of the compounds of the invention, including, but not limited to, those specified in the examples, to treat septic shock and cardiovascular disorders, in particular, acute myocardial infarction may be demonstrated by Imamura et al., Circ. Res., 78:475–481 (1996); Imamura et. al., Circ. Res., 78:863–869 (1996); R. Levi and N. C. E. Smith, "Histamine $H_3$-receptors: A new frontier in myocardial ischemia", J. Pharm. Exp. Ther., 292:825–830 (2000); and Hatta, E., K. Yasuda and R. Levi, "Activation of histamine $H_3$ receptors inhibits carrier-mediated norepinephrine release in a human model of protracted myocradial ischemia", J. Pharm. Exp. Ther., 283:494–500 (1997).

The ability of the compounds of the invention, including, but not limited to, those specified in the examples, to treat sleep disorders, in particular, narcolepsy may be demonstrated by Lin et al., Brain Res., 523:325–330 (1990); Monti, et al., Neuropsychopharmacology 15:31–35 (1996); Sakai, et al., Life Sci., 48:2397–2404 (1991); Mazurkiewicz-Kwilecki and Nsonwah, Can. J. Physiol. Pharmacol., 67:75–78 (1989); P. Panula, et al., Neuroscience 44:465–481 (1998); Wada, et al., Trends in Neuroscience 14:415 (1991); and Monti, et al., Eur. J. Pharmacol. 205:283 (1991).

The ability of the compounds of the invention, including, but not limited to, those specified in the examples, to treat cognition and memory process disorders may be demonstrated by Mazurkiewicz-Kwilecki and Nsonwah, Can. J. Physiol. Pharmacol., 67:75–78 (1989); P. Panula, et al., Neuroscience, 82:993–997 (1997); Haas, et al., Behav. Brain Res., 66:41–44 (1995); De Almeida and Izquierdo, Arch. Int. Pharmacodyn., 283:193–198 (1986); Kamei et al., Psychopharmacology, 102:312–318 (1990); Kamei and Sakata, Jpn. J. Pharmacol., 57:437–482 (1991); Schwartz et al., Psychopharmacology, The fourth Generation of Progress. Bloom and Kupfer (eds). Raven Press, New York, (1995) 397; and Wada, et al., Trends in Neurosci., 14:415 (1991).

The ability of the compounds of the invention, including, but not limited to, those specified in the examples, to treat attention-deficit hyperactivity disorder (ADHD) may be demonstrated by Shaywitz et al., Psychopharmacology, 82:73–77 (1984); Dumery and Blozovski, Exp. Brain Res., 67:61–69 (1987); Tedford et al., J. Pharmacol. Exp. Ther., 275:598–604 (1995); Tedford et al., Soc. Neurosci. Abstr., 22:22 (1996); and Fox, et al., Behav. Brain Res., 131: 151–161 (2002).

The ability of the compounds of the invention, including, but not limited to, those specified in the examples, to treat seizures, in particular, epilepsy may be demonstrated by Yokoyama, et al., Eur. J. Pharmacol., 234:129 (1993); Yokoyama and Iinuma, CNS Drugs 5:321 (1996); Onodera et al., Prog. Neurobiol., 42:685 (1994); R. Leurs, R. C. Vollinga and H. Timmerman, "The medicinal chemistry and therapeutic potential of ligands of the histamine $H_3$ receptor", Progress in Drug Research 45:170–165, (1995); Leurs and Timmerman, Prog. Drug Res., 39:127 (1992); The Histamine $H_3$ Receptor, Leurs and Timmerman (eds), Elsevier Science, Amsterdam, The Netherlands (1998); and H. Yokoyama and K. Iinuma, "Histamine and Seizures: Implications for the treatment of epilepsy", CNS Drugs, 5(5):321–330 (1995)

The ability of the compounds of the invention, including, but not limited to, those specified in the examples, to treat motion sickness, Alzheimer's disease, and Parkinson's disease may be demonstrated by Onodera, et al., Prog. Neurobiol., 42:685 (1994); Leurs and Timmerman, Prog. Drug Res., 39:127 (1992); and The Histamine $H_3$ Receptor, Leurs and Timmerman (eds), Elsevier Science, Amsterdam, The Netherlands (1998).

The ability of the compounds of the invention, including, but not limited to, those specified in the examples, to treat narcolepsy, schizophrenia, depression, and dementia may be demonstrated by R. Leurs, R. C. Vollinga and H. Timmerman, "The medicinal chemistry and therapeutic potential of ligands of the histamine $H_3$ receptor", Progress in Drug Research 45:170–165 (1995); The Histamine $H_3$ Receptor, Leurs and Timmerman (eds), Elsevier Science, Amsterdam, The Netherlands (1998); and Perez-Garcia C, et. al., and Psychopharmacology (Berl) 142(2):215–20 (February, 1999).

The ability of the compounds of the invention, including, but not limited to, those specified in the examples, to treat sleep disorders, cognitive dysfunction, mood and attention alteration, vertigo and motion sickness, and treatment of cognitive deficits in psychiatric disorders may be demonstrated by Schwartz, Physiol. Review 71:1–51 (1991).

The ability of the compounds of the invention, including, but not limited to, those specified in the examples, to treat mild cognitive impairment, deficits of memory, deficits of learning and dementia may be demonstrated by C. E. Tedford, in "The Histamine $H_3$ Receptor: a target for new drugs", the Pharmacochemistry Library, vol. 30 (1998) edited by R. Leurs and H. Timmerman, Elsevier (New York). p. 269 and references also contained therein.

The ability of the compounds of the invention, including, but not limited to, those specified in the examples, to treat obesity may be demonstrated by Leurs, et al., Trends in Pharm. Sci., 19:177–183 (1998); E. Itoh, M. Fujimiay, and A. Inui, "Thioperamide, A histamine $H_3$ receptor antagonist, powerfully suppresses peptide YY-induced food intake in rats," Biol. Psych., 45(4):475-481 (1999); S. I. Yates, et al., "Effects of a novel histamine $H_3$ receptor antagonist, GT-2394, on food intake and weight gain in Sprague-Dawley rats," Abstracts, Society for Neuroscience, 102.10:

219 (November, 2000); and C. Bjenning, et al., "Peripherally administered ciproxifan elevates hypothalamic histamine levels and potently reduces food intake in the Sprague Dawley rat," Abstracts, International Sendai Histamine Symposium, Sendai, Japan, #P39 (November, 2000).

The ability of the compounds of the invention, including, but not limited to, those specified in the examples, to treat inflammation and pain may be demonstrated by Phillips, et al., Annual Reports in Medicinal Chemistry 33:31–40 (1998).

The ability of the compounds of the invention, including, but not limited to, those specified in the examples, to treat migraine may be demonstrated by R. Leurs, R. C. Vollinga and H. Timmerman, "The medicinal chemistry and therapeutic potential of ligands of the histamine $H_3$ receptor," Progress in Drug Research 45:170–165 (1995); Matsubara, et al., Eur. J. Pharmacol., 224:145 (1992); and Rouleau, et al., J. Pharmacol. Exp. Ther., 281:1085 (1997).

The ability of the compounds of the invention, including, but not limited to, those specified in the examples, to treat cancer, in particular, melanoma, cutaneous carcinoma and medullary thyroid carcinoma may be demonstrated by Adam Szelag, "Role of histamine $H_3$-receptors in the proliferation of neoplastic cells in vitro," Med. Sci. Monit., 4(5):747–755 (1998); and C. H. Fitzsimons, et al., "Histamine receptors signalling in epidermal tumor cell lines with H-ras gene alterations," Inflammation Res., 47 (Suppl 1):S50-S51 (1998).

The ability of the compounds of the invention, including, but not limited to, those specified in the examples, to treat vestibular dysfunctions, in particular, Meniere's disease may be demonstrated by R. Leurs, R. C. Vollinga and H. Timmerman, "The medicinal chemistry and therapeutic potential of ligands of the histamine $H_3$ receptor," Progress in Drug Research 45:170–165 (1995), and Pan, et al., Methods and Findings in Experimental and Chemical Pharmacology 21:771–777 (1998).

The ability of the compounds of the invention, including, but not limited to, those specified in the examples, to treat asthma may be demonstrated by A. Delaunois A., et al., "Modulation of acetylcholine, capsaicin and substance P effects by histamine $H_3$ receptors in isolated perfused rabbit lungs," European Journal of Pharmacology 277(2–3):243–250 (1995); and Dimitriadou, et al., "Functional relationship between mast cells and C-sensitive nerve fibres evidenced by histamine $H_3$-receptor modulation in rat lung and spleen," Clinical Science 87(2):151–163 (1994).

The ability of the compounds of the invention, including, but not limited to, those specified in the examples, to treat allergic rhinitis may be demonstrated by McLeod, et al., Progress in Resp. Research 31:133 (2001).

Compounds of the invention are particularly useful for treating and preventing a condition or disorder affecting the memory or cognition, for example Alzheimer's disease, attention-deficit hyperactivity disorder, schizophrenia, or the cognitive deficits of schizophrenia.

Actual dosage levels of active ingredients in the pharmaceutical compositions of this invention can be varied so as to obtain an amount of the active compound(s) which is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

When used in the above or other treatments, a therapeutically effective amount of one of the compounds of the invention can be employed in pure form or, where such forms exist, in pharmaceutically acceptable salt, ester, amide or prodrug form. Alternatively, the compound can be administered as a pharmaceutical composition containing the compound of interest in combination with one or more pharmaceutically acceptable carriers. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or lower animal may range from about 0.0003 to about 30 mg/kg/day. For purposes of oral administration, more preferable doses can be in the range of from about 0.01 to about 0.1 mg/kg/day. If desired, the effective daily dose can be divided into multiple doses for purposes of administration; consequently, single dose compositions may contain such amounts or submultiples thereof to make up the daily dose.

The compounds and processes of the invention will be better understood by reference to the following examples, which are intended as an illustration of and not a limitation upon the scope of the invention.

REFERENCE EXAMPLES

Reference Example 1

Preparation of (2R)-2-methylpyrrolidine and (2S)-2-methylpyrrolidine (2R)-2-Methylpyrrolidine tartrate was prepared via resolution of 2-methylpyrrolidine with D-tartaric acid using procedures described by William Gaffield, et al. in Tetrahedron, 37:1861–1869 (1981) or, alternatively, prepared from L-prolinol by methods described by Karrer and Ehrhardt in Helv. Chim. Acta, 34: 2202, 2208 (1951). (2R)-2-methylpyrrolidine hydrobromide also is a suitable source of (2R)-2-methylpyrrolidine, and was prepared using the procedure described by Nijhuis, Walter H. N., et al., J. Org. Chem., 54(1): 209–216, 214 (1989). Other procedures describing the synthesis of (2R)-2-methylpyrrolidine and salts thereof can be found in Andres, Jose M., et al. Eur. J. Org. Chem., 9:1719–1726 (2000); and Elworthy, Todd R.; Meyers, A. I., Tetrahedron, 50(20): 6089–6096 (1994).

(2S)-2-Methylpyrrolidine can be substituted for (2R)-2-methylpyrrolidine in the experimental procedures provided herein. The (2S)-2-methylpyrrolidine can be prepared by procedures described in Kim, Mahn-Joo, et al., Bioorg. Med. Chem. Lett. 6(1):71–76 (1996).

Reference Example 2

Preparation of Boronic Acid and Ester Reagents

There are many aryl, heteroaryl, and heterocyclic boronic acids and boronic acid esters that are available commercially or that can be prepared as described in the scientific literature of synthetic organic chemistry. Non-exhaustive examples of boronic acid and boronic acid ester reagents for the synthesis of compounds of formula (I) are provided in Table 1, below, and the following description.

TABLE 1

Examples of Boronic Acid and Boronic Acid Ester Reagents

| Boronic Acid or Boronic Acid Ester | Commercial Source, Chemical Abstracts Number or Literature Reference |
| --- | --- |
| 5-(4,4,5,5-tetramethyl-1,3,2-dioxaborolan-2-yl)-2,2'-bithiophene | Cat # 132898-95-4, Sigma-Aldrich, St. Louis, MO |
| 4-[4-(4,4,5,5-tetramethyl-1,3,2-dioxaborolan-2-yl)phenyl]morpholine | Cat # CC17439CB, Acros Organics USA |
| 3-(morpholine-4-carbonyl)phenylboronic acid | Catalog # BB-3054, Combi-Blocks Inc., San Diego, CA |

Boronic acid esters of formula (14),

(14)

wherein $L_2$ is a bond, and wherein $R_{94}$ is lower alkyl or wherein $R_{94}$ can be taken together to form a ring which may itself be substituted with alkyl or aryl groups, may serve as synthetic replacements for boronic acids of formula (14), wherein $R_{94}$ is hydrogen. Boronic acids of formula (14) and boronic acid esters of formula (14) are commercially available or can be prepared by methods well known to those skilled in the art of synthetic organic chemistry. For instance, Takagi et al. (Tetrahedron Letters, 43:5649–5651 (2002)) prepared heteroaryl pinacolborane esters of using heteroaromatic compounds and reaction with bis(pinacolborane) in the presence of an iridium catalysis of IrCl[COD]2-(4,4'-di-t-butyl-2,2'-bipyridine in octane. Other methods have been described wherein aryl halides and heteroaryl halides are transmetallated with alkyl lithiums or Grignard reagents, then treated with trialkylborate esters, then treated with acid to produce boronic acids and boronic acid esters (B. T. O'Neill, et al., Organic Letters, 2:4201 (2000); M. D. Sindkhedkar, et al., Tetrahedron, 57:2991 (2001); W. C. Black, et al., Journal of Medicinal Chemistry, 42:1274 (1999); Letsinger; Dandegaonker, J. Amer. Chem. Soc., 81:498–501 (1959); Carroll, F. Ivy, et al. J. Med. Chem., 2229–2237 (2001). Another method is the Miyaura reaction described in Ishiyama, Tatsuo; Ishida, Kousaku, Miyaura, Norio, Tetrahedron, 9813–9816 (2001) in which aryl and heteroaryl halides are reacted with bis(pinacolborane), KOAc, and Pd$_2$ dba$_3$ and tris-cyclohexylphosphine or PdCl$_2$dppf (Ishiyama, et al. Tetrahedron, 9813–9816 (2001)). Another method for preparation of boronic acids and boronic acid esters is the reaction described in O. Baudoin, et al., J. Org. Chem., 65:9268–9271 (2000), in which aryl and heteroaryl halides or triflates are reacted with a dialkoxyborane such as pinacolborane, in the presence of Et$_3$N and Pd(OAc)$_2$ in dioxane. Methodologies for preparing compounds of formula (14) wherein one of the rings of $R_6$ is a cycloalkyl ring can be prepared, for example, from bicyclic or polycyclic compounds wherein one of the rings is a cycloalkene (for example, see H. C. Brown, et al., J. Amer. Chem. Soc., 95:2396–2397 (1973) and H. C. Brown, et al., J. Amer. Chem. Soc., 98:1798–1806 (1976)) or cycloalkyl Grignard or cycloalkyl lithium intermediates (see, for example, Graf et al., Tetrahedron, 55:8801–8814 (1999) and Michailow, et al., Izv. Akad. Nauk SSSR Ser. Khim, 76:78 (1959)).

Reference Example 3

Preparation of Stannane-Type Reagents

Many reagents such as Me$_3$Sn-L$_2$R$_{6a}$(L$_3$R$_{6b}$)$_n$, Bu$_3$Sn-L$_2$R$_{6a}$(L$_3$R$_{6b}$)$_n$, and ZnClZn-L$_2$R$_{6a}$(L$_3$R$_{6b}$)$_n$ are suitable for reactions under Stille conditions in Scheme 1 and are commercially available. However, where the reagents wherein $R_6$ is heteroaryl, heterocyclic, or aryl are not commercially available, they may be prepared by methods available to one with skill in the art. Examples of such methods include lithium halogen-metal exchange of heteroaryl, heterocyclic or aryl halides, followed by treatment with Me$_3$SnCl (Li, et al. J. Med. Chem. 1996, 39, 1846), Bu$_3$SnCl, ZnCl$_2$, or B(OCH$_3$)$_3$ (O'Neill, et al. Org. Lett. 2000, 2, 4201; Sindkhedkar, et al. Tet. 2001, 57, 2991) and magnesium halogen-metal exchange with isopropylmagnesium chloride as described in Knochel, et al. J. Org. Chem. 2000, 65, 4618–4634, followed by treatment with Me$_3$SnCl, Bu$_3$SnCl, or ZnCl$_2$. Heteroaryl halides and triflates can be treated with trimethylstannyl sodium as described in A. O. Koren, et al. J. Med. Chem. 1998, 41, 3690, to give Me$_3$SnR$_6$. Heteroaryl halides and triflates can be treated wtih hexamethyldistannane as described in W. C. Black, et al. J. Med. Chem. 1999, 42, 1274., to give Me$_3$SnR$_6$.

EXAMPLES

Example 1

6-{2-[(2R)-2-methylpyrrolidin-1-yl]ethyl}-2-(4-methyl-2-thien-2-yl-1,3-thiazol-5-yl)quinoline

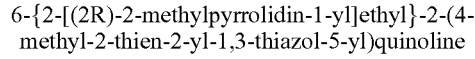

Example 1A (2R)-2-methylpyrrolidine

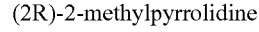

A flask containing 20 mL (20 mmol) of a 1 M solution of LiAlH$_4$ in THF was cooled to 0° C. To this well stirred solution was added 1.35 g (5.0 mmol) of [(2S)-5-oxopyrrolidin-2-yl]methyl 4-methylbenzenesulfonate (CAS #51693-17-5) in 50 mL of THF. The reaction was allowed to warm to 23° C., and stirred for 60 hours, then quenched by slow addition of 3 grams of powdered sodium sulfate decahydrate. After one hour, the solids were removed by filtration, and washed with isopropyl ether. Some loss of solvent to evaporation occurred, so the filtrate and washings were combined and diluted with isopropanol to 50 mL total volume. 40 mL of the solution was treated with 600 mg (4.0 mmol) of L-tartaric acid in methanol. After concentration under vacuum, a syrup was obtained, which solidified on standing, to give a quantitative yield (960 mg) of (2R)-methylpyrrolidine L-tartrate as a white powder.

Example 1B (2R)-2-methyl-1-[2-(4-nitrophenyl)ethyl]pyrrolidine

Example 1A (4.0 g, 17.0 mmol), 1-(2-bromoethyl)-4-nitrobenzene (9.8 g, 43 mmol), and potassium carbonate (12 g, 85 mmol), were combined in DMF (20 mL) in a sealed tube at 50° C. and stirred vigorously for 16 hours. The mixture was allowed to cool to room temperature, diluted with diethyl ether (100 mL), washed with water (2 times, 100 mL and then 50 mL), and extracted with 1M HCl (2 times, 50 mL and 25 mL). The aqueous acidic extractions were combined, washed with diethyl ether (50 mL), cooled to 0° C., adjusted to pH 14 with 50% NaOH solution, and extracted with dichloromethane (3 times, 50 mL). The dichloromethane extractions were combined, dried ($MgSO_4$), filtered, and the filtrate concentrated to provide the title compound. $^1$H NMR (300 MHz, $CDCl_3$) δ 1.08 (d, J=6 Hz, 3H), 1.43 (m, 1H), 1.75 (m, 2H), 1.93 (m, 1H), 2.19 (q, J=9 Hz, 1H), 2.34 (m, 2H), 2.91 (m, 2H), 3.03 (m, 1H), 3.22 (td, J=8, 3 Hz, 1H), 7.38 (d, J=9 Hz, 2H), 8.15 (d, J=9 Hz, 2H); MS (DCI/$NH_3$) m/z 235 (M+H)$^+$.

Example 1C

4-{2-[(2R)-2-methyl-1-pyrrolidinyl]ethyl}aniline

The product from Example 1B (3.85 g, 16.4 mmol) was hydrogenated using 10% Pd/C (0.39 g) in methanol (20 mL) under 1 atm $H_2$ for 16 hours. After the $H_2$ was replaced with $N_2$, the mixture was diluted with methanol (150 mL), stirred for 15 minutes, filtered, and the filtrate was concentrated to provide the title compound. $^1$H NMR (300 MHz, $CDCl_3$) δ 1.11 (d, J=6 Hz, 3H), 1.43 (m, 1H), 1.74 (m, 2H), 1.90 (m, 1H), 2.25 (m, 3H), 2.70 (m, 2H), 2.97 (m, 1H), 3.24 (td, J=9, 3 Hz, 1H), 3.55 (s, 2H), 6.63 (d, J=8 Hz, 2H), 7.01 (d, J=8 Hz, 2H); MS (DCI/$NH_3$) m/z 205 (M+H)$^+$.

Example 1D 2,2-dimethyl-N-(4-{2-[(2R)-2-methyl-1-pyrrolidinyl]ethyl}phenyl)propanamide The product from Example 1C (2.77 g, 14 mmol) was dissolved in anhydrous dichloromethane (70 mL) under nitrogen, treated with triethylamine (2.3 mL, 16 mmol), cooled to 0° C., treated with trimethylacetyl chloride (1.9 mL, 15 mmol), stirred at ambient temperature for 60 hours and treated with 1 M NaOH (40 mL). The layers were separated and the aqueous layer was extracted with dichloromethane (2 times, 40 mL). The combined dichloromethane layers were dried ($MgSO_4$), filtered, and the filtrate was concentrated to provide 4.0 g of the title compound. $^1$H NMR (300 MHz, $CDCl_3$) δ 1.10 (d, J=6 Hz, 3H), 1.31 (s, 9H), 1.44 (m, 1H), 1.76 (m, 2H), 1.92 (m, 1H), 2.18 (q, J=9 Hz, 1H), 2.27 (m, 2H), 2.78 (m, 2H), 2.99 (m, 1H), 3.23 (td, J=9, 3 Hz, 1H), 7.17 (d, J=8 Hz, 2H), 7.44 (d, J=8 Hz, 2H); MS (DCI/$NH_3$) m/z 289 (M+H)$^+$.

Example 1E

N-(2-formyl-4-{2-[(2R)-2-methyl-1-pyrrolidinyl]ethyl}phenyl)-2,2-dimethylpropanamide The product from Example 1D (4.0 g, 13.9 mmol) under nitrogen in anhydrous diethyl ether (140 mL) was treated with N,N,N'N'-tetramethylethylenediamine (6.5 mL, 43 mmol), cooled to −5° C., treated with n-butyllithium (16.7 mL of a 2.5 M solution in hexanes) over 10 minutes, stirred for 4 hours at ambient temperature, cooled to −5° C., treated all at once with anhydrous N,N-dimethylformamide (6.5 mL, 83 mmol), stirred for 16 hours at ambient temperature, diluted with diethyl ether (100 mL), washed with water (75 mL), washed with brine, dried ($MgSO_4$), filtered, and the filtrate was concentrated. The residue was purified by chromatography on silica gel eluting with a gradient of 2%, 3.5%, 5%, and 7.5% (9:1 MeOH:conc $NH_4OH$) in dichloromethane to provide the title compound. $^1$H NMR (300 MHz, $CDCl_3$) δ 1.10 (d, J=6 Hz, 3H), 1.35 (s, 9H), 1.44 (m, 1H), 1.75 (m, 2H), 1.93 (m, 1H), 2.19 (q, J=9 Hz, 1H), 2.31 (m, 2H), 2.85 (m, 2H), 3.01 (m, 1H), 3.23 (td, J=8, 3 Hz, 1H), 7.47 (dd, J=8, 2 Hz, 1H), 7.51 (d, J=2 Hz, 1H), 8.71 (d, J=8 Hz, 1H), 9.92 (s, 1H), 11.31 (s, 1H); MS (DCI/$NH_3$) m/z 317 (M+H)$^+$.

Example 1F 2-amino-5-{2-[(2R)-2-methyl-1-pyrrolidinyl]ethyl}benzaldehyde

The product from Example 1E (2.46 g, 7.8 mmol) in 3M HCl (40 mL) was heated at 80° C. for 4 hours, allowed to cool to room temperature, and carefully poured into a mixture of 1M NaOH (250 mL) and dichloromethane (75 mL). The layers were separated and the aqueous layer was extracted with dichloromethane (2 times, 75 mL). The combined dichloromethane layers were dried ($MgSO_4$), filtered, and the filtrate was concentrated. The residue was purified by chromatography on silica gel eluting with a gradient of 2%, 3.5% and 5% (9:1 MeOH:conc $NH_4OH$) in dichloromethane to provide the title compound. $^1$H NMR (300 MHz, $CDCl_3$) δ 1.12 (d, J=6 Hz, 3H), 1.50 (m, 1H), 1.76 (m, 2H), 1.93 (m, 1H), 2.25 (m, 3H), 2.76 (m, 2H), 2.99 (m, 1H), 3.25 (td, J=9, 3 Hz, 1H), 5.99 (s, 2H), 6.60 (d, J=8 Hz, 1H), 7.19 (dd, J=8, 2 Hz, 1H), 7.31 (d, J=2 Hz, 1H), 9.85 (s, 1H); MS (DCI/$NH_3$) m/z 233 (M+H)$^+$.

Example 1G

6-[2-((2R)-2-Methyl-pyrrolidin-1-yl)-ethyl]-2-(4-methyl-2-thiophen-2-yl-thiazol-5-yl)-quinoline The product from Example 1F (23 mg, 0.1 mmol) and 1-(4-methyl-2-thiophen-2-yl-thiazol-5-yl)-ethanone (Singh, S. P. et. al., Indian J. Chem. Sect. B, 1990, 29(6), 533–538) (10 mg, 0.045 mmol) were combined in ethanol 0.2 mL and treated with one drop of a saturated solution of potassium hydroxide in ethanol and heated at 80° C. for 16 hours. The mixture was allowed to cool to room temperature and concentrated. The residue was purified by chromatography on silica gel eluting with a gradient of 2% and 3.5% of (9:1 MeOH:conc $NH_4OH$) in dichloromethane to provide the title compound. $^1$H NMR (300 MHz, $CDCl_3$) δ 1.15 (d, J=6.10 Hz, 3H), 1.49 (m, 1H), 1.79 (m, 2H), 1.96 (m, 1H), 2.27 (m, 1H), 2.43 (m, 2H), 2.82 (s, 3H), 3.05 (m, 2H), 3.15 (m, 1H), 3.32 (m, 1H), 7.10 (dd, J=5.09, 3.73 Hz, 1H), 7.41 (dd, J=5.09, 1.02 Hz, 1H), 7.57 (dd, J=3.56, 1.19 Hz, 1H), 7.62 (m, 2H), 7.72 (d, J=8.48 Hz, 1H), 8.01 (d, J=8.14 Hz, 1H), 8.13 (d, J=8.48 Hz, 1H); MS (DCI-$NH_3$) [M+H]$^+$ at 420.

Example 2

6-[2-((2R)-2-Methyl-pyrrolidin-1-yl)-ethyl]-2-[2-(4-methyl-[1, 2, 3]thiadiazol-5-yl)-thiazol-4-yl]-quinoline The title compound was prepared using the procedure described in Example 1G substituting 1-[2-(4-methyl-[1,2,3]thiadiazol-5-yl)-thiazol-4-yl]-ethanone (Maybridge Chemical Company Ltd., catalog number SPB 03839) for 1-(4-methyl-2-thiophen-2-yl-thiazol-5-yl)-ethanone. $^1$H NMR (300 MHz, CDCl$_3$) δ 1.14 (d, J=6.10 Hz, 3H), 1.47 (m, 1H), 1.77 (m, 2H), 1.95 (m, 1H), 2.26 (q, J=8.70 Hz, 1H), 2.41 (m, 2H), 3.04 (m, 2H), 3.07 (s, 3H), 3.15 (m, 1H), 3.31 (m, 1H), 7.63 (dd, J=8.82, 2.03 Hz, 1H), 7.67 (s, 1H), 8.05 (d, J=8.82 Hz, 1H), 8.22 (d, J=8.48 Hz, 1H), 8.33 (d, J=8.48 Hz, 1H), 8.53 (s, 1H); MS (DCI-NH$_3$) [M+H]$^+$ at 422.

Example 3

2-(4-Methyl-2-pyrazin-2-yl-thiazol-5-yl)-6-[2-((2R)-2-methyl-pyrrolidin-1-yl)-ethyl]-quinoline The title compound was prepared using the procedure described in Example 1G substituting 1-(4-methyl-2-pyrazin-2-yl-thiazol-5-yl)-ethanone (Maybridge Chemical Company Ltd., catalog number SEW 06370) for 1-(4-methyl-2-thiophen-2-yl-thiazol-5-yl)-ethanone. $^1$H NMR (300 MHz, CDCl$_3$) δ 1.15 (d, J=6.10 Hz, 3H), 1.49 (m, 1H), 1.79 (m, 2H), 1.96 (m, 1H), 2.27 (m, 1H), 2.43 (m, 2H), 2.90 (s, 3H), 3.05 (m, 2H), 3.15 (m, 1H), 3.32 (m, 1H), 7.63 (m, 2H), 7.74 (d, J=8.81 Hz, 1H), 8.03 (d, J=8.14 Hz, 1H), 8.16 (d, J=8.14 Hz, 1H), 8.59 (dd, J=2.71, 1.70 Hz, 1H), 8.60 (d, J=2.71 Hz, 1H), 9.46 (d, J=1.36 Hz, 1H); MS (DCI-NH$_3$) [M+H]$^+$ at 416.

Example 4

2-[1-(3,4-Dichloro-phenyl)-5-methyl-1H-pyrazol-4-yl]-6-[2-((2R)-2-methyl-pyrrolidin-1-yl)-ethyl]-quinoline The title compound was prepared using the procedure described in Example 1G substituting 1-[1-(3,4-dichloro-phenyl)-5-methyl-1H-pyrazol-4-yl]-ethanone (Maybridge Chemical Company Ltd., catalog number CD 10634) for 1-(4-methyl-2-thiophen-2-yl-thiazol-5-yl)-ethanone. $^1$H NMR (300 MHz, CDCl$_3$) δ 1.14 (d, J=5.76 Hz, 3H), 1.48 (m, 1H), 1.78 (m, 2H), 1.95 (m, 1H), 2.25 (q, J=8.82 Hz, 1H), 2.39 (m, 2H), 2.80 (s, 3H), 3.02 (m, 2H), 3.13 (m, 1H), 3.30 (m, 1H), 7.40 (dd, J=8.48, 2.37 Hz, 1H), 7.61 (m, 4H), 7.68 (d, J=2.37 Hz, 1H), 8.00 (d, J=8.48 Hz, 1H), 8.11 (m, 2H); MS (DCI-NH$_3$) [M+H]$^+$ at 465.

Example 5

2-[2-(4-Chloro-phenoxymethyl)-thiazol-4-yl]-6-[2-((2R)-2-methyl-pyrrolidin-1-yl)-ethyl]-quinoline The title compound was prepared using the procedure described in Example 1G substituting 1-[2-(4-chloro-phenoxymethyl)-thiazol-4-yl]-ethanone (Maybridge Chemical Company Ltd., catalog number SPB 03561) for 1-(4-methyl-2-thiophen-2-yl-thiazol-5-yl)-ethanone. $^1$H NMR (300 MHz, CDCl$_3$) δ 1.14 (d, J=5.76 Hz, 3H), 1.49 (m, 1H), 1.79 (m, 2H), 1.96 (m, 1H), 2.27 (m, 1H), 2.43 (m, 2H), 3.05 (m, 2 H), 3.15 (m, 1H), 3.32 (m, 1H), 5.45 (s, 2H), 6.99 (d, J=9.15 Hz, 2H), 7.28 (m, 2H), 7.61 (dd, J=8.48, 2.03 Hz, 1H), 7.64 (m, 1H), 8.06 (d, J=8.81 Hz, 1H), 8.19 (d, J=1.02 Hz, 2H), 8.27 (s, 1H); MS (DCI-NH$_3$) [M+H]$^+$ at 464

Example 6

2-(5-Methyl-1-Pyridin-2-yl-1H-pyrazol-4-yl)-6-[2-((2R)-2-methyl-pyrrolidin-1-yl)-ethyl]-quinoline The title compound was prepared using the procedure described in Example 1G using 1-(5-methyl-1-pyridin-2-yl-1H-pyrazol-4-yl)-ethanone (Singh, S. P., et. al. Heterocycl. Commun., 2001, 7(1), p. 49-54) for 1-(4-methyl-2-thiophen-2-yl-thiazol-5-yl)-ethanone. $^1$H NMR (300 MHz, CDCl$_3$) δ 1.14 (d, J=6.10 Hz, 3H), 1.46 (m, 1H), 1.77 (m, 2H), 1.96 (m, 1H), 2.25 (q, J=8.82 Hz, 1H), 2.40 (m, 2H), 3.01 (m, 2H), 3.06 (s, 3H), 3.13 (m, 1H), 3.30 (td, J=8.56, 2.54 Hz, 1H), 7.26 (m, 1H), 7.61 (m, 3H), 7.87 (m, 2H), 8.03 (d, J=8.48 Hz, 1H), 8.11 (d, J=8.82 Hz, 1H), 8.13 (s, 1H), 8.53 (m, 1H); MS (DCI-NH$_3$) [M+H]$^+$ at 398.

Example 7

2-[5-Methyl-1-(6-methyl-4-trifluoromethyl-pyridin-2-yl)-1H-pyrazol-4-yl]-6-[2-((2R)-2-methyl-pyrrolidin-1-yl)-ethyl]-quinoline The title compound was prepared using the procedure described in Example 1G using 1-[5-methyl-1-(6-methyl-4-trifluoromethyl-pyridin-2-yl)-1H-pyrazol-4-yl]-ethanone (Maybridge Chemical Company Ltd., catalog number CD 11385) for 1-(4-methyl-2-thiophen-2-yl-thiazol-5-yl)-ethanone. $^1$H NMR (300 MHz, CDCl$_3$) δ 1.15 (d, J=6.10 Hz, 3H), 1.49 (m, 1H), 1.79 (m, 2H), 1.96 (m, 1H), 2.27 (m, 1H), 2.43 (m, 2H), 2.68 (s, 3H), 3.05 (m, 2H), 3.11 (s, 3H), 3.15 (m, 1H), 3.32 (m, 1H), 7.30 (s, 1H), 7.61 (m, 3H), 8.01 (s, 1H), 8.03 (d, J=8.48 Hz, 1H), 8.12 (d, J=8.14 Hz, 1H), 8.14 (s, 1H); MS (DCI-NH$_3$) [M+H]$^+$ at 480.

Example 8

2-[3-(4-Chloro-phenyl)-isoxazol-5-yl]-6-[2-((2R)-2-methyl-pyrrolidin-1-yl)-ethyl]-quinoline The title compound was prepared using the procedure described in Example 1G substituting 1-[3-(4-chloro-phenyl)-isoxazol-5-yl]-ethanone (Key Organics Limited/Bionet Research., catalog number 11 L-568S) for 1-(4-methyl-2-thiophen-2-yl-thiazol-5-yl)-ethanone. $^1$H NMR (300 MHz, CDCl$_3$) δ 1.14 (d, J=6.10 Hz, 3H), 1.47 (m, 1H), 1.79 (m, 2H), 1.96 (m, 1H), 2.26 (m, 1H), 2.42 (m, 2H), 3.04 (m, 2H), 3.15 (m, 1H), 3.30 (m, 1H), 7.39 (s, 1H), 7.48 (d, J=8.48 Hz, 2H), 7.68 (m, 2H), 7.88 (d, J=8.48 Hz, 2H), 8.05 (d, J=8.48 Hz, 1H), 8.09 (d, J=8.14 Hz, 1H), 8.26 (d, J=8.48 Hz, 1H); MS (DCI-NH$_3$) [M+H]$^+$ at 418.

Example 9

6-[2-(2R)-2-Methyl-pyrrolidin-1-yl)-ethyl]-2-[5-(1-methyl-5-trifluoromethyl-1H-pyrazol-3-yl)-thiophen-2-yl]-quinoline The title compound was prepared using the procedure described in Example 1G substituting 1-[5-(1-methyl-5-trifluoromethyl-1H-pyrazol-3-yl)-thiophen-2-yl]-ethanone (Maybridge Chemical Company Ltd., catalog number KM 03660) for 1-(4-methyl-2-thiophen-2-yl-thiazol-5-yl)-ethanone. ¹H NMR (300 MHz, CDCl₃) δ 1.13 (d, J=6.10 Hz, 3H), 1.46 (m, 1H), 1.77 (m, 2H), 1.95 (m, 1H), 2.24 (q, J=8.36 Hz, 1H), 2.39 (m, 2H), 3.01 (m, 2H), 3.12 (m, 1H), 3.29 (td, J=8.31, 2.71 Hz, 1H), 4.12 (s, 3H), 6.73 (s, 1H), 7.26 (d, J=4.07 Hz, 1H), 7.61 (m, 2H), 7.69 (d, J=3.73 Hz, 1H), 7.79 (d, J=8.48 Hz, 1H), 8.01 (d, J=9.15 Hz, 1H), 8.12 (d, J=8.48 Hz, 1H); MS (DCI-NH₃) [M+H]⁺ at 471.

Example 10

2-(4-Methyl-2-morpholin-4-yl-thiazol-5-yl)-6-[2-((2R)-2-methyl-pyrrolidin-1-yl)-ethyl]-quinoline The title compound was prepared using the procedure described in Example 1G substituting 1-(4-methyl-2-morpholin-4-yl-thiazol-5-yl)-ethanone (Ohtsuka, H. et al. Chem. Pharm. Bull. 1975, 23, 3234-3242) for 1-(4-methyl-2-thiophen-2-yl-thiazol-5-yl)-ethanone. ¹H NMR (300 MHz, CDCl₃) δ 1.13 (d, J=5.76 Hz, 3H), 1.46 (m, 1H), 1.76 (m, 2H), 1.94 (m, 1H), 2.24 (q, J=8.70 Hz, 1H), 2.38 (m, 2H), 2.63 (s, 3H), 2.99 (m, 2H), 3.11 (m, 1H), 3.29 (m, 1H), 3.56 (m, 4H), 3.83 (m, 4H), 7.55 (m, 2H), 7.62 (d, J=8.82 Hz, 1H), 7.91 (d, J=8.48 Hz, 1H), 8.03 (d, J=8.48 Hz, 1H); MS (DCI-NH₃) [M+H]⁺ at 423.

Example 11

6-[2-((2R)-2-Methyl-pyrrolidin-1-yl)-ethyl]-2-(2-phenyl-thiazol-5-yl)-quinoline

The title compound was prepared using the procedure described in Example 1G substituting 1-(2-phenyl-thiazol-5-yl)-ethanone (Arcadi, A., et al. Eur. J. Org. Chem. 1999, 11, p. 3117-3126) for 1-(4-methyl-2-thiophen-2-yl-thiazol-5-yl)-ethanone. ¹H NMR (300 MHz, CDCl₃) δ 1.13 (d, J=6.10 Hz, 3H), 1.46 (m, 1H), 1.78 (m, 2H), 1.95 (m, 1H), 2.24 (q, J=8.82 Hz, 1H), 2.39 (m, 2H), 3.01 (m, 2H), 3.13 (m, 1H), 3.29 (td, J=8.48, 2.71 Hz, 1H), 7.47 (m, 3H), 7.61 (m, 2H), 7.81 (d, J=8.48 Hz, 1H), 8.03 (m, 3H), 8.12 (d, J=8.48 Hz, 1H), 8.38 (s, 1H); MS (DCI-NH₃) [M+H]⁺ at 400.

Example 12

2-(4-Methyl-2-pyridin-2-yl-thiazol-5-yl)-6-[2-((2R)-2-methyl-pyrrolidin-1-yl)-ethyl]-quinoline The title compound was prepared using the procedure described in Example 1G substituting 1-(4-methyl-2-pyridin-2-yl-thiazol-5-yl)-ethanone (Key Organics Limited/Bionet Research., catalog number 8P-710) for 1-(4-methyl-2-thiophen-2-yl-thiazol-5-yl)-ethanone. ¹H NMR (300 MHz, CDCl₃) δ 1.14 (d, J=6.10 Hz, 3H), 1.46 (m, 1H), 1.78 (m, 2H), 1.95 (m, 1H), 2.25 (q, J=8.93 Hz, 1H), 2.40 (m, 2H), 2.89 (s, 3H), 3.03 (m, 2H), 3.13 (m, 1H), 3.30 (m, 1H), 7.33 (ddd, J=7.54, 4.83, 1.19 Hz, 1H), 7.62 (m, 2H), 7.72 (d, J=8.81 Hz, 1H), 7.80 (td, J=7.80, 1.70 Hz, 1H), 8.02 (dd, J=9.15, 0.68 Hz, 1H), 8.14 (d, J=8.81 Hz, 1H), 8.22 (dt, J=7.88, 1.14 Hz, 1H), 8.64 (ddd, J=4.83, 1.78, 0.85 Hz, 1H); MS (DCI-NH₃) [M+H]⁺ at 415.

Example 13

2-[3-(3-Chloro-5-trifluoromethyl-pyridin-2-yl)-isoxazol-5-yl]-6-[2-((2R)-2-methyl-pyrrolidin-1-yl)-ethyl]-quinoline The title compound was prepared using the procedure described in Example 1G using 1-[3-(3-chloro-5-trifluoromethyl-pyridin-2-yl)-isoxazol-5-yl]-ethanone (Key Organics Limited/Bionet Research, catalog number 10G-001) for 1-(4-methyl-2-thiophen-2-yl-thiazol-5-yl)-ethanone. ¹H NMR (300 MHz, CDCl₃) δ 1.13 (d, J=6.10 Hz, 3H), 1.46 (m, 1H), 1.79 (m, 2H), 1.95 (m, 1H), 2.25 (q, J=8.59 Hz, 1H), 2.40 (m, 2H), 3.04 (m, 2H), 3.15 (m, 1H), 3.29 (td, J=8.56, 2.88 Hz, 1H), 7.69 (m, 3H), 8.10 (m, 3H), 8.27 (d, J=8.48 Hz, 1H), 8.93 (d, J=2.03 Hz, 1H); MS (DCI-NH₃) [M+H]⁺ at 487.

Example 14

2-(4-Methyl-2-pyridin-3-yl-thiazol-5-yl)-6-[2-((2R)-2-methyl-pyrrolidin-1-yl)-ethyl]-quinoline The title compound was prepared using the procedure described in Example 1G substituting 1-(4-methyl-2-pyridin-3-yl-thiazol-5-yl)-ethanone (Key Organics Limited/Bionet Research, catalog number 5H-926) for 1-(4-methyl-2-thiophen-2-yl-thiazol-5-yl)-ethanone. ¹H NMR (300 MHz, CDCl₃) δ 1.15 (d, J=6.10 Hz, 3H), 1.48 (m, 1H), 1.77 (m, 2H), 1.95 (m, 1H), 2.26 (q, J=8.82 Hz, 1H), 2.42 (m, 2H), 2.87 (s, 3H), 3.03 (m, 2H), 3.14 (m, 1H), 3.30 (m, 1H), 7.40 (dd, J=7.80, 4.75 Hz, 1H), 7.64 (m, 2H), 7.74 (d, J=8.48 Hz, 1H), 8.03 (d, J=8.48 Hz, 1H), 8.17 (d, J=8.48 Hz, 1H), 8.30 (dt, J=7.88, 1.99 Hz, 1H), 8.67 (dd, J=4.75, 1.70 Hz, 1H), 9.23 (d, J=2.03 Hz, 1H); MS (DCI-NH₃) [M+H]⁺ at 415.

Example 15

2-(4-Methyl-2-pyridin-4-yl-thiazol-5-yl)-6-[2-((2R)-2-methyl-pyrrolidin-1-yl)-ethyl]-quinoline The title compound was prepared using the procedure described in Example 1G substituting 1-(4-methyl-2-pyridin-4-yl-thiazol-5-yl)-ethanone (Key Organics Limited/Bionet Research, catalog number 2P-726) for 1-(4-methyl-2-thiophen-2-yl-thiazol-5-yl)-ethanone. ¹H NMR (300 MHz, CDCl₃) δ 1.14 (d, J=6.10 Hz, 3H), 1.47 (m, 1H), 1.79 (m, 2H), 1.95 (m, 1H), 2.25 (q, J=8.82 Hz, 1H), 2.41 (m, 2H), 2.87 (s, 3H), 3.03 (m, 2H), 3.13 (m, 1H), 3.30 (td, J=8.56, 2.88 Hz, 1H), 7.64 (m, 2H), 7.74 (d, J=8.48 Hz, 1H), 7.86 (dd, J=4.41, 1.70 Hz, 2H), 8.03 (d, J=9.16 Hz, 1H), 8.17 (d, J=8.48 Hz, 1H), 8.72 (dd, J=4.41, 1.70 Hz, 2H); MS (DCI-NH₃) [M+H]⁺ at 415.

Example 16

6-[2-((2R)-2-Methyl-pyrrolidin-1-yl)-ethyl]-2-(2-phenyl-thiazol-4-yl)-quinoline

The title compound was prepared using the procedure described in Example 1G substituting 1-(2-phenyl-thiazol-4-yl)-ethanone (CAS # 10045-52-0, Maybridge Chemical Company Ltd., catalog number SPB 03431) for 1-(4-methyl-2-thiophen-2-yl-thiazol-5-yl)-ethanone. ¹H NMR (300 MHz, CDCl₃) δ 1.14 (d, J=6.10 Hz, 3H), 1.48 (m, 1H), 1.78 (m, 2H), 1.95 (m, 1H), 2.25 (q, J=8.82 Hz, 1H), 2.41 (m, 2H), 3.02 (m, 2H), 3.14 (m, 1H), 3.30 (m, 1H), 7.48 (m, 3H), 7.63 (m, 2H), 8.07 (m, 3 H), 8.20 (d, J=8.48 Hz, 1H), 8.30 (s, 1H), 8.42 (d, J=8.48 Hz, 1H); MS (DCI-NH$_3$) [M+H]$^+$ at 400.

Example 17

2-[3-(4-Chloro-phenyl)-5-methyl-isoxazol-4-yl]-6-[2-((2R)-2-methyl-pyrrolidin-1-yl)-ethyl]-quinoline The title compound was prepared using the procedure described in Example 1G-substituting 1-[3-(4-chloro-phenyl)-5-methyl-isoxazol-4-yl]-ethanone (CAS # 169814-48-6, Maybridge Chemical Company Ltd., catalog number SPB 04957) for 1-(4-methyl-2-thiophen-2-yl-thiazol-5-yl)-ethanone. $^1$H NMR (300 MHz, CDCl$_3$) δ 1.14 (d, J=5.76 Hz, 3H), 1.47 (m, 1H), 1.78 (m, 2H), 1.96 (m, 1H), 2.25 (q, J=8.70 Hz, 1H), 2.40 (m, 2H), 2.68 (s, 3H), 3.03 (m, 2H), 3.15 (m, 1H), 3.30 (td, J=8.39, 2.54 Hz, 1H), 7.08 (d, J=8.48 Hz, 1H), 7.32 (ddd, J=8.65, 2.20, 2.03 Hz, 2H), 7.45 (ddd, J=8.65, 2.37, 2.20 Hz, 2H), 7.65 (m, 2H), 8.01 (d, J=8.48 Hz, 1H), 8.03 (d, J=8.82 Hz, 1H); MS (DCI-NH$_3$) [M+H]$^+$ at 432.

Example 18

1-(4-[6-{2-((2R)-2-Methyl-pyrrolidin-1-yl)-ethyl]-quinolin-2-yl}-phenyl)-1H-pyridin-4-one The title compound was prepared using the procedure described in Example 1G using 1-(4-acetyl-phenyl)-1H-pyridin-4-one for 1-(4-methyl-2-thiophen-2-yl-thiazol-5-yl)-ethanone. $^1$H NMR (300 MHz, CDCl$_3$) δ 1.15 (d, J=6.10 Hz, 3H), 1.49 (m, 1H), 1.78 (m, 2H), 1.95 (m, 1H), 2.27 (m, 1H), 2.43 (m, 2H), 3.05 (m, 2H), 3.16 (m, 1H), 3.31 (m, 1H), 6.54 (d, J=7.80 Hz, 2H), 7.49 (d, J=8.48 Hz, 2H), 7.66 (m, 4H), 7.87 (d, J=8.81 Hz, 1H), 8.10 (d, J=8.48 Hz, 1H), 8.22 (d, J=8.48 Hz, 1H), 8.33 (d, J=8.48 Hz, 2H); MS (DCI-NH$_3$) [M+H]$^+$ at 410.

Example 19

6-[2-((2R)-2-Methyl-pyrrolidin-1-yl)-ethyl]-2-(4-piperidin-1-yl-phenyl)-quinoline The title compound was prepared using the procedure described in Example 1G using 1-(4-piperidin-1-yl-phenyl)-ethanone for 1-(4-methyl-2-thiophen-2-yl-thiazol-5-yl)-ethanone. $^1$H NMR (300 MHz, CDCl$_3$) δ 1.14 (d, J=5.42 Hz, 3H), 1.70 (m, 10H), 2.24 (m, 1H), 2.39 (m, 2H), 3.01 (m, 2H), 3.14 (m, 1H), 3.29 (m, 5H), 7.04 (d, J=8.81 Hz, 2H), 7.56 (dd, J=8.48, 2.03 Hz, 1H), 7.59 (s, 1H), 7.80 (d, J=8.48 Hz, 1H), 8.01–8.10 (m, 4H); MS (DCI-NH$_3$) [M+H]$^+$ at 400.

Example 20

2-(5'-Methyl-[2,2']bithiophenyl-5-yl)-6-[2-((2R)-2-methyl-pyrrolidin-1-yl)-ethyl]-quinoline The title compound was prepared using the procedure described in Example 1G substituting 1-(5'-methyl-[2,2'] bithiophenyl-5-yl)-ethanone (Churkin, Yu. D.; et. al. Pharm. Chem. J. (Engl. Transl.) 1982, 16, pages 103–105) for 1-(4-methyl-2-thiophen-2-yl-thiazol-5-yl)-ethanone. $^1$H NMR (300 MHz, CDCl$_3$) δ 1.15 (d, J=6.10 Hz, 3H), 1.48 (m, 1H), 1.78 (m, 2H), 1.94 (m, 1H), 2.25 (m, 1H), 2.40 (m, 2H), 2.51 (s, 3H), 3.01 (m, 2H), 3.13 (m, 1H), 3.30 (m, 1H), 6.70 (dd, J=3.56, 1.19 Hz, 1H), 7.11 (dd, J=8.14, 3.73 Hz, 2H), 7.57 (m, 3H), 7.74 (d, J=8.81 Hz, 1H), 7.99 (d, J=9.49 Hz, 1H), 8.05 (d, J=8.48 Hz, 1H); MS (DCI-NH$_3$) [M+H]$^+$ at 419.

Example 21

2-(6-Methyl-2-phenyl-pyrimidin-4-yl)-6-[2-((2R)-2-methyl-pyrrolidin-1-yl)-ethyl]-quinoline The title compound was prepared using the procedure described in Example 1G substituting 1-(6-methyl-2-phenyl-pyrimidin-4-yl)-ethanone (Sakamoto, T. et al. Heterocycles 1977, 6, pages 1616–1621) for 1-(4-methyl-2-thiophen-2-yl-thiazol-5-yl)-ethanone. $^1$H NMR (300 MHz, CDCl$_3$) δ 1.15 (d, J=6.10 Hz, 3H), 1.48 (m, 1H), 1.78 (m, 2H), 1.96 (m, 1H), 2.27 (q, J=8.70 Hz, 1H), 2.43 (m, 2H), 2.73 (s, 3H), 3.06 (m, 2H), 3.16 (m, 1H), 3.31 (m, 1H), 7.53 (m, 3H), 7.66 (dd, J=8.65, 1.87 Hz, 1H), 7.71 (s, 1H), 8.13 (d, J=8.82 Hz, 1H), 8.29 (d, J=8.48 Hz, 1H), 8.36 (s, 1H), 8.63 (m, 2H), 8.78 (d, J=8.48 Hz, 1H); MS (DCI-NH$_3$) [M+H]$^+$ at 409.

Example 22

2-(5-Chloro-1-methyl-3-phenyl-1H-pyrazol-4-yl)-6-[2-((2R)-2-methyl-pyrrolidin-1-yl)-ethyl]-quinoline The title compound was prepared using the procedure described in Example 1G using 1-(5-chloro-1-methyl-3-phenyl-1H-pyrazol-4-yl)-ethanone for 1-(4-methyl-2-thiophen-2-yl-thiazol-5-yl)-ethanone. $^1$H NMR (300 MHz, CDCl$_3$) δ 1.15 (d, J=6.10 Hz, 3H), 1.48 (m, 1H), 1.78 (m, 2H), 1.96 (m, 1H), 2.27 (q, J=8.59 Hz, 1H), 2.41 (m, 2H), 3.03 (m, 2H), 3.15 (m, 1H), 3.31 (m, 1H), 3.99 (s, 3H), 7.26 (m, 4H), 7.46 (m, 2H), 7.62 (m, 2H), 8.00 (d, J=8.48 Hz, 1H), 8.05 (d, J=8.14 Hz, 1H); MS (DCI-NH$_3$) [M+H]$^+$ at 431.

Example 23

6-[2-((2R)-2-Methyl-pyrrolidin-1-yl)-ethyl]-2-(1-pyridin-3-yl-cyclobutyl)-quinoline The title compound was prepared using the procedure described in Example 1G using 1-(1-pyridin-3-yl-cyclobutyl)-ethanone for 1-(4-methyl-2-thiophen-2-yl-thiazol-5-yl)-ethanone. $^1$H NMR (300 MHz, CDCl$_3$) δ 1.12 (d, J=6.10 Hz, 3H), 1.46 (m, 1H), 1.75 (m, 2H), 1.92 (m, 1H), 2.05 (m, 2H), 2.23 (q, J=8.82 Hz, 1H), 2.37 (m, 2H), 2.77 (m, 2H), 2.94-3.22 (m, 5H), 3.28 (m, 1H), 7.17 (m, 1H), 7.19 (m, 1H), 7.56 (s, 1H), 7.58 (dd, J=8.48, 2.03 Hz, 1H), 7.65 (ddd, J=8.05, 2.46, 1.70 Hz, 1H), 7.95 (d, J=8.81 Hz, 1H), 8.04 (d, J=8.48 Hz, 1H), 8.41 (dd, J=4.75, 1.70 Hz, 1H), 8.70 (dd, J=2.37, 0.68 Hz, 1H); MS (DCI-NH$_3$) [M+H]$^+$ at 372.

Example 24

2-Methyl-3-[1-(5-methyl-isoxazol-3-yl)-1H-[1,2,4]triazol-3-yl]-6-[2-((2R)-2-methyl-pyrrolidin-1-yl)-ethyl]-quinoline The title compound was prepared using the procedure described in Example 1G substituting 1-[1-(5-methyl-isoxazol-3-yl)-1H-[1,2,4]triazol-3-yl]-propan-2-one (Kano, H. et. al. Tetrahedron 1964, 20, pages 159–164) for 1-(4-methyl-2-thiophen-2-yl-thiazol-5-yl)-ethanone. $^1$H NMR (300 MHz, CDCl$_3$) δ 1.14 (d, J=6.10 Hz, 3H), 1.49 (m, 1H), 1.79 (m, 2H), 1.96 (m, 1H), 2.27 (m, 1H), 2.43 (m, 2H), 2.55 (s, 3H), 3.05 (m, 2H), 3.09 (s, 3H), 3.15 (m, 1H), 3.32 (m, 1H), 6.56 (q, J=1.02 Hz, 1H), 7.63 (dd, J=8.81, 2.03 Hz, 1H), 7.70 (d, J=1.70 Hz, 1H), 7.99 (d, J=8.48 Hz, 1H), 8.81 (s, 1H), 8.91 (s, 1H); MS (DCI-NH$_3$) [M+H]$^+$ at 403.

Example 25

2-[1-(2,4-difluoro-phenyl)-5-methyl-1H-[1,2,3]triazol-4-yl]-6-[2-{(2R)-2-methyl-pyrrolidin-1-yl]-ethyl}-quinoline The title compound was prepared using the procedure described in Example 1G substituting 1-[1-(2,4-difluoro-phenyl)-5-methyl-1 H-[1,2,3]triazol-4-yl]-ethanone (Maybridge Chemical Company Ltd., catalog number CD 09885) for 1-(4-methyl-2-thiophen-2-yl-thiazol-5-yl)-ethanone. $^1$H NMR (300 MHz, CD$_3$OD) δ 1.20 (d, J=6 Hz, 3H), 1.50 (m, 1H), 1.83 (m, 2H), 2.06 (m, 1H), 2.43 (m, 1H), 2.54 (m, 2H), 2.68 (s, 3H), 3.07 (m, 2H), 3.22 (m, 2H), 6.96 (m, 1H), 7.22 (m, 1H), 7.47 (m, 1H), 7.68 (d, J=9 Hz, 1H), 7.79 (s, 1H), 8.01 (d, J=9 Hz, 1H), 8.25 (m, 1H), 8.35 (m, 1H); MS (DCI/NH$_3$) m/z 434 (M+H)$^+$.

Example 26

2-[1-(6-ethoxy-pyridazin-3-yl)-5-methyl-1H-pyrazol-4-yl]-6-{2-[(2R)-2-methyl-Pyrrolidin-1-yl]-ethyl}-quinoline The title compound was prepared using the procedure described in Example 1G substituting 1-[1-(6-chloro-pyridazin-3-yl)-5-methyl-1 H-pyrazol-4-yl]-ethanone (Maybridge Chemical Company Ltd., catalog number CD 10406) for 1-(4-methyl-2-thiophen-2-yl-thiazol-5-yl)-ethanone and substituting three equivalents of potassium ethoxide for potassium hydroxide. $^1$H NMR (300 MHz, CD$_3$OD) δ 1.20 (d, J=6 Hz, 3H), 1.49 (t, J=6 Hz, 3H), 1.50 (m, 1H), 1.84 (m, 1H), 2.06 (m, 2H), 2.41 (m, 1H), 2.55 (m, 2H), 2.97 (s, 3H), 3.06 (m, 2H), 3.24 (m, 2H), 4.59 (q, J=6 Hz, 2H), 7.37 (d, J=9 Hz, 1H), 7.68 (dd, J=9 Hz, J=3 Hz, 1H), 7.78 (d, J=9 Hz, 2H), 7.99 (d, J=9 Hz, 1H), 8.05 (d, J=9 Hz, 1H), 8.25 (s, 1H), 8.30 (d, J=9 Hz, 1H); MS (DCI/NH$_3$m/z 443 (M+H)$^+$.

Example 27

2-(2'-methyl-[2,4']bithiazolyl-4-yl)-6-{2-[(2R)-2-methyl-pyrrolidin-1-yl]-ethyl}-quinoline The title compound was prepared using the procedure described in Example 1G substituting 1-(2'-methyl-[2,4']bithiazolyl-4-yl)-ethanone (Maybridge Chemical Company Ltd., catalog number SPB 03623) for 1-(4-methyl-2-thiophen-2-yl-thiazol-5-yl)-ethanone. $^1$H NMR (300 MHz, CD$_3$OD) δ 1.19 (d, J=6 Hz, 3H), 1.50 (m, 1H), 1.83 (m, 2H), 2.03 (m, 1H), 2.41 (q, J=6 Hz, 1H), 2.53 (m, 2H), 2.78 (s, 3H), 3.07 (m, 2H), 3.22 (m, 2H), 7.70 (dd, J=9 Hz, J=3 Hz, 1H), 7.79 (d, J=3 Hz, 1H), 8.06 (d, J=9 Hz, 1H), 8.16 (s, 1H), 8.34 (d, J=3 Hz, 1H), 8.37 (m, 1H); MS (DCI/NH$_3$) m/z 421 (M+H)$^+$.

Example 28

2-[2-(5-methyl-isoxazol-3-yl)-thiazol-4-yl]-6-{2-[(2R)-2-methyl-pyrrolidin-1-yl]-ethyl}-quinoline The title compound was prepared using the procedure described in Example 1G substituting 1-[2-(5-methyl-isoxazol-3-yl)-thiazol-4-yl]-ethanone (Maybridge Chemical Company Ltd., catalog number SPB 04706) for 1-(4-methyl-2-thiophen-2-yl-thiazol-5-yl)-ethanone. $^1$H NMR (300 MHz, CD$_3$OD) δ 1.19 (d, J=6 Hz, 3H), 1.50 (m, 1H), 1.83 (m, 2H), 2.03 (m, 1H), 2.41 (q, J=6 Hz, 1H), 2.53 (m, 2H), 2.55 (s, 3H), 3.07 (m, 2H), 3.22 (m, 2H), 6.84 (s, 1H), 7.70 (dd, J=9 Hz, J=3 Hz, 1H), 7.80 (d, J=3 Hz, 1H), 8.06 (d, J=9 Hz, 1H), 8.35 (s, 1H), 8.36 (d, J=6 Hz, 1H), 8.52 (s, 1H); MS (DCI/NH$_3$) m/z 405 (M+H)$^+$.

Example 29

2-[2-(2,6-dichloro-pyridin-4-yl)-thiazol-4-yl]-6-{2-[(2R)-2-methyl-Pyrrolidin-1-yl]-ethyl}-quinoline The title compound was prepared using the procedure described in Example 1G substituting 1-[2-(2,6-dichloro-pyridin-4-yl)-thiazol-4-yl]-ethanone (Maybridge Chemical Company Ltd., catalog number SPB 07948) for 1-(4-methyl-2-thiophen-2-yl-thiazol-5-yl)-ethanone. $^1$H NMR (300 MHz, CD$_3$OD) δ 1.21 (d, J=6 Hz, 3H), 1.54 (m, 1H), 1.86 (m, 2H), 2.04 (m, 1H), 2.46 (q, J=6 Hz, 1H), 2.59 (m, 2H), 3.07 (m, 2H), 3.27 (m, 2H), 6.67 (s, 1H), 7.71 (dd, J=9 Hz, J=3 Hz, 1H), 7.82 (d, J=3 Hz, 1H), 8.07 (d, J=9 Hz, 1H), 8.12 (s, 1H), 8.40 (d, J=6 Hz, 2H), 8.57 (s, 1H); MS (DCI/NH$_3$) m/z 470 (M+H)$^+$.

Example 30

6-{2-[(2R)-2-methyl-pyrrolidin-1-yl]-ethyl}-2-{2-[6-(2,2,2-trifluoro-ethoxy)-pyridin-3-yl]-thiazol-4-yl}-quinoline The title compound was prepared using the procedure described in Example 1G substituting 1-{2-[6-(2,2,2-trifluoro-ethoxy)-pyridin-3-yl]-thiazol-4-yl}-ethanone (Maybridge Chemical Company Ltd., catalog number SPB 07471) for 1-(4-methyl-2-thiophen-2-yl-thiazol-5-yl)-ethanone. $^1$H NMR (300 MHz, CD$_3$OD) δ 1.20 (d, J=6 Hz, 3H), 1.49 (m, 1H), 1.85 (m, 2H), 2.04 (m, 1H), 2.41 (q, J=6 Hz, 1H), 2.55 (m, 2H), 3.08 (m, 2H), 3.27 (m, 2H), 4.98 (q, J=6 Hz, 2H), 7.07 (d, J=9 Hz, 1H), 7.70 (dd, J=9 Hz, J=3 Hz, 1H), 7.80 (s, 1H), 8.06 (d, J=9 Hz, 1H), 8.38 (s, 1H), 8.40 (d, J=9 Hz, 2H), 8.45 (dd, J=9 Hz, J=3 Hz, 1H), 8.90 (s, 1H); MS (DCI/NH$_3$) m/z 499 (M+H)$^+$.

Example 31

2-[2-(4-chloro-phenyl)-4-methyl-thiazol-5-yl]-6-{2-[(2R)-2-methyl-pyrrolidin-1-yl]-ethyl}-quinoline The title compound was prepared using the procedure described in Example 1G substituting 1-[2-(4-chloro-phenyl)-4-methyl-thiazol-5-yl]-ethanone (Dengle R. V. et. al. Indian J. Chem., Sect. B 1999, 39, p. 390–393) for 1-(4-methyl-2-thiophen-2-yl-thiazol-5-yl)-ethanone. $^1$H NMR (300 MHz, CD$_3$OD) δ 1.20 (d, J=6 Hz, 3H), 1.50 (m, 1H), 1.84 (m, 2H), 2.04 (m, 1H), 2.41 (q, J=6 Hz, 1H), 2.58 (m, 2H), 2.81 (s, 3H), 3.07 (m, 2H), 3.23 (m, 2H), 7.51 (d, J=6 Hz, 2H), 7.70 (dd, J=9 Hz, J=3 Hz, 1H), 7.78 (s, 1H), 7.84

(d, J=9 Hz, 1H), 7.99 (d, J=9 Hz, 3H), 8.33 (d, J=9 Hz, 1H); MS (DCI/NH$_3$) m/z 449 (M+H)$^+$.

Example 32

2-(5-methyl-3-phenyl-isoxazol-4-yl)-6-{2-[(2R)-2-methyl-pyrrolidin-1-yl]-ethyl}-quinoline The title compound was prepared using the procedure described in Example 1G substituting 1-(5-methyl-3-phenyl-isoxazol-4-yl)-ethanone (Umesha, K. B. et. al. Synth. Commun. 2002, 32, pages 1841–1846) for 1-(4-methyl-2-thiophen-2-yl-thiazol-5-yl)-ethanone. $^1$H NMR (300 MHz, CD$_3$OD) δ 1.18 (d, J=6 Hz, 3H), 1.47 (m, 1H), 1.83 (m, 2H), 2.04 (m, 1H), 2.38 (q, J=6 Hz, 1H), 2.49 (m, 2H), 2.62 (s, 3H), 3.06 (m, 2H), 3.18 (m, 2H), 7.23 (d, J=9 Hz, 1H), 7.39 (m, 5H), 7.71 (dd, J=9 Hz, J=3 Hz, 1H), 7.79 (s, 1H), 7.97 (d, J=9 Hz, 1H), 8.21 (d, J=9 Hz, 1H); MS (DCI/NH$_3$) m/z 398 (M+H)$^+$.

Example 33

6-{2-[(2R)-2-methyl-pyrrolidin-1-yl]-ethyl}-2-(3-phenyl-isoxazol-5-yl)-quinoline The title compound was prepared using the procedure described in Example 1G substituting 1-(3-phenyl-isoxazol-5-yl)-ethanone (Ohsawa, A. et. al. Heterocycles 1978, 9, pages 1367–1373) for 1-(4-methyl-2-thiophen-2-yl-thiazol-5-yl)-ethanone. $^1$H NMR (300 MHz, CD$_3$OD) δ 1.18 (d, J=6 Hz, 3H), 1.50 (m, 1H), 1.82 (m, 2H), 2.04 (m, 1H), 2.39 (q, J=6 Hz, 1H), 2.52 (m, 2H), 3.08 (m, 2H), 3.22 (m, 2H), 7.53 (m, 3H), 7.64 (s, 1H), 7.78 (dd, J=9 Hz, J=3 Hz, 1H), 7.85 (s, 1H), 7.99 (m, 2H), 8.10 (dd, J=9 Hz, J=3 Hz, 2H), 8.45 (d, J=9 Hz, 1H); MS (DCI/NH$_3$) m/z 384 (M+H)$^+$.

Example 34

2-[4-(4,5-dichloro-imidazol-1-yl)-phenyl]-6-{2-[(2R)-2-methyl-pyrrolidin-1-yl]-ethyl}-quinoline The title compound was prepared using the procedure described in Example 1G substituting 1-[4-(4,5-dichloro-imidazol-1-yl)-phenyl]-ethanone for 1-(4-methyl-2-thiophen-2-yl-thiazol-5-yl)-ethanone. $^1$H NMR (300 MHz, CD$_3$OD) δ 1.19 (d, J=6 Hz, 3H), 1.50 (m, 1H), 1.83 (m, 2H), 2.05 (m, 1H), 2.40 (q, J=6 Hz, 1H), 2.52 (m, 2H), 3.08 (m, 2H), 3.22 (m, 2H), 7.66 (d, J=9 Hz, 2H), 7.73 (dd, J=9 Hz, J=3 Hz, 1H), 7.82 (s, 1H), 7.99 (s, 1H), 8.05 (d, J=9 Hz, 1H), 8.08 (d, J=9 Hz, 1H), 8.37 (d, J=9 Hz, 2H), 8.39 (d, J=9 Hz, 1H); MS (DCI/NH$_3$) m/z 452 (M+H)$^+$.

Example 35

6-{2-[(2R)-2-methyl-pyrrolidin-1-yl]-ethyl}-2-(4-methyl-2-pyrrolidin-1-yl-pyrimidin-5-yl)-quinoline The title compound was prepared using the procedure described in Example 1G substituting 1-(4-methyl-2-pyrrolidin-1-yl-pyrimidin-5-yl)-ethanone (Arya, V. P. et. al. Indian J. Chem., Sect. B 1977, 15, pages 1129–1132) for 1-(4-methyl-2-thiophen-2-yl-thiazol-5-yl)-ethanone. $^1$H NMR (300 MHz, CD$_3$OD) δ 1.17 (d, J=6 Hz, 3H), 1.48 (m, 1H), 1.81 (m, 2H), 2.04 (m, 5H), 2.35 (q, J=6 Hz, 1H), 2.49 (m, 2H), 2.49 (S, 3H), 3.05 (m, 2H), 3.19 (m, 2H), 3.63 (m, 4H), 7.62 (d, J=9 Hz, 1H), 7.71 (dd, J=9 Hz, J=3 Hz, 1H), 7.82 (d, J=3 Hz, 1H), 7.98 (d, J=9 Hz, 1H), 8.34 (d, J=9 Hz, 1H), 8.40 (s, 1H); MS (DCI/NH$_3$) m/z 402 (M+H)$^+$.

Example 36

6-{2-[(2R)-2-(Methyl-d)-pyrrolidin-5,5-d$_2$-1-yl]-ethyl}-2-(4-methyl-2-pyrrolidin-1-yl-pyrimidin-5-yl)-quinoline

Example 36A (2R)-(Methyl-d)-pyrrolidine-5,5-d$_2$

A flask containing 20 mL (20 mmol) of a 1 M solution of LiAlD$_4$ in THF was cooled to 0° C. To this well stirred solution was added 1.35 g (5.0 mmol) of toluene-4-sulfonic acid 5-oxo-pyrrolidin-2(R)-ylmethyl ester (CAS #51693-17-5) in 22 mL of THF. The reaction was allowed to warm to 23° C., and stirred for 8 hours, then quenched by slow addition of 3.2 grams of powdered sodium sulfate decahydrate. After four hours, the reaction was treated with 5 g of anhydrous sodium sulfate. The solids were removed by filtration, washed with acetonitrile. Some loss of solvent to evaporation occurred, so the filtrate was diluted to a total volume of 25 mL to give a solution of the title compound.

Example 36B (2R)-2-(Methyl-d)-1-[2-(4-nitro-phenyl)-ethyl]-pyrrolidine-5,5-d$_2$ The title compound was prepared using the procedure described in Example 1B substituting the product of Example 36A for the product of Example 1A. $^1$H NMR (300 MHz, CD$_3$OD) δ 1.12 (m, 2H), 1.44 (m, 1H), 1.77 (t, J=6 Hz, 2H), 1.98 (m, 1H), 2.41 (m, 2H), 2.92 (m, 2H), 3.08 (m, 1H), 7.48 (d, J=9 Hz, 2H), 8.16 (d, J=9 Hz, 2H); MS (DCI/NH$_3$) m/z 237 (M+H)$^+$.

Example 36C

4-{2-[(2R)-2-(methyl-d)-1-pyrrolidin-5,5-d$_2$-yl]ethyl}aniline

The title compound was prepared using the procedure described in Example 1C substituting the product of Example 36B for the product of Example 1B.

Example 36D 2,2-Dimethyl-N-(4-{2-[(2R)-2-(methyl-d)-pyrrolidin-5,5-d$_2$-1-yl]-ethyl}phenyl)-propionamide The title compound was prepared using the procedure as described in Example 1D, substituting the product of Example 36C for the product of Example 1C. $^1$H NMR (300 MHz, CD$_3$OD) δ 1.13 (m, 2H), 1.28 (s, 9H), 1.46 (m, 1H), 1.77 (m, 2H), 1.98 (m, 1H), 2.31 (m, 1H), 2.43 (t, J=6 Hz, 2H), 2.80 (m, 2H), 3.02 (m, 1H), 7.18 (d, J=9 Hz, 2H), 7.43 (d, J=9 Hz, 2H); MS (DCI/NH$_3$) m/z 291 (M+H)$^+$.

Example 36E

N-(2-formyl-4-{2-[(2R)-2-(methyl-d)-1-pyrrolidin-5,5-d$_2$-yl]ethyl}phenyl)-2,2-dimethylpropanamide The title compound was prepared using the procedure described in Example 1E, substituting the product of Example 36D for the product from Example 1D.

Example 36F

2-Amino-5-{2-[(2R)-2-(methyl-d)-pyrrolidin-5,5-d$_2$-1-yl]-ethyl}-benzaldehyde

The title compound was prepared using the procedure described in Example 1F, substituting the product of Example 36E for the product of Example 1E. $^1$H NMR (300 MHz, CD$_3$OD) δ 1.14 (m, 2H), 1.46 (m, 1H), 1.79 (m, 2H), 1.98 (m, 1H), 2.31 (m, 1H), 2.43 (t, J=6 Hz, 1H), 2.80 (m, 2H), 3.02 (m, 1H), 6.70 (d, J=9 Hz, 1H), 7.20 (dd, J=9 Hz, J=3 Hz, 1H), 7.35 (d, J=3 Hz, 1H), 9.79 (s, 1H); MS (DCI/NH$_3$) m/z 236 (M+H)$^+$.

Example 36G

6-{2-[(2R)-2-(Methyl-d)-pyrrolidin-5,5-d$_2$-1-yl]-ethyl}-2-(4-methyl-2-pyrrolidin-1-yl-pyrimidin-5-yl)-quinoline The title compound was prepared using the procedure described in Example 1G substituting the product of Example 36F for the product of Example 1F and substituting 1-(4-methyl-2-pyrrolidin-1-yl-pyrimidin-5-yl)-ethanone (Arya, V. P. et. al. Indian J. Chem., Sect. B 1977, 15, p. 1129–1132) for 1-(4-methyl-2-thiophen-2-yl-thiazol-5-yl)-ethanone. $^1$H NMR (300 MHz, CD$_3$OD) δ 1.15 (m, 2H), 1.46 (m, 1H), 1.80 (m, 2H), 2.04 (m, 5H), 2.49 (m, 5H), 3.06 (m, 2H), 3.18 (m, 2H), 3.63 (m, 3H), 7.63 (d, J=9 Hz, 1H), 7.70 (dd, J=9 Hz, J=3 Hz, 1H), 7.80 (s, 1H), 7.98 (d, J=9 Hz, 1H), 8.34 (d, J=6 Hz, 1H), 8.40 (s, 1H); MS (DCI/NH$_3$) m/z 405 (M+H)$^+$.

Example 37

Determination of Biological Activity

To determine the effectiveness of representative compounds of this invention as histamine-3 receptor ligands (H$_3$ receptor ligands), the following tests were conducted according to methods previously described (European Journal of Pharmacology, 188:219–227 (1990); Journal of Pharmacology and Experimental Therapeutics, 275:598–604 (1995); Journal of Pharmacology and Experimental Therapeutics, 276:1009–1015 (1996); and Biochemical Pharmacology, 22:3099–3108 (1973)).

Briefly, male Sprague-Dawley rat brain cortices were homogenized (1 g tissue/10 mL buffer) in 50 mM Tris-HCl/5 mM EDTA containing protease inhibitor cocktail (Calbiochem) using a polytron set at 20,500 rpm. Homogenates were centrifuged for 20 minutes at 40,000×g. The supernatant was decanted, and pellets were weighed. The pellet was resuspended by polytron homogenization in 40 mL 50 mM Tris-HCl/5 mM EDTA with protease inhibitors and centrifuged for 20 minutes at 40,000×g. The membrane pellet was resuspended in 6.25 volumes (per gram wet weight of pellet) of 50 mM Tris-HCl/5 mM EDTA with protease inhibitors and aliquots flash frozen in liquid N$_2$ and stored at −70° C. until used in assays. Rat cortical membranes (12 mg wet weight/tube) were incubated with (3H)—N-α-methylhistamine (~0.6 nM) with or without H$_3$ receptor antagonists in a total incubation volume of 0.5 mL of 50 mM Tris-HCl/5 mM EDTA (pH 7.7). Test compounds were dissolved in DMSO to provide a 20 mM solution, serially diluted and then added to the incubation mixtures prior to initiating the incubation assay by addition of the membranes. Thioperamide (3 μM) was used to determine nonspecific binding. Binding incubations were conducted for 30 minutes at 25° C. and terminated by addition of 2 mL of ice cold 50 mM Tris-HCl (pH 7.7) and filtration through 0.3% polyethylenimine-soaked Unifilter plates (Packard). These filters were washed 4 additional times with 2 mL of ice-cold 50 mM Tris-HCl and dried for 1 hour. Radioactivity was determined using liquid scintillation counting techniques. Results were analyzed by Hill transformation and K$_i$ values were determined using the Cheng-Prusoff equation.

Generally, representative compounds of the invention demonstrated binding affinities in the above assay from about 810 nM to about 0.02 nM. Preferred compounds of the invention bound to histamine-3 receptors with binding affinities from about 100 nM to about 0.02 nM. More preferred compounds of the invention bound to histamine-3 receptors with binding affinities from about 20 nM to about 0.02 nM.

Compounds of the invention are histamine-3 receptor ligands that modulate function of the histamine-3 receptor by altering the activity of the receptor. These compounds may be inverse agonists that inhibit the basal activity of the receptor or they may be antagonists that completely block the action of receptor-activating agonists. These compounds may also be partial agonists that partially block or partially activate the histamine-3 receptor receptor or they may be agonists that activate the receptor.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

What is claimed is:

1. A compound of the formula:

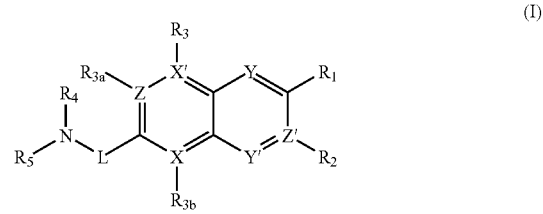

(I)

or a pharmaceutically acceptable salt, ester, amide, or prodrug thereof, wherein:

Y is N;

Y' is CH; or CF;

X, X', Z, and Z' are each;

R$_1$ is a group of the formula -L$_2$-R$_{6a}$-L$_3$-R$_{6b}$;

R$_2$ is selected from the group consisting of hydrogen, alkyl, alkoxy, aryl, cycloalkyl, halogen, cyano, and thioalkoxy;

R$_3$ is absent when X' is N or R$_3$ is selected from the group consisting of hydrogen, alkyl, alkoxy, halogen, cyano, and thioalkoxy;

R$_{3a}$ is selected from the group consisting of hydrogen, methyl, alkoxy, halogen, and cyano;

R$_{3b}$ is selected from the group consisting of hydrogen, alkyl, alkoxy, halogen, hydroxy, cyano, and thioalkoxy;

R$_4$ and R$_5$ are each independently selected from the group consisting of alkyl, haloalkyl, hydroxyalkyl, alkoxyalkyl, cycloalkyl, cycloalkylalkyl, and (NR$_A$R$_B$)alkyl, or R$_4$ and R$_5$ taken together with the nitrogen atom to which each is attached form a non-aromatic ring of the formula:

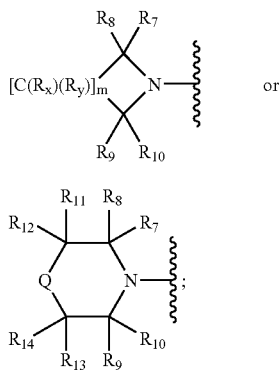

R$_7$, R$_8$, R$_9$, and R$_{10}$ at each occurrence are each independently selected from the group consisting of hydrogen, hydroxyalkyl, fluoroalkyl, and alkyl; or one of the pair R$_7$ and R$_8$ or the pair R$_9$ and R$_{10}$ is taken together to form a C$_3$–C$_6$ ring, wherein 0, 1, or 2 heteroatoms selected from O, N, or S replace a carbon atom in the ring;

R$_{11}$, R$_{12}$, R$_{13}$, and R$_{14}$ are each independently selected from the group consisting of hydrogen, hydroxy, hydroxyalkyl, alkyl, and fluoro;

R$_{6a}$ and R$_{6b}$ are each independently selected from the group consisting of a 5- to 6-membered heteroaryl, a 6-membered aryl, and a 5- to 6-membered heterocycle;

Q is selected from the group consisting of a bond, O, S, and NR$_{15}$;

L is —[C(R$_{16}$)(R$_{17}$)]$_k$—;

L$_2$ is selected from the group consisting of a bond, —O—, —C(=O)—, —S—, —[C(R$_{18}$)(R$_{19}$)]$_q$—, —O—[C(R$_{18}$)(R$_{19}$)]$_q$—, —NH— and —N(alkyl)-;

L$_3$ is selected from the group consisting of a bond, —[C(R$_{16}$)(R$_{17}$)]$_r$O—, —O—, —C(=O)—, —S—, —[C(R$_{18}$)(R$_{19}$)]$_q$—, —O—[C(R$_{18}$)(R$_{19}$)]$_q$—, —NH— and —N(alkyl)-;

R$_{15}$ is selected from the group consisting of hydrogen, alkyl, acyl, alkoxycarbonyl, amido, and formyl;

R$_{16}$ and R$_{17}$ at each occurrence are independently selected from the group consisting of hydrogen, alkyl, alkoxy, and fluoro;

R$_{18}$ and R$_{19}$ at each occurrence are each independently selected from the group consisting of hydrogen, hydroxy, alkyl, alkoxy, and fluoro;

R$_x$ and R$_y$ at each occurrence are independently selected from the group consisting of hydrogen, hydroxy, alkyl, alkoxy, alkylamino, dialkylamino, and fluoro, or one of R$_x$ or R$_y$ represents a covalent bond when taken together with R$_x$ or R$_y$ on an adjacent carbon atom such that a double bond is represented between the adjacent carbon atoms;

k is an integer from 1 to 6;
m is an integer from 1 to 5;
p is an integer from 2 to 6;
q is an integer from 1 to 4; and
r is an integer from 1 to 2.

2. The compound of claim 1, wherein R$_1$ is -L$_2$-R$_{6a}$-L$_3$-R$_{6b}$, wherein L$_2$ is a bond, L$_3$ is a bond or —CH$_2$O—, and R$_{6a}$ and R$_{6b}$ are each independently selected from a 5- or 6-membered heteroaryl ring, phenyl, and a non-aromatic 4- to 8-membered ring.

3. The compound of claim 2, wherein R$_{6a}$ and R$_{6b}$ are each independently selected from the group consisting of isoxazolyl, morpholinyl, phenyl, pyridazinyl, pyridinyl, pyrimidinyl, pyrazinyl, pyrazolyl, thiadiazolyl, thiazolyl, thienyl, triazolyl and cyclobutanyl.

4. The compound of claim 2, wherein R$_{6a}$ is selected from the group consisting of isoxazolyl, phenyl, pyrimidinyl, pyrazolyl, thiazolyl, thienyl, triazolyl, and cyclobutanyl; and R$_{6b}$ is selected from the group consisting of isoxazolyl, morpholinyl, phenyl, pyridazinyl, pyridinyl, pyrazinyl, pyrazolyl, thiadiazolyl, thiazolyl, and thienyl.

5. The compound of claim 1, wherein at least one of R$_{6a}$ and R$_{6b}$ is 5- to 6-membered heteroaryl.

6. The compound of claim 1, wherein R$_{6a}$ is 5- to 6-membered heteroaryl and R$_{6b}$ is 5- to 6-membered heterocycle.

7. The compound of claim 1, wherein R$_4$ and R$_5$ taken together with the nitrogen atom to which each is attached form a 4- to 8-membered non-aromatic ring represented by formula (a).

8. The compound of claim 7, wherein at least one substituent represented by R$_7$, R$_8$, R$_9$, and R$_{10}$ is selected from the group consisting of alkyl, fluoroalkyl, and hydroxyalkyl or at least one substituent represented by R$_x$ or R$_y$ is selected from the group consisting of hydrogen, hydroxy, and fluoro.

9. The compound of claim 1, wherein R$_4$ and R$_5$ are taken together with the nitrogen atom to which each is attached to form a (2R)-methylpyrrolidine ring.

10. The compound of claim 1, selected from the group consisting of

6-{2-[(2R)-2-methylpyrrolidin-1-yl]ethyl}-2-(4-methyl-2-thien-2-yl 1,3-thiazol-5-yl)quinoline;

6-[2-((2R)-2-methyl-pyrrolidin-1-yl)-ethyl]-2-[2-(4-methyl-[1,2,3]thiadiazol-5-yl)-thiazol-4-yl]-quinoline;

2-(4-methyl-2-pyrazin-2-yl-thiazol-5-yl)-6-[2-((2R)-2-methyl-pyrrolidin-1-yl)-ethyl]-quinoline;

2-[1-(3,4-dichloro-phenyl)-5-methyl-1H-pyrazol-4-yl]-6-[2-((2R)-2-methyl-pyrrolidin-1-yl)-ethyl]-quinoline;

2-[2-(4-chloro-phenoxymethyl)-thiazol-4-yl]-6-[2-((2R)-2-methyl-pyrrolidin-1-yl)-ethyl]-quinoline;

2-(5-methyl-1-pyridin-2-yl-1H-pyrazol-4-yl)-6-[2-((2R)-2-methyl-pyrrolidin-1-yl)-ethyl]-quinoline;

2-[5-methyl-1-(6-methyl-4-trifluoromethyl-pyridin-2-yl)-1H-pyrazol-4-yl]-6-[2-((2R)-2-methyl-pyrrolidin-1-yl)-ethyl]-quinoline;

2-[3-(4-chloro-phenyl)-isoxazol-5-yl]-6-[2-((2R)-2-methyl-pyrrolidin-1-yl)-ethyl]-quinoline;

6-[2-(2R)-2-methyl-pyrrolidin-1-yl)-ethyl]-2-[5-(1-methyl-5-trifluoromethyl-1H-pyrazol-3-yl)-thiophen-2-yl]-quinoline;

2-(4-methyl-2-morpholin-4-yl-thiazol-5-yl)-6-[2-((2R)-2-methyl-pyrrolidin-1-yl)-ethyl]-quinoline;

6-[2-((2R)-2-methyl-pyrrolidin-1-yl)-ethyl]-2-(2-phenyl-thiazol-5-yl)-quinoline;

2-(4-methyl-2-pyridin-2-yl-thiazol-5-yl)-6-[2-((2R)-2-methyl-pyrrolidin-1-yl)-ethyl]-quinoline;

2-[3-(3-chloro-5-trifluoromethyl-pyridin-2-yl)-isoxazol-5-yl]-6-[2-((2R)-2-methyl-pyrrolidin-1-yl)-ethyl]-quinoline;

2-(4-methyl-2-pyridin-3-yl-thiazol-5-yl)-6-[2-((2R)-2-methyl-pyrrolidin-1-yl)-ethyl]-quinoline;

2-(4-methyl-2-pyridin-4-yl-thiazol-5-yl)-6-[2-((2R)-2-methyl-pyrrolidin-1-yl)-ethyl]-quinoline;

6-[2-((2R)-2-methyl-pyrrolidin-1-yl)-ethyl]-2-(2-phenyl-thiazol-4-yl)-quinoline;

2-[3-(4-chloro-phenyl)-5-methyl-isoxazol-4-yl]-6-[2-((2R)-2-methyl-pyrrolidin-1-yl)-ethyl]-quinoline;

1-(4-{6-[2-((2R)-2-methyl-pyrrolidin-1-yl)-ethyl]-quinolin-2-yl}-phenyl)-1H-pyridin-4-one;

6-[2-((2R)-2-methyl-pyrrolidin-1-yl)-ethyl]-2-(4-piperidin-1-yl-phenyl)-quinoline;

2-(5'-methyl-[2,2']bithiophenyl-5-yl)-6-[2-((2R)-2-methyl-pyrrolidin-1-yl)-ethyl]-quinoline;

2-(6-methyl-2-phenyl-pyrimidin-4-yl)-6-[2-((2R)-2-methyl-pyrrolidin-1-yl)-ethyl]-quinoline;

2-(5-chloro-1-methyl-3-phenyl-1H-pyrazol-4-yl)-6-[2-((2R)-2-methyl-pyrrolidin-1-yl)-ethyl]-quinoline;

6-[2-((2R)-2-methyl-pyrrolidin-1-yl)-ethyl]-2-(1-pyridin-3-yl-cyclobutyl)-quinoline;

2-methyl-3-[1-(5-methyl-isoxazol-3-yl)-1H-[1,2,4]triazol-3-yl]-6-[2-((2R)-2-methyl-pyrrolidin-1-yl)-ethyl]-quinoline;

2-[1-(2,4-difluoro-phenyl)-5-methyl-1H-[1,2,3]triazol-4-yl]-6-{2-[(2R)-2-methyl-pyrrolidin-1-yl]-ethyl}-quinoline;

2-[1-(6-ethoxy-pyridazin-3-yl)-5-methyl-1H-pyrazol-4-yl]-6-{2-[(2R)-2-methyl-pyrrolidin-1-yl]-ethyl}-quinoline;

2-(2'-methyl-[2,4']bithiazolyl-4-yl)-6-{2-[(2R)-2-methyl-pyrrolidin-1-yl]-ethyl}-quinoline;

2-[2-(5-methyl-isoxazol-3-yl)-thiazol-4-yl]-6-{2-[(2R)-2-methyl-pyrrolidin-1-yl]-ethyl}-quinoline;

2-[2-(2,6-dichloro-pyridin-4-yl)-thiazol-4-yl]-6-{2-[(2R)-2-methyl-pyrrolidin-1-yl]-ethyl}-quinoline;

6-{2-[(2R)-2-methyl-pyrrolidin-1-yl]-ethyl}-2-{2-[6-(2,2,2-trifluoro-ethoxy)-pyridin-3-yl]-thiazol-4-yl}-quinoline;

2-[2-(4-chloro-phenyl)-4-methyl-thiazol-5-yl]-6-{2-[(2R)-2-methyl-pyrrolidin-1-yl]-ethyl}-quinoline;

2-(5-methyl-3-phenyl-isoxazol-4-yl)-6-{2-[(2R)-2-methyl-pyrrolidin-1-yl]-ethyl}-quinoline;

6-{2-[(2R)-2-methyl-pyrrolidin-1-yl]-ethyl}-2-(3-phenyl-isoxazol-5-yl)-quinoline;

2-[4-(4,5-dichloro-imidazol-1-yl)-phenyl]-6-{2-[(2R)-2-methyl-pyrrolidin-1-yl]-ethyl}-quinoline; and 6-{2-[(2R)-2-methyl-pyrrolidin-1-yl]-ethyl}-2-(4-methyl-2-pyrrolidin-1-yl-pyrimidin-5-yl)-quinoline.

11. A pharmaceutical composition comprising a therapeutically effective amount of a compound of claim 1 in combination with a pharmaceutically acceptable carrier.

12. A method of treating Alzheimer's disease, attention-deficit hyperactivity disorder, or schizophrenia comprising administering a compound of claim 1.

13. A method of treating cognitive deficits of schizophrenia comprising administering a compound of claim 1.

* * * * *

UNITED STATES PATENT AND TRADEMARK OFFICE
CERTIFICATE OF CORRECTION

| | | |
|---|---|---|
| PATENT NO. | : 7,098,222 B2 | Page 1 of 1 |
| APPLICATION NO. | : 11/123620 | |
| DATED | : August 29, 2006 | |
| INVENTOR(S) | : Robert J Altenbach et al. | |

It is certified that error appears in the above-identified patent and that said Letters Patent is hereby corrected as shown below:

On title page, item 75 Inventors
 Delete the following inventors
 Lawrence A. Black, Libertyville, IL (US); Sou- Jen Chang, Prairie View, IL (US); Ramin Faghih, Lake Forest, IL (US); Gregory A. Gfesser, Lindenhurst, IL (US); Yi-Yin Ku, Buffalo Grove, IL (US); Kirill A. Lukin, Mundelein, IL (US); Diana L. Nersesian, Gurnee, IL (US); Michael P. Curtis, Kenosha, WI (US);

Col. 72, line 64
 replace "Y' is CH; or CF;"
 with --Y' is CH or CF;--.

Col. 72, line 66
 replace "X, X', Z, and Z' are each;"
 with --X, X', Z, and Z' are each C;--.

Col. 73, line 4
Delete $R_3$ is absent when X' is N or

Signed and Sealed this

Fourth Day of March, 2008

JON W. DUDAS
*Director of the United States Patent and Trademark Office*

UNITED STATES PATENT AND TRADEMARK OFFICE
CERTIFICATE OF CORRECTION

PATENT NO. : 7,098,222 B2 Page 1 of 1
APPLICATION NO. : 11/123620
DATED : August 29, 2006
INVENTOR(S) : Robert J. Altenbach et al.

It is certified that error appears in the above-identified patent and that said Letters Patent is hereby corrected as shown below:

On title page, item 75 Inventors
  Delete the following inventors
  Lawrence A. Black, Libertyville, IL (US); Sou- Jen Chang, Prairie View, IL (US); Ramin Faghih, Lake Forest, IL (US); Gregory A. Gfesser, Lindenhurst, IL (US); Yi-Yin Ku, Buffalo Grove, IL (US); Kirill A. Lukin, Mundelein, IL (US); Diana L. Nersesian, Gurnee, IL (US); Michael P. Curtis, Kenosha, WI (US), Yu-ming Pu, Gurnee, IL (US)

Col. 72, line 64
  replace "Y' is CH; or CF;"
  with --Y' is CH or CF;--.

Col. 72, line 66
  replace "X, X', Z, and Z' are each;"
  with --X, X', Z, and Z' are each C;--.

Col. 73, line 4
Delete $R_3$ is absent when X' is N or

This certificate supersedes the Certificate of Correction issued March 4, 2008.

Signed and Sealed this

First Day of April, 2008

JON W. DUDAS
*Director of the United States Patent and Trademark Office*